(12) United States Patent
Lellouche et al.

(10) Patent No.: US 8,486,534 B2
(45) Date of Patent: Jul. 16, 2013

(54) SURFACE-MODIFIED POLYMER FILMS

(75) Inventors: Jean-Paul Lellouche, Ashdod (IL);
Maria Naddaka, Petach Tiqva (IL);
Anna Peled, Tel Aviv (IL); Esabul Mondal, Dist-Burdwan (W.B.) (IL)

(73) Assignee: Bar-Ilan University, Ramat Gan (IL)

( * ) Notice: Subject to any disclaimer, the term of this patent is extended or adjusted under 35 U.S.C. 154(b) by 79 days.

(21) Appl. No.: 13/154,727

(22) Filed: Jun. 7, 2011

(65) Prior Publication Data

US 2011/0306722 A1 Dec. 15, 2011

Related U.S. Application Data

(60) Provisional application No. 61/344,191, filed on Jun. 8, 2010, provisional application No. 61/344,331, filed on Jun. 30, 2010.

(51) Int. Cl.
*H01L 21/76* (2006.01)
*C09D 165/04* (2006.01)

(52) U.S. Cl.
USPC .................................... 428/411.1; 524/588

(58) Field of Classification Search
None
See application file for complete search history.

(56) References Cited

U.S. PATENT DOCUMENTS

2010/0239824 A1* 9/2010 Weitz et al. .................... 428/172
2011/0123413 A1* 5/2011 Abate et al. .................... 422/502

FOREIGN PATENT DOCUMENTS

WO WO 2009120254 A1 * 10/2009

OTHER PUBLICATIONS

Abate et al. "Glass coating for PDMS microfluidic channels by sol-gel methods" Lab Chip, 2008, 8, 516-518.*
Kim et al. "Organic-Inorganic hybrid photoinitiator with reduced volume shrinkage" Appl. Phys. Lett. 87, 2005, 1-3.*
Ven den Brom et al. "The swelling behavior of thermoresponsive hydrogel/silica nanoparticle composites" J. Mater. Chem. 2010, 20, 4827-4839.*
Abate et al. "Photoreactive coating for high-contrast spatial patterning of microfluidic device wettability" Lab Chip 2008, 8, 2157-2160.*
Applerot, et al., "Decorating Parylene-Coated Glass with Zno Nanoparticles for Antibacterial Applications: A Comparative Study of Sonochemical, Microwave, and Microwave-Plasma Coating Routes", ACS Applied Materials Interfaces, 2010, pp. 1052-1059, vol. 2.
Bartlett, et al., "Fabrication of Polymer Thin Films and Arrayswith Spatial and Topographical Controls", Advanced Materials and Processes, 2001, pp. 1449-1451, vol. 13, No. 19.
Bara, et al., "Comparison of the photodegradation of parylene C and parylene N", European Polymer Journal, 2000, pp. 1765-1777, vol. 36.
Gann, et al., "A Versatile Method for Grafting Polymers on Nanoparticles", Langmuir, 2008, pp. 5319-5323, vol. 24.

(Continued)

*Primary Examiner* — Robert S Loewe
(74) *Attorney, Agent, or Firm* — Browdy and Neimark, PLLC

(57) ABSTRACT

Surface-modified polymer films for coating are provided, wherein the surface is modified by covalent binding of nano- or micro-particles comprising a photoreactive species. The surface of the polymer film, e.g. a parylene film, may be modified by covalent binding of nano- or micro-particles of a polymer, e.g. a conductive bifunctional polymer further comprising a chemically reactive functional group, or of a hybrid organic-inorganic oxide, e.g., silica, network comprising a photoreactive species. Further provided are: (i) polymerizable monomers, the conductive bifunctional polymers obtained therefrom; (ii) a hybrid photoreactive organic-inorganic oxide network; and (iii) micro- or nano-particles made from (i) or (ii).

12 Claims, 22 Drawing Sheets

OTHER PUBLICATIONS

Goda, et al., "Photoinduced phospholipid polymer grafting on Parylene film: Advanced lubrication and antibiofouling properties", Colloids and Surfaces B: Biointerfaces, 2007, pp. 67-73, vol. 54.

Herrera-Alonso, et al., "Chemical Surface Modification of Poly(p-xylylene) Thin Films", Langmuir, 2004, pp. 9184-9189, vol. 20.

Mori, et al., "Photoconduction of poly-p-xylylene films: effects of plasma modification and oxidation", Journal of Physics D: Applied Physics, 1990, pp. 338-341, vol. 23.

Peled, et al., "A new method for the preparation of silica-polycarbazole composite particles of a core-shell morphology", Journal of Materials Chemistry, 2009, pp. 268-273, vol. 19.

Pruden, et al., "Characterization of Parylene-N and Parylene-C Photooxidation", Journal of Polymer Science: Part A: Polymer Chemistry, 2003, pp. 1486-1496, vol. 41.

Rohr, et al., "Surface Functionalization of Thermoplastic Polymers for the Fabrication of Microfluidic Devices by Photoinitiated Grafting", Advanced Functional Materials, 2003, pp. 264-270, vol. 13, No. 4.

Ten Eyck, et al., "Plasma-Enhanced Atomic Layer Deposition of Palladium on a Polymer Substrate", Chemical Vapor Deposition, 2007, pp. 307-311, vol. 13.

\* cited by examiner

US 8,486,534 B2

SURFACE-MODIFIED POLYMER FILMS

FIELD OF THE INVENTION

The present invention is in the field of chemistry and relates to surface-modified polymeric films useful for coating. The surface modification is achieved by covalent modification using hybrid photoreactive inorganic oxide nanoparticles or by chemical functionalization of the polymeric films using photoreactive reagents or polymeric micro- or nano-particles. The invention also relates to polymerizable monomers and to hybrid organic-inorganic oxides comprising a photoreactive moiety useful for the surface-modification of polymeric films.

BACKGROUND

Most of the biomedical devices are manufactured from polymers and metals that are far from being biocompatible. Instead of developing new biomaterials, surface coating with polymeric thin films represents a convenient method for their modification and protection.

Polymeric thin film coatings represent a practical alternative to surface modifications since they preserve the properties of underlying materials while allowing, through a judicious choice of the coating method and polymer, to control macroscopic surface properties such as biocompatibility, electrical conductivity, specific optical properties, hardness/erosion resistance, and adhesion. Amongst the various known coating techniques, chemical vapor deposition (CVD) has gained substantial interest in recent years since (i) it proceeds at room temperature in the absence of solvent, and (ii) produces deposited films of uniform thickness with an excellent thickness and conformality control, as well as polymer purity. One of the most widely studied chemical vapor deposited family of polymers is the family of parylene (poly-paraxylylene) polymers, which, due to their excellent electrical insulation, low dielectric constant, barrier and chemical/thermal stabilities, and biocompatibility properties have found a wide use in electronic and biological/medical applications.

However and generally speaking, parylene coatings have a highly hydrophobic non-functional nature and their chemically stable surfaces do not fully satisfy attractive properties such as antibiofouling, water wettability, and lubricity properties necessary for a wide range of biological applications.

Accordingly, there is an urgent need for developing simple, cost effective, and reproducible methods that will enable the incorporation of chemically reactive functional groups or nanostructures onto parylene film surfaces. This step is essential to infer new properties to parylene films and, consequently to any film of the numerous other known polymer coatings that possess similar surface properties, thus greatly expanding their scope of potential applications.

SUMMARY OF THE INVENTION

In one aspect, the present invention relates to a surface-modified polymer film for coating, wherein the surface of said polymer film is modified by covalent binding of nano- or micro-particles comprising a photoreactive species. In certain embodiments, the polymer film is a parylene film, In certain embodiments, the polymer film is modified by covalent binding of nano- or micro-particles of a polymer or of a hybrid organic-inorganic oxide network comprising a photoreactive species. The polymer comprising a photoreactive species may be a conductive bifunctional polymer further comprising a chemically reactive functional group. In certain embodiments, the polymer is polycarbazole.

In another aspect, the present invention relates to polymerizable monomers, the conductive bifunctional polymers obtained therefrom and the micro- or nano-particles made from said polymers.

In a further aspect, the present invention relates to a hybrid photoreactive organic-inorganic oxide network and to micro- or nano-particles made thereof. In certain embodiments, the inorganic oxide is silica.

The invention further relates to surface-modified films obtained from the original modified films by a second modification step.

The invention allows obtaining polymer films, particularly parylene films, with new/improved properties greatly expanding their scope of applications in electronic and biological applications.

BRIEF DESCRIPTION OF THE FIGURES

FIG. 6A shows a $^{13}C$ CP/MAS NMR spectrum of $SiO_2$@PA nanoparticles and the $^{13}C$ NMR (75 MHz; $CD_3SOCD_3$) spectrum of PATES. FIG. 6B shows a $^{13}C$ CP/MAS NMR spectrum of $SiO_2$@PFPA nanoparticles and the $^{13}C$ NMR (75 MHz; $CDCl_3$) spectrum of PFPATES. FIG. 6C shows a $^{13}C$ CP/MAS NMR spectrum of $SiO_2$@BPh nanoparticles and the $^{13}C$ NMR (75 MHz; $CD_3SOCD_3$) spectrum of BPhTES.

FIG. 11A shows an AFM image of a PC—SiO$_2$@PFPA film; FIG. 11B shows an AFM image of a PC—SiO$_2$@PA film; and FIG. 11C shows an AFM image of a PC—SiO$_2$@BPh film.

DETAILED DESCRIPTION OF THE INVENTION

Figure 1A:
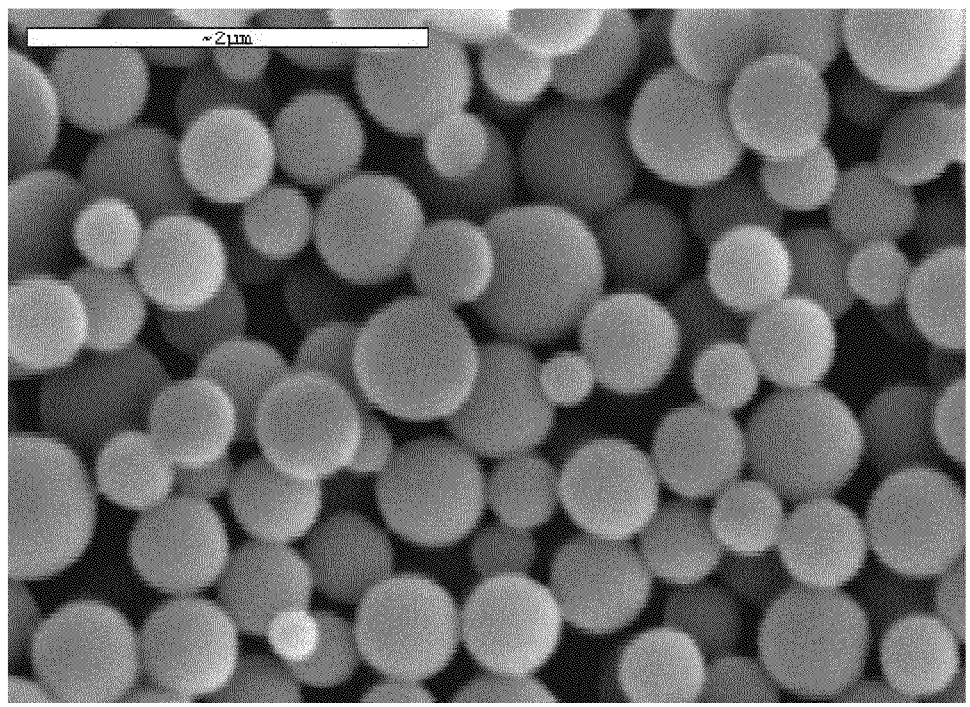
FIGS. 1A-1D show characterization of Compound 7 (poly((S)-6-(4-benzoyl-benzoylamino)-2-carbazol-9-yl-hexanoic acid)-based polymeric particles by SEM (FIG. 1A), HR-SEM (FIG. 1B), FT-IR (FIG. 1C) and visible UV (FIG. 1D).

When considering chemical modifications of deposited parylene films, this task is quite challenging due to the known chemical stability/inertness of this kind of polymers.

There are two basic approaches for parylene functionalization. The first method involves incorporation of functional groups through the synthesis and polymerization of functionalized [2.2]paracyclophanes (Lahann et al., 1998, 2002; Chen et al., 2006; Greiner et al., 1997; Lahann and Langer, 2002). In another approach, post-modifications of parylene films were applied, including electrophilic aromatic substitution (Herrera-Alonso et al., 2004), plasma treatment (Mori et al., 1990; Ten Eyck et al., 2007), and photo-oxidation (Bera et al., 2000; Pruden et al., 2003). Recently, the photoinitiated polymerization grafting of parylene films by polyacrylates has been described (Goda et al., 2007; Rohr et al., 2003). A poly(2-methacryloyloxyethyl phosphoryl-choline) polyacrylate polymer was grafted on parylene C films using UV irradiation in the presence of benzophenone (BPh) as a polymerization initiator to provide lubrication and an antibiofouling surface (Goda et al., 2007). Finally, only few works report the incorporation of nanostructures to parylene films and all of them are based on physical interactions between the parylene film and the nanoparticles (NPs) (Applerot et al., 2010).

For example, harsh plasma treatment (Mori et al., 1990; Ten Eyck et al., 2007) and photooxidation reactions in the presence of air (Bera et al., 2000; Pruden et al., 2003) afforded oxidized surface layers containing mainly mixtures of oxygenated and/or aminated functions (see Table 1 below).

TABLE 1

| Incorporated group | Method | Ref |
|---|---|---|
| C=O, C—O, (O=C)—O, O—(C=O)—O, C—O—C | Argon plasma | Mori et al. |
| —CH$_2$—(C=O)—, —(C=O)—(C=O)— | Ozone oxidation | Mori et al |
| (C=O)—H, (C=O)—OH | UV (254 nm) irradiation in air | Pruden et al. |
| NH$_2$ | H$_2$/N$_2$(1/1.5 feed ratio) plasma | Ten Eyck et al. |

In an another approach, the synthesis and polymerization of functionalized [2.2]paracyclophanes as parylene precursors were also widely investigated and yielded parylene-based surfaces possessing a wide variety of functional groups in agreement with the process described below. The incorporated chemical functions are shown in Table 2 (Lahann and Langer, 2002; Lahann et al., 1998, 2011, 2002, 2003; Chen et al., 2006; Greiner et al., 1997):

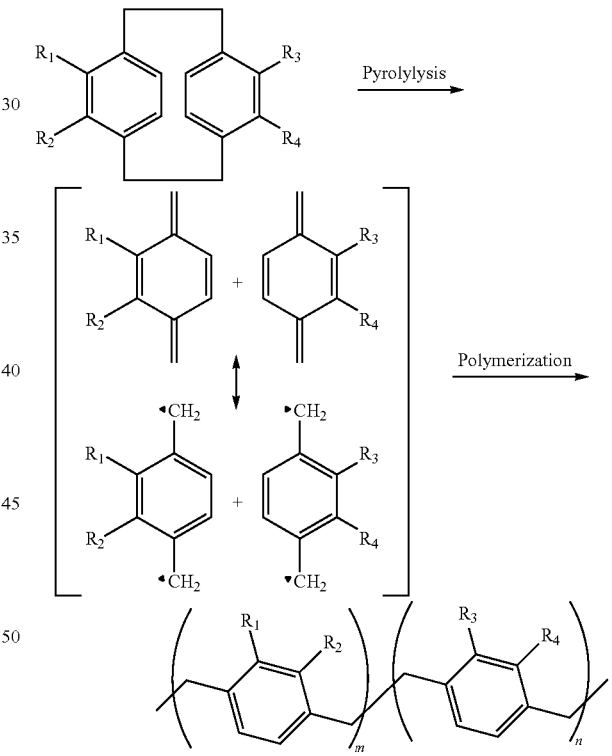

TABLE 2

Incorporated chemical functions introduced by polymerization/deposition of functional [2.2]paracyclophanes

| Incorporated group | | | | |
|---|---|---|---|---|
| R$_1$ | R$_2$ | R$_3$ | R$_4$ | Ref. |
| —CH$_2$OH | H | H | H | Lahann et al (2002); 1998) |

TABLE 2-continued

Incorporated chemical functions introduced by polymerization/deposition of functional [2.2]paracyclophanes

| R$_1$ | R$_2$ | R$_3$ | R$_4$ | Ref. |
|---|---|---|---|---|
| —CH$_2$OCH$_3$ | H | H | H | Lahann et al (2002) |
| —CH$_2$OCOCH$_3$ | H | H | H | Lahann et al (2002) |
| —COOCH$_3$ | H | H | H | Lahann et al (2002) |
| —COOCH$_3$ | —COOCH$_3$ | —COOCH$_3$ | —COOCH$_3$ | Lahann et al (2002) |
| —COOCH$_3$ | —COOCH$_3$ | —COOCH$_3$ | —COOCH$_3$ | Lahann et al (2002); |
| (anhydride group) | | (anhydride group) | | Lahann et al (2002a); (1998); (2001) |
| (ester group) | | (ester group) | | Lahann et al (2002) |
| NH$_2$ | H | H | H | Lahann et al (2002) (1998); Chen et al (2006) |
| NH$_2$ | H | NH$_2$ | H | Lahann et al (2002) |
| (pentafluorophenyl ester) | H | H | H | (2003); (2002a); (2001); (2002)(b); Chen et al (2006) |
| —CH$_2$OCOCF$_3$ | H | H | H | Lahann et al (2002); |
| —COCF$_3$ | H | H | H | Lahann et al (2003); (1998); Chen et al (2006) |
| —COCF$_2$CF$_3$ | H | H | H | Chen et al (2006) |
| —CH$_2$OSO$_2$CF$_3$ | H | H | H | Lahann et al (2002); |
| —COPh | H | H | H | Chen et al (2006) |
| —CH$_3$ | H | H | CH$_3$ | Greiner et al (1997) |
| —CH$_2$CH$_3$ | H | H | —CH$_2$CH$_3$ | Greiner et al (1997) |
| —CN | H | H | CN | Greiner et al (1997) |
| —Br | H | H | Br | Greiner et al (1997) |
| —Cl | H | H | Cl | Greiner et al (1997) |

In addition, Herrera-Alonso and McCarthy (2004) reported the chemical surface modification of parylene films through reactions at the aromatic ring using electrophilic aromatic substitutions (see Table 3 below).

TABLE 3

Chemical functions introduced into parylene films using post-CVD aromatic electrophilic substitutions

| Entry # | Incorporated group | Reagents |
|---|---|---|
| 1 | 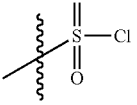 | HOSO$_2$Cl |

TABLE 3-continued

Chemical functions introduced into parylene films using post-CVD aromatic electrophilic substitutions

| Entry # | Incorporated group | Reagents |
|---|---|---|
| 2 | –S(=O)(=O)–O⁻ Na⁺ | 1 + NaOH/H$_2$O |
| 3 | –CH$_2$–NH–C(=O)–CH$_2$Cl | HO–CH$_2$–NH–C(=O)–CH$_2$Cl / H$_2$SO$_4$ |
| 4 | –CH$_2$–NH$_2$·HCl | 3 + HCl/EtOH |
| 5 | –CH$_2$–N=CH–C$_6$F$_5$ | 4 + C$_6$F$_5$–CHO |
| 6 | –CH(CH$_3$)–CH$_2$OH | propylene oxide / SnCl$_4$ |
| 7 | –CH(CH$_3$)–CH$_2$–O–C(=O)–CF$_3$ | 6 + (CF$_3$CO)$_2$O |
| 8 | –C(=O)–CH$_2$–CH$_2$–COOH | succinic anhydride / AlCl$_3$ |
| 9 | –C(=O)–CH$_2$–CH$_2$–C(=O)–O–CH$_2$CF$_3$ | 8 + CF$_3$CH$_2$OH |
| 10 | –C(=O)–CF$_3$ | (CF$_3$CO$_2$)$_2$O / AlCl$_3$ |
| 11 | –C(=O)–CH$_2$–CH$_2$–Cl | Cl–C(=O)–CH$_2$–CH$_2$–Cl |

Recently, the photoinitiated polymerization grafting of parylene films by polyacrylates has been described (Goda et al., 2007; Rohr et al., 2003; Williams et al., 2008). A poly(2-methacryloyloxyethyl phosphoryl-choline) polyacrylate polymer was grafted onto parylene C films using UV irradiation in the presence of benzophenone as a polymerization initiator (Goda et al., 2007).

Contrary to the previous approaches, the present invention provides a novel method for functionalization/surface structuration of films of parylene and of other polymers with similar characteristics using nano- or micro-particles comprising a photoreactive reagent/species.

Thus, in one aspect, the present invention relates to a surface-modified polymer film for coating, wherein the surface of said polymer film is modified by the covalent binding of nano- or micro-particles comprising a photoreactive species.

In certain embodiments, the polymer is selected from, but not limited to, parylenes, polystyrenes, cross-linked poly(styrene/divinylbenzene), (meth)acrylates), polylactic acid, polylactic-polyglycolic acids copolymers, polysulfones, polyurethanes, polyethyleneglycol polymers and co-polymers with poly(meth)acrylates, polythiophenes, polycarbazoles, polyanilines, polypyrroles, polyethylenes, polypropylenes, poly(vinylchloride), polyacrylonitriles, polyvinylacetates, polyamides, polyesters, polyethylene therephtalates, polysilazanes and poly(methylsilynes).

In some embodiments, the polymer is a parylene (polyxylylene) and may be parylene C (PC, poly-2-chloro-xylylene), parylene N (PN, poly-xylylene), parylene D (PD, poly-2,5-dichloro-xylylene), or fluorinated parylene F ($-CF_2-C_6H_4-CF_2-)_n$. In certain preferred embodiments, the polymer is parylene C.

In some embodiments, the surface of the polymer film is modified by covalent binding of nano- or micro-particles of a polymer comprising a photoreactive species. In some other embodiments, the surface of the polymer film is modified by the covalent binding of a hybrid organic-inorganic oxide network comprising a photoreactive species.

When the surface of the polymer film is modified by the covalent binding of nano- or micro-particles of a polymer comprising a photoreactive species, the polymer may be a bifunctional polymer further comprising a chemically reactive functional group. This functional group is useful for second step derivatization as will be described hereinafter in the specification.

In some embodiments, the bifunctional polymer used for modifying the surface of the polymeric film is an electrically conductive bifunctional polymer such as, but not limited to, polycarbazole, polypyrrole, polythiophene and polyaniline, further comprising a chemically reactive functional group such as, but not limited to, a carboxy group that may be esterified with an alcohol or a thiol, or an amido group.

The photoreactive or photoactivatable reagent or species (the terms 'reagent' and 'species' are used herein interchangeably) is a UV-activated reagent and is, in certain embodiments, a simple aryl azide, a fluorinated aryl azide, a diaryl ketone, or a fluorinated (aryl)aziridine.

According to the invention, the conductive bifunctional polymer is composed of monomers in which the chemically reactive functional group and the photoreactive moiety are linked through an aliphatic chain comprising at least one divalent radical such as $-O-CO-$, $-CO-O-$, $-NH-CO-$, $-CO-NH-$, $-CH=CH-$, $-C\equiv C-$ and $-O-Si-O-$, said at least one divalent radical being attached to the photoreactive group.

Accordingly, in certain embodiments, the bifunctional polymer comprising a photoreactive species is a polymer obtained by polymerization of one or more monomers of the formula I:

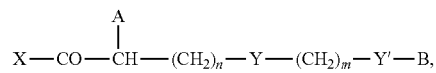

wherein
X is a moiety of a chemically reactive functional group capable of reacting with a nucleophile;
A is an oxidizable group;
Y and Y' each is a divalent radical, wherein one of Y or Y' may be absent;
B is a moiety of a photoreactive reagent;
n is 1 to 15; and
m is 0 to 15.

In some embodiments, the bifunctional polymer is obtained by polymerization of a sole monomer of the formula I.

In certain embodiments, in the bifunctional monomer the formula I:
X is OR, NRR', or SR, wherein R and R' each independently is H, alkyl or aryl;
A is a moiety derived from a carbazole, pyrrole, thiophene, or aniline;
Y and Y' each independently is a divalent radical selected from the group consisting of $-O-CO-$, $-CO-O-$, $-NH-CO-$, $-CO-NH-$, $-CH=CH-$, $-C\equiv C-$, and $-O-Si-O-$, or one of them is absent;
B is a moiety of a photoreactive reagent selected from the group consisting of aryl azides, diaryl ketones, fluorinated aziridines and fluorinated aryl aziridines;
n is 1 to 6; and m
m is 0 to 6.

In certain other embodiments, the bifunctional monomer has the formula I wherein:
X is OH;
A is a moiety derived from a carbazole;
Y is $-NH-CO-$ and Y' is absent, or Y is $-CO-O-$ and Y' is $O-CO-$;
B is a moiety of an aryl azide selected from the group consisting of phenyl azide, tetrafluorophenyl azide, hydroxyphenyl azide, and nitrophenyl azide; or a moiety of a diaryl ketone selected from the group consisting of unsubstituted benzophenone and benzophenone substituted by one or more carboxyl, azido, amino or hydroxy groups;
n is 1, 2, 4 or 6; and
m is 0, 2 or 4.

If the monomers of formula I have chiral centers, it should be noted that the basic photochemical attachment reactivity caused by UV does not depend on the absolute chirality of these carbazole (Cbz)-based monomers. Thus, both the racemic and any stereochemically pure monomer (R or S) or non-racemic R/S mixtures are suitable for use according to the invention.

In certain preferred embodiments, the Cbz-based monomers of the formula I are selected from the compounds:
(i) 6-(4-benzoyl-benzoylamino)-2-carbazol-9-yl-hexanoic acid, in its racemic or chiral form, preferably the S isomer of the formula:

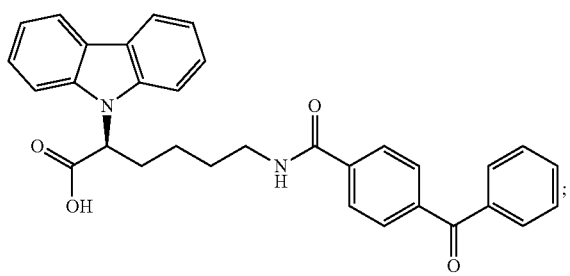 [SMILES: O=C(NCCCC[C@@H](C(=O)O)n1c2ccccc2c2ccccc21)c1ccc(C(=O)c2ccccc2)cc1]

(ii) 6-(4-azido-benzoylamino)-2-carbazol-9-yl-hexanoic acid in its racemic or chiral form, preferably the S isomer of the formula:

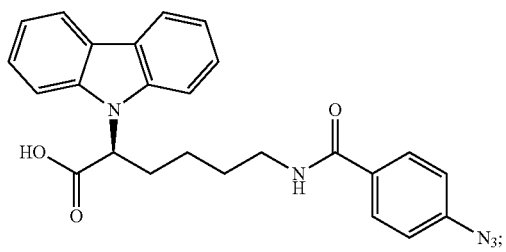 [SMILES: [N-]=[N+]=Nc1ccc(C(=O)NCCCC[C@@H](C(=O)O)n2c3ccccc3c3ccccc32)cc1]

(iii) 4-(2-(4-azidobenzoyloxy)ethoxy)-2-(9H-carbazol-9-yl)-4-oxobutanoic acid, in its racemic or chiral form, preferably the S isomer of the formula:

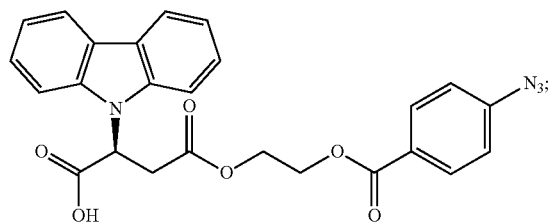 [SMILES: [N-]=[N+]=Nc1ccc(C(=O)OCCOC(=O)C[C@@H](C(=O)O)n2c3ccccc3c3ccccc32)cc1]

and (iv) 5-(2-(4-azidobenzoyloxy)ethoxy)-2-(9H-carbazol-9-yl)-5-oxopentanoic acid, in its racemic or chiral form, preferably the S isomer of the formula:

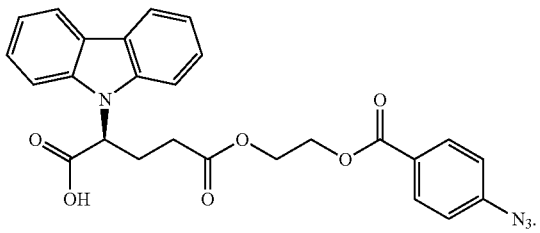 [SMILES: [N-]=[N+]=Nc1ccc(C(=O)OCCOC(=O)CC[C@@H](C(=O)O)n2c3ccccc3c3ccccc32)cc1]

In certain embodiments, the present invention relates to surface-modified polymer films, wherein the surface of said polymer is modified by the covalent binding of nano- or micro-particles of a hybrid organic-inorganic oxide network comprising a photoreactive species. In certain embodiments, the inorganic oxide is selected from, but not limited to, $SiO_2$, $TiO_2$, $Al_2O_3$, $ZrO_2$, $SeO_2$, and $SeO_3$. In some preferred embodiments, the inorganic oxide is silica ($SiO_2$). The photoreactive or photoactivatable reagent or species (the terms 'reagent' and 'species' are used herein interchangeably) is a UV-activated reagent as defined above and is, in certain embodiments, a simple aryl azide, a fluorinated aryl azide, a diaryl ketone, a fluorinated aziridine, or a fluorinated aryl aziridine. The inotganic oxide moiety and the photoreactive moiety are linked through an aliphatic chain comprising at least one divalent radical such as —O—CO—, —CO—O—, —NH—CO—, —CO—NH—, —CH=CH—, —C≡C— and —O—Si—O—, said at least one divalent radical being attached to the photoreactive group.

In certain embodiments, the hybrid photoreactive organic-inorganic oxide network is composed of molecules of the formula II:

wherein

Z is an inorganic oxide comprising a group capable of reacting with a nucleophile;

Y is a divalent radical;

B is a moiety of a photoreactive reagent;

n is an integer from 1 to 10; and n' is an integer from 1 to 3.

In certain embodiments, the surface of the polymer film is modified by a compound of formula II, wherein:

Z is an inorganic oxide selected from the group consisting of $SiO_2$, $TiO_2$, $Al_2O_3$, $ZrO_2$, $SeO_2$, and $SeO_3$ and the group capable of reacting with a nucleophile is OH or OR, wherein R is alkyl or aryl;

B is a photoreactive moiety derived from an aryl azide, a diaryl ketone, a fluorinated aziridine or a fluorinated aryl aziridine;

Y is a divalent radical selected from the group consisting of —O—CO—, —CO—O—, —NH—CO—, and —CO—NH—;

n is 1 to 6; and n" is 1, 2 or 3.

In certain preferred embodiments, in the compound of formula II the inorganic oxide is $SiO_2$, Y is —NH—CO—, B is a moiety derived from phenyl azide, tetrafluorophenyl azide or benzophenone; n is 2 to 4, preferably 3, and n' is 1.

Examples of compounds of formula II wherein Z is silica include, but are not limited to, the compounds of the following structures:

(i)

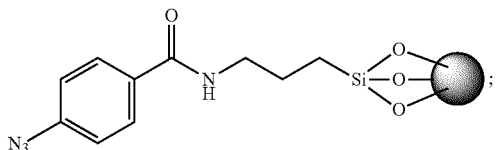

(ii)

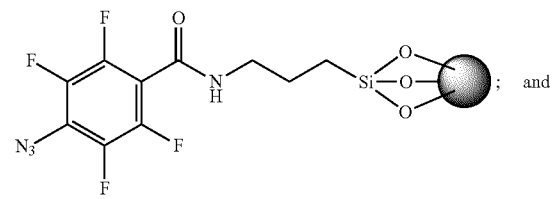

; and

-continued (iii)

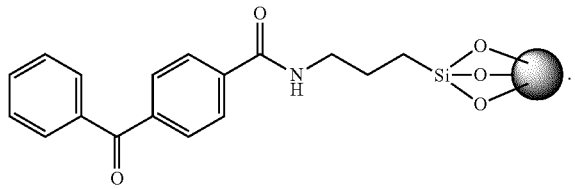

According to the invention, one, two, or more photoreactive moieties can be attached to the inorganic oxide/silica core. Additional moieties attached to the silica via silanol chemistry attachment provide better reactivity.

In some embodiments, the present invention provides a novel surface-modified polymer film, wherein the polymer is parylene C and the surface thereof is modified by chemical functionalization with nano- or microparticles of a bifunctional polymer comprising a photoreactive species obtained by polymerization of a monomer of the formula I above. In certain embodiments, the chemically reactive functional group is carboxyl, A is a moiety derived from a carbazole, the linker Y is —NH—CO— and the linker Y' is absent, or Y is —CO—O— and Y' is O—CO—; the photoreactive species B is a moiety of an aryl azide selected from the group consisting of phenyl azide, tetrafluorophenyl azide, hydroxyphenyl azide, and nitrophenyl azide; or a moiety of a diaryl ketone selected from the group consisting of unsubstituted benzophenone and benzophenone substituted by one or more carboxyl, azido, amino or hydroxy groups; n is 1, 2, 4 or 6; and m is 0, 2 or 4.

In certain embodiments, the present invention provides a surface-modified parylene C film, wherein the surface of said parylene film is modified by covalent binding of nano- or micro-particles of a hybrid organic-inorganic oxide network comprising a photoreactive species, for example, of the formula II above, wherein the inorganic oxide represented by Z may be $SiO_2$, $TiO_2$, $Al_2O_3$, $ZrO_2$, $SeO_2$, or $SeO_3$; the photoreactive moiety represented by B is derived from an aryl azide, a diaryl ketone, a fluorinated aziridine or a fluorinated aryl aziridine; and the linker Y is a divalent radical selected from —O—CO—, —CO—O—, —NH—CO—, or —CO—NH—. In certain preferred embodiments, the inorganic oxide is $SiO_2$, Y is —NH—CO—, B is a moiety derived from phenyl azide, tetrafluorophenyl azide or benzophenone; n is 2 to 4, and n' is 2 or 3.

In another aspect, the present invention provides a polymerizable monomer comprising a photoreactive species and a chemically reactive functional group, said monomer being of the formula I as defined above. In some preferred embodiments, in the polymerizable monomer of formula I, the chemically reactive functional group is carboxyl, A is a moiety derived from a carbazole; the linker Y is —NH—CO— and Y' is absent, or Y is —CO—O— and Y' is O—CO—; the photoreactive group B is a moiety of an aryl azide selected from the group consisting of phenyl azide, tetrafluorophenyl azide, hydroxyphenyl azide, and nitrophenyl azide; or a moiety of a diaryl ketone selected from the group consisting of unsubstituted benzophenone and benzophenone substituted by one or more carboxyl, azido, amino or hydroxy groups; n is 1, 2, 4 or 6; and m is 0, 2 or 4.

In certain embodiments, the polymerizable monomer is a compound selected from the compounds:
(i) 6-(4-benzoyl-benzoylamino)-2-carbazol-9-yl-hexanoic acid, in its racemic or chiral form, preferably the S isomer;
(ii) 6-(4-azido-benzoylamino)-2-carbazol-9-yl-hexanoic acid, in its racemic or chiral form, preferably the S isomer;
(iii) 4-(2-(4-azidobenzoyloxy)ethoxy)-2-(9H-carbazol-9-yl)-4-oxobutanoic acid in its racemic or chiral form, preferably the S isomer; and
(iv) 5-(2-(4-azidobenzoyloxy)ethoxy)-2-(9H-carbazol-9-yl)-5-oxopentanoic acid, in its racemic or chiral form, preferably the S isomer.

In another aspect, the present invention relates to a (co)polymer obtained by (co)polymerization of monomers of the formula I above. In certain embodiments, the polymer is obtained by polymerization of a sole monomer of formula I. In certain other embodiments, the copolymer is obtained by copolymerization of two or more monomers of formula I.

In another aspect, the present invention relates to micro- or nano-particles made of a (co)polymer of formula I.

In a further aspect, the present invention relates to a hybrid organic-inorganic oxide network comprising a photoreactive species. In certain embodiments, the hybrid photoreactive organic-inorganic oxide network is composed of molecules of the formula II herein, wherein the inorganic oxide represented by Z may be $SiO_2$, $TiO_2$, $Al_2O_3$, $ZrO_2$, $SeO_2$, and $SeO_3$, preferably silica; the photoreactive species represented by B may be derived from an aryl azide, a diaryl ketone, a fluorinated aziridine or a fluorinated aryl aziridine, and the linker Y is a divalent radical selected from —O—CO—, —CO—O—, —NH—CO—, and —CO—NH—. In some preferred embodiments, the inorganic oxide is $SiO_2$, Y is —NH—CO—, B is a moiety derived from phenyl azide, tetrafluorophenyl azide or benzophenone; n is 2 to 4, and n' is 2 or 3.

Examples of said hybrid photoreactive organic-inorganic oxide of the formula II include the compounds:

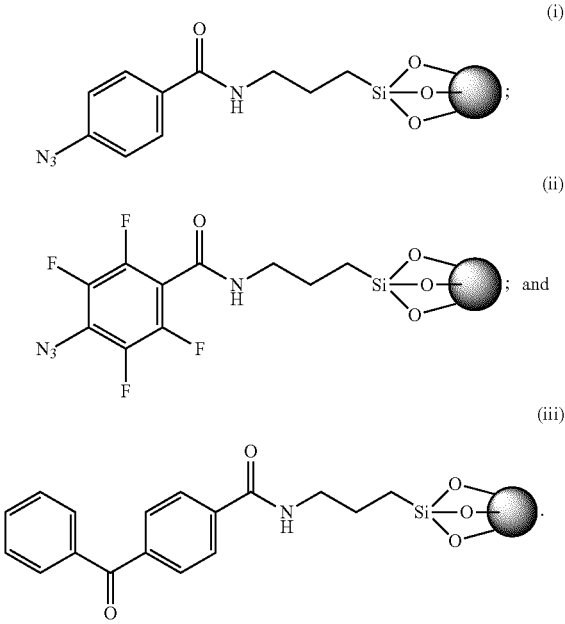

In certain embodiments a sole photoreactive moiety is attached to the inorganic oxide, e.g., silica, core. In certain other embodiments, in order to achieve a better reactivity, two or more photoreactive moieties are attached to the inorganic oxide, e.g., silica, core.

The present invention further provides micro- or nano-particles made of a hybrid photoreactive organic-inorganic oxide network of formula II herein. In certain embodiments, the particles are nanoscaled particles.

As defined herein, any alkyl group may contain 1-10 carbon atoms, preferably 1-6, more preferably 1-4, carbon atoms. The term 'aryl' denotes an unsubstituted pheny group or a phenyl group substituted by alkyl, alkoxy, halogen, nitro, and the like.

The polymeric films according to the invention are thin polymeric films of a thickness in the range of 0.2 to 10 μm, preferably 1, 2, 3, 4 or 5 μm.

The microparticles according to the invention are particularly microspheres of about 0.25-5 μm range for average diameters. The polycarbazole-based particles according to the invention are in general microspheres.

The nanoparticles according to the invention have from 30 nm to 300 nm in average diameters. The silica-based particles according to the invention are in general nanoparticles.

The novel photoreactive carbazole (Cbz)-based monomers of formula I according to the invention can be prepared as depicted in Schemes 1-4 (depicted hereinafter just before the Claims) and described in detail in Examples 1-4. Thus, Scheme 1 depicts the multi-step synthesis of Compound 7, (S) 6-(4-benzoyl-benzoylamino)-2-carbazol-9-yl-hexanoic acid, the photoreactive carbazole (Cbz)-based oxidizable monomer of formula I wherein the oxidizable group is carbazole, the moiety of the chemically reactive group is OH, the linker Y is —HN—CO—, Y' is absent, the photoreactive moiety is benzophenone, n is 4 and m is 0. Compound 7 was obtained as a white solid in 98% yield. As shown in Example 1 and Scheme 1, protected L-Lys(Z)—OMe (1) is reacted with 2,4-dimethoxytetrahydrofuran (DMTHF) to give (S)-methyl 6-benzyloxycarbonylamino-2-carbazol-9-yl-hexanoate (3), followed by the removal of the benzyloxycarbonyl protecting group with 10% Pd/C to give (S)-6-amino-2-carbazol-9-yl-hexanoic methyl ester (4), In order to obtain (S)-6-(4-benzoyl-benzoylamino)-2-carbazol-9-yl-hexanoic acid methyl ester (6), compound 4 is reacted with 4-benzoyl benzoic acid (5) either by method A, which involves reaction in the presence of carbonyldiimidazole (CDI), or by method B in the presence of $PCl_5$. The desired monomer 7 was obtained by refluxing under methanolic KOH, followed by neutralization to pH 3-4. Scheme 2 and Example 2 and show the synthesis of the Compound 14, (S)-6-(4-azido-benzoylamino)-2-carbazol-9-yl-hexanoic acid, the monomer of formula I wherein the oxidizable group is carbazole, the moiety of the chemically reactive group is OH, the linker Y is —HN—CO—, Y' is absent, the photoreactive moiety is 4-azido phenyl, n is 4 and m is 0, starting from 4-aminobenzoic acid and resulting in 88% yield of monomer 14. Scheme 3 and Example 3 describe the synthesis of Compound 20, (S)-4-(2-(4-azidobenzoyloxy)ethoxy)-2-(9H-carbazol-9-yl)-4-oxobutanoic acid, the monomer of formula I wherein the oxidizable group is carbazole, the moiety of chemically reactive group is OH, the linker Y is —CO—O—, Y' is —O—CO—, the photoreactive moiety is 4-azido phenyl, n is 1 and m is 2, starting from H-Asp-O-benzyl. Scheme 4 and Example 4 show the synthesis of Compound 26, (S)-5-(2-(4-azidobenzoyloxy)ethoxy)-2-(9H-carbazol-9-yl)-5-oxopentanoic acid, the monomer of formula I wherein the oxidizable group is carbazole, the moiety of chemically reactive group is OH, the linker Y is —CO—O—, Y' is —O—CO—, the photoreactive moiety is 4-azido phenyl, n is 2 and m is 2, starting from H-Glu-O-benzyl. Other compounds of formula I can be obtained in similar manner starting from the appropriate starting compounds.

A Cbz-based polymer according to the invention is obtained by polymerization of monomers of formula I. The novel polymeric photoreactive polyCbz-based particles of the invention are prepared from the corresponding monomer by reacting the monomer with a strong oxidizing agent such as ammonium persulfate $(NH_4)_2S_2O_8$.

The photo-functionalization of parylene films with poly-Cbz-based micro- or nano-particles according to the invention can be performed by spotting a solution of the polyCbz-based particles on a parylene film deposited on a solid quartz or glass support, evaporating the solvent and UV irradiating the film.

Due to the well-known hydrophilicity and biocompatibility of silica nanoparticles, their covalent attachment to parylene films would allow the obtainment of fully biocompatible coatings and thus solve the drawbacks mentioned above for parylene films. Moreover, silica nanoparticles can be used as a platform for a wide range of $2^{nd}$ step derivatization functionalities using silane-based chemistry.

Monodisperse, colloidal silica nanoparticles (NPs) prepared according to Stöber method (Stöber et al., 1968) were carefully investigated during the last four decades. There are two basic approaches for the covalent introduction of chemical functionalities to silica NPs: surface silanization and co-condensation methods. The silanization method to produce functional silica NPs was first reported in 1989 by Philipse and Vrij and now frequently used in various fields of chemistry. In 1993 Blaaderen and Vrij published the original paper that demonstrated the new concept of introducing chemical functionalities to silica NPs by co-condensation of tetraethyl orthosilicate (TEOS) and appropriate organosilane, yielding stable hybrid organo-silica NPs. Using the co-condensation method, a variety of chemical functionalities were introduced into silica NPs, for example, amine (Blaaderen and Vrij, 1993), fluorescent dyes (Blaaderen and Vrij, 1992), carbazole (Peled et al., 2009), alkyne (Lu et al., 2009), and atom transfer radical polymerization (ATPR) initiator (Radhakrishnan et al., 2008). However, extensive literature survey showed that only one work described the preparation of photoreactive $SiO_2$ NPs by surface silanization with perfluorinated phenyl azide (PFPA)-silane (Gann and Yan, 2008).

Photochemistry is a very effective tool for the formation of highly reactive species that can react with inert materials. Upon UV irradiation, photoreactive groups such as benzophenone (BPh), phenyl azide (PA), and PFPA moieties are known to generate highly reactive species, i.e., nitrenes (from PA and PFPA) or excited triplet BPh moieties (from BPh). These highly reactive species readily react with C—H and C=C bonds of any organic matter via insertion or abstraction mechanisms (Braeuchle et al, 1981; Patai, 1971).

According to the present invention, novel hybrid photoreactive silica NPs (denoted as $SiO_2$@photoreactive group) are prepared by co-condensation of photoreactive organosilanes and TEOS to obtain $SiO_2$@PA and $SiO_2$@BPh NPs. According to Gann and Yan (2008) mentioned above, PA-based organosilanes cannot be used because of potential tendence of PA to give ring expansion products, i.e. dehydroazepine, in the presence of nucleophiles. For this reason, we have synthesized $SiO_2$@PFPA NPs and compared their reactivity to $SiO_2$@PA. The reactivity of these three types of photoreactive silica NPs was evaluated by their covalent immobilization into highly chemically stable poly(2-chloro-paraxylylene) (parylene C) films. It was found that, in contrast to what is stated in the literature, PA is much more reactive than PFPA, when dealing with solid state photochemical reactions.

In summary, two types of novel PA or BPh-based highly photoreactive silica nanoparticles were prepared and their reactivity was compared to that of PFPA-based $SiO_2$ nanoparticles. The reactivity evaluation was carried out by the reaction of the three types of $SiO_2$ nanoparticles with highly inert PC films. It was found, that in contrast to what was stated in the literature, $SiO_2$@PA nanoparticles are much more reactive than $SiO_2$@PFPA ones when dealing with the solid state photochemical reactions described above. Moreover, this is the first report of covalent immobilization of nanoparticles into biocompatible PC films to form hydrophilic and functional composite films. Since, silica nanoparticles are known to be biocompatible and PC is used for coating of biomedical devices, these improved composite films may have versatile applications in the medical field.

A further aspect of the present invention relates to a second step functionalization of the surface-modified/functionalized parylene films of the invention. Both the photoreactive polyCbz polymeric particles and hybrid silica inorganic nanoparticles enable the second step derivatization.

The polyCbz-based microspheres of the invention can be subjected, for example, to the oxidative growth of another layer of conducting polymers (CPs) of the type polypyrrole, polycarbazole, polyaniline and polythiophene and their combinations using the concept of "growth from the surface". Previously, we have found that hybrid silica nanoparticles bearing carbazole groups on their surfaces can be prepared using a carbazole-based silane incorporated into silica nanoparticles (Peled et al., 2008) through the well known Stöber sol-gel method (Stoeber et al., 1968). These functional hybrid silica NPs were prepared in a facile one pot synthesis and the carbazole groups present on their surface acted as polymerization anchors for bulk carbazole monomer during the polymerization/growth of a carbazole-shell over the silica-core. In a similar manner, in a second step, surface-localized heterocyclic carbazole groups of the modified surface of a parylene film of the invention can act as nucleophilic attachment species towards a polyCOOH carbazole polymer adlayer generated oxidatively.

It is also possible, according to the invention, to exploit the versatile polyCOOH chemistry introduced after particle attachment in order to perform diimide-mediated coupling of bifunctional substrates like diamines, amino-alcohols, thio-alcohols, thio-amines, and the like.

With the parylene films modified in the surface by photoreactive hybrid silica nanoparticles, the second step derivatization is even simpler since the whole wide silicate chemistry is opened for $2^{nd}$ step film functionalization using difunctional silicates of the type $(EtO)_3Si$-linker-X, wherein X is a functional group such as SH, $NH_2$, COOH, OH, etc. Thus the silica functionalized parylene C films of the invention are used as an intermediate functional phase for a second modification step using silane-based chemistry. A successful incorporation of amine functionality onto silica NPs was achieved by their reaction with 3-aminopropyltriethoxysilane (APTES), incubated with fluorescent tag and studied by fluorescence microscopy. This strategy provides a general and versatile route to efficient functionalization of silica by light.

Thus, according to the invention, an innovative way to photochemically functionalize polymeric films has been developed and successfully implemented using a wide range of polymeric polyCOOH (polycarbazole) microspheres and inorganic hybrid silica ($SiO_2$) nanoparticles. Such a generic approach for polymeric film coatings functionalization and 2D-coating structuration demonstrated effective applications in the field of typical non-functional biocompatible parylenes films of wide use in the biocompatible implant and electronic industries. Beyond the well-detailed characterization aspect dealing with resulting particulate-modified polymer coatings as mentioned below, this invention provides a general approach and solution to the long-lasting challenging issue of taylored functionalization of any desired polymeric coating due to the readily and effective potential for $2^{nd}$ step surface derivatization. As typical illustrative examples, both types of polymeric polyCbz- and hybrid inorganic silica particulate systems lead to film coating $2^{nd}$ step derivatizations using both versatile diimide (polyCOOH activation-derivatization) and silicate (Si—OH chemical derivatization) chemistries.

The preparation of composite parylene/nanoparticles films according to the invention can have many advantages, because this approach allows the incorporation of both new chemical and physical properties. It is important to mention that the bonding between the film and the particles should be covalent for medical applications in order to avoid degradation or uncontrolled release of the composite with time.

The present invention uses a quite versatile and general approach based on surface structuration and modification mediated by various UV-reactive polymeric and non-polymeric inorganic particles. Moreover and beyond the full characterization of such modified polymeric coatings, this invention provides proof of evidence that the added functionality can be further derivatized towards multi-layered functional coatings.

The invention will be illustrated without limitation by the following examples.

EXAMPLES

Abbreviations: AFM, atomic force microscopy; APTES, (3-aminopropyl)triethoxysilane; BPh, benzophenone; Cbz, carbazole; CDI, 1,1'-carbonyldiimidazole; CP-MAS, cross polarization-magic angle spinning; DCC, N,N'-dicyclohexylcarbodiimide; DCU, dicyclohexylurea; DLS, dynamic light scattering; DMAP, para-dimethylaminopyridine; DMSO, dimethylsulfoxide; DSS, 4,4-dimethyl-4-silapentane-1-sulfonic acid; ESEM, environmental scanning electron microscope; EtOH, ethanol; FIB, focused ion beam; FTIR, fourier transform infrared spectroscopy; HRMS, high resolution mass spectra; NMR, nuclear magnetic resonance; NPs, nanoparticles; PA, phenyl azide; PATES, PA-based triethoxysilane; PFPA, perfluorinated PA; PFPATES. PFPA-based triethoxysilane; RT or rt, room temperature; SEM, scanning electron microscope; $SiO_2$@photoreactive group, hybrid photoreactive silica NPs; ssNMR, solid state nuclear magnetic resonance; TEOS, tetraethyl orthosilicate; TES, triethoxysilane; THF, tetrahydrofurane; TMS, tetramethylsilane; TEM, transmission electron microscopy; UV, ultraviolet; XPS, X-ray photoelectron spectroscopy.

Materials and Methods

All reagents were obtained commercially from sigma-Aldrich unless otherwise noted. 4-azidobenzoic acid and 4-azido-2,3,5,6-tetrafluorobenzoic acid were prepared according to a literature procedure (Keana et al., J. Org. Chem. 1990, 55, 3640-3647; and Pinney et al., J. Org. Chem. 1991, 56, 3125-3133, respectively).

Chromatographic purification of products was accomplished using flash chromatography on MERCK silica gel 60 (0.040-0.063, 230-400 mesh ASTM). RT (or rt) refers to 20-22° C.

(i) General Procedure for the Formation of Polymeric PolyCbz-Based Particles

The corresponding monomer (0.25 mmol) was taken in 2.5 mL of acetone in a scintillation vial, and vortexed for a short period for dissolution (~1 min, rt). Bi-distilled water (2.5 mL) was added to the monomer solution followed by the ammonium persulfate (APS) oxidant [$(NH_4)_2S_2O_8$, 0.625 mmol]. The solution was vortexed for a short period (1.0 min) after each addition. Then, the reaction mixture was stirred (1 h at 15° C.), centrifuged (10,000 rpm, 10 min, 4° C.), and the resulting yellow-brown precipitate washed with a 1/1 v/v acetone/water mixture (3×10 mL) using sequential vortex redispersion-centrifugation steps. Finally, the poly(dicarbazole-lysine) (DCL)-based nanoparticle (NP) precipitate was dissolved in acetone (5 mL) in order to take a sample for SEM and UV absorption analysis. The rest of the sample was evaporated and the leftovers of water were lyophilized overnight. The particles were readily characterized by SEM, HR-SEM, EDS linescan analysis, elemental analysis (EA), and FT-IR.

(ii) General Procedure of Photo-Functionalization of Parylene Films:

Corresponding polyCbz-based nanoparticles in an acetone solution were spotted on 2 μm-thick parylene film deposited on a solid quartz or glass support. The solvent was allowed to evaporate and the film was placed in a glass tube degassed with Argon and irradiated by a medium-pressure UV lamp (Phillips HPK 125w) at 15° C. (cooler temperature) for 6 h. After irradiation, the film was placed in $CH_2Cl_2$ for a few hours and then sonicated in a Bransonic ultrasound cleaning bath (42 KHz at full power) for 10 min. The film was then dried in air and kept protected from light.

(iii) General Synthesis of Photoreactive Hybrid Silica Nanoparticles (NPs)

Hybrid silica NPs were prepared according to a Stöber method with some modifications.

A photoreactive silane (27 or 28 or 29) (0.76 mmol) was added to a solution of tetraethyl orthosilicate (TEOS) (1.55 mL, 6.84 mmol) in EtOH (45 ml) under vigorous stiffing at RT. Then water (2.75 mL) and $NH_4OH$ 28% (1.2 mL) were added to the reaction. The reaction was allowed to proceed for 6 h under vigorous stirring at RT. The NPs were isolated by centrifugation (15000 rpm, 0° C., 20 min). The supernatant was removed and NPs were redispersed in ethanol (30 ml) using bath sonicator. The re-dispersion centrifugation washing was repeated 5 times. The purified silica NPs were divided in 2 vials. One part was evaporated and dried in vacuum oven overnight (30° C.) to remove solvents. The second part was homogeneously dispersed in ethanol and stored in dark in fridge. In order to determine the NP concentration in solution, 1 mL of NP dispersion was evaporated and dried in vacuum oven overnight (30° C.) to remove solvents. Thus all dispersions were diluted with EtOH to achieve 9 mg/mL NP dispersions.

The bare silica NPs were prepared by the same procedure using TEOS (1.7 mL, 7.6 mmol) without addition of photoreactive silane.

(iv) Functionalization of Parylene C Films with Photoreactive $SiO_2$ NPs

4 μm-thick parylene C films deposited on a glass substrate (7×7 mm) using a chemical vapor deposition (CVD) method were generously supplied by COMELEC SA Ltd. (Switzerland). The films were pre-washed for 3 times in EtOH (10 mL) using a Bransonic cleaner bath sonicator for 10 min and dried under vacuum at 30° C. for 2 h. 20 μL of ethanolic dispersions (9.0 mg/mL) of the corresponding hybrid photoreactive $SiO_2$ NPs or bare $SiO_2$ NPs were spin coated (2 min, 1500 rpm, $N_2$ atmosphere) on the parylene C films and the films were UV irradiated under argon atmosphere for 4 h. After irradiation, the films were washed 3 times in EtOH (10 mL) using a Bransonic cleaner bath sonicator for 10 min and dried under vacuum at 30° C. overnight.

(v) General Procedure for Post Modification of PC—$SiO_2$@Photoreactive Group Films with APTES The three types of $SiO_2$ modified films, as well as PC—$SiO_2$ film, were shacked in a (EtOH/$H_2O$/APTES 2.50 mL/2.50 mL/10.0 μL) solution for 24 h at RT. The amino-modified films were peeled from the glass support, vigorously washed with EtOH and dried under air. The self-supported amino-modified films were immersed into a solution (1.0 mg/mL) of dansyl chloride in anhydrous DMF for 1 h. Finally, films were vigorously washed with DMF and dried under flow of argon.

Chemophysical Procedures

NMR spectra were recorded on a Bruker DRX spectrometer (300 MHz, 75.5 MHz for $^1H$, $^{13}C$ respectively), and are referenced internally according to TMS (0 ppm) or relative to the solvent. Data for $^1H$-NMR are recorded as follows: chemical shift (δ in ppm), multiplicity (s, singlet; br, broad signal; d, doublet; t, triplet; q, quartet; m, multiplet), coupling constant (Hz)), and integration. Data for $^{13}C$-NMR are reported in terms of chemical shift (δ in ppm).

HRMS were run on a VG-Fison AutoSpec Premier High Resolution Spectrometer, manufactured by Waters (UK).

FTIR spectra were recorded on a Bruker TENSOR 27 spectrometer using Diffuse Reflectance Accesory EasyDiff (PIKE technologies). Samples were prepared by mixing material (2%) with KBr (dry, IR grade KBr, Aldrich). The spectra that are obtained by the diffuse reflection technique appear different from standard transmission spectra. The peak intensities at high wave numbers are weak and the peak line shapes are rounded. In order to compensate these differences the spectra were transformed into Kubelka Munk units using FTIR software.

UV absorbance spectra were recorded on Varian CARY 100 Bio UV-Visible spectrophotometer. The spectra were obtained in ethanol.

DLS and ζ-potentials measurements were performed using Malvern zeta sizer nano series Nano ZS using ethanolic dispersions of nanoparticles.

TGA was carried out on a TA Instruments apparatus (1GA Q500 model) using a 25-800° C. temperature profile (10° C./min, $N_2$ atmosphere, 100 mL/min).

TEM images were taken on 120 kV FEI, Tecnai G12 BIOT-WIN. Samples were prepared on formvar/carbon 400 mesh Cu grids by dropping an etanolic solution of the particles.

Solid state $^{13}C$ and $^{29}Si$ CP-MAS NMR were recorded on a Bruker 500 instrument equipped with a 4 mm solid state probe operating at 125 MHz for $^{13}C$ and 500 MHz for $^{29}Si$ nuclei. Chemical shifts were referenced to external samples of DSS ($^{29}Si$) and adamantane ($^{13}C$). The $^{13}C$ signal was enhanced using cross polarization techniques, where $^1H$ polarization is transferred to the $^{13}C$ nuclei. The presented spectra were collected using a magic angle spinning rate of 8 kHz.

For the $^{13}C$ a contact time of 3 ms was applied, with a 2.83 μs pulse, a recycle delay of 2 s and line broadening of 60 Hz. For the $^{29}Si$ spectra a contact time of 5 ms was applied, a pulse length of 2.7 μs was used, with a delay time of 5 s and line broadening of 100 Hz.

AFM measurements and imaging were carried out using a Nanoscope V Multimode scanning probe microscope (Digital Instruments, Santa Barbara, Calif.). All images were obtained using the tapping mode with a single LTESP siliconprobe (force constant of 48 N/m, Digital Instruments, Santa Barbara, Calif.). The resonance frequency of this cantilever was approximately 130-250 kHz. The scan angle was maintained at 90°, and the images were captured in the retrace direction with a scan rate of 0.5/1 Hz (respectively for the scan size 10000×10000 nm/2000×2000 nm). The aspect ratio was 1:1 and image resolution 512 samples/line. Before analysis of the images, the "flatting" and "planefit" functions were applied to each image.

Gwyddion Software was used for image processing.

SEM images were taken on PEI, QUANTA 200 F or Helios 600. Samples were prepared on Cu palets by gluing the glass supported parylene C films on double side carbon tape and coating them with gold.

XPS analysis was performed on Thermo-VG SIGMA probe.

Contact angle values were measured using a Rame-Hart Model 100 Contact Angle Goniometer.

UV irradiations were performed using Phillips HPK 125w UV lamp.

Spin coatings were performed using "Specialty Coatings Systems" P6700 spin coater. 20 µL of ethanolic dispersions (9 mg/ml) of the corresponding hybrid photoreactive silica NPs or bare $SiO_2$ NPs were spin coated (2 min, 1500 rpm, N2 atmosphere) on the parylene C films.

Example 1

Synthesis of (S) 6-(4-Benzoyl-benzoylamino)-2-carbazol-9-yl-hexanoic acid (7)

The total multi-step synthesis of photoreactive carbazole (Cbz) based oxidizable monomer (S) 6-(4-Benzoyl-benzoylamino)-2-carbazol-9-yl-hexanoic acid 7 is depicted in Scheme 1.

1.1 Synthesis of (S)-methyl 6-benzyloxycarbonylamino-2-carbazol-9-yl-hexanoate (3)

A vigorously stiffed solution of L-Lys(Z)—OMe (3.31 g, 10 mmol) in acetic acid (20 mL) and dioxane (40 mL) was heated to 75° C., at this temperature 2,5-dimethoxytetrahydrofuran (DMTHF, ee 97%) (3.97 g, 3.90 mL, 30 mmol) was added dropwise to the reaction mixture. After complete addition of DMTHF, the reaction mixture was refluxed at 110° C. for 3 h followed by 5-6 h stiffing at room temperature. The volatiles were removed under reduced pressure to afford a dark brown residue, which was dissolved in dichloromethane (100 mL) and washed with 10% $NaHCO_3$ solution (15 mL), brine (15 mL) and water (15 mL). The organic phase was dried over anhydrous $Na_2SO_4$ and evaporated under reduced pressure. The residue was purified by flash chromatography on silica gel (230-400 mesh) using hexane:ethyl acetate (7:3) as eluent to afford (S)-methyl 6-benzyloxycarbonylamino-2-carbazol-9-yl-hexanoate 3 (1.10 g, 25%) as a pale yellow solid.

Pale yellow solid, mp: 97-99° C., FT-IR (KBr, cm$^{-1}$): 3411, 3315 ($v_{O-H}$, $v_{N-H}$), [3056, 2945, 2864] ($v_{C-H\ stretching}$), 1730 ($v_{C=O\ ester}$), 1638 ($v_{C=O\ amide}$), [1596, 1522, 1487, 1451] ($v_{C=C}$), 1337 ($v_{C-H\ bending}$), 1240 ($v_{C-O}$), 1165, 1131, 1019, 749 ($v_{C=C-H}$); $^1$H NMR (CDCl$_3$, 300 MHz): δ 8.08 (d, 2H, J=7.8 Hz, ArH), 7.45-7.21 (m, 11H, ArH), 5.2 (t, 1H, J=7.5 Hz), 5.01 (s, 2H), 4.56 (bs, 1H, NH), 3.63 (s, 3H), 3.01-2.99 (m, 2H), 2.39 (q, 2H, J=15.0, 7.5 Hz), 1.43-1.18 (m, 3H), 1.03-0.99 (m, 1H); $^{13}$C NMR (CDCl$_3$, 75 MHz): 171.14, 156.37, 139.98, 136.67, 128.60, 128.18, 125.99, 123.42, 120.55, 119.63, 109.45, 66.67, 56.79, 52.68, 40.60, 29.48, 29.27, 23.38; MS (DCI, CH4): m/z 444 (100%, [M]$^+$), 324 (16.6%), 277 (16.2%, [M-carbazol]$^+$), 167 (12.2%, [carbazol]$^+$), 91 (46.4%, [PhCH$_2$]$^+$); HR-MS (DCI, CH4) m/z calcd for $C_{27}H_{28}N_2O_4$ [M]$^+$ 444.2049. Found 444.2040.

1.2 Synthesis of (S)-6-Amino-2-carbazol-9-yl-hexanoic methyl ester (4)

10% Pd/C (0.100 g) was added in one portion to a stiffed solution of (S)-Methyl 6-benzyloxycarbonylamino-2-carbazol-9-yl-hexanoate 3 (1.06 g, 2.47 mmol) in a (1:1) mixture of THF (10 mL) and isopropanol (10 mL) under nitrogen atmosphere. The reaction mixture was subsequently stirred under hydrogen atmosphere for 4 h at room temperature. The reaction mixture was filtrated through a celite pad and the filtrate was evaporated under reduced pressure to get (S)-6-amino-2-carbazol-9-yl-hexanoic methyl ester 4 (0.640 g, 85%) as off-white solid.

Off-white solid, mp: 175° C., FT-IR (KBr, cm$^{-1}$): 3428 ($v_{N-H}$), [3053, 2941, 2859] ($v_{C-H}$ stretching), 1739 ($v_{C-O}$, ester), [1593, 1451, 1386] ($v_{C=C}$), 1338 ($v_{C=H,\ bending}$), 1213 ($v_{C-O}$), 1153, 1017, 870, 755 ($v_{C=C-H}$); $^1$H NMR (CDCl$_3$, 300 MHz): δ 8.11 (d, 2H, J=7.8 Hz, ArH), 7.48-7.38 (m, 4H, ArH), 7.29-7.24 (m, 2H, ArH), 5.24 (t, 1H, J=7.8 Hz), 3.65 (s, 3H), 2.50-2.37 (m, 4H), 1.73 (bs, 2H, NH$_2$), 1.41-0.98 (m, 4H); $^{13}$C NMR (CDCl$_3$, 75 MHz): 171.64, 140.42, 126.33, 123.81, 120.90, 119.96, 109.89, 57.28, 53.04, 41.99, 33.33, 29.92, 23.95; MS (DCI, CH4): m/z 310 (33.5%, [M]$^+$), 277 (15.2%), 251 (6.7%, [M-CO$_2$Me]$^+$), 167 (100%, [carbazol]$^+$); HR-MS (DCl, CH4) m/z calcd for $C_{19}H_{23}N_2O_2$ [MH]$^+$ 311.1759. Found 311.1799.

1.3 Synthesis of (S)-6-(4-Benzoyl-benzoylamino)-2-carbazol-9-yl-hexanoic acid methyl ester (6)

1.3.1 Method A

Carbonyldiimidazole (0.162 g, 1.0 mmol) was added to a solution of 4-benzoyl benzoic acid (0.226 g, 1.0 mmol) in dry THF (10 mL) under nitrogen atmosphere at room temperature and the resulting mixture was stirred for 1 h at the same conditions. Then, (S)-methyl 6-amino-2-carbazol-9-yl-hexanoate 4 (0.310 g, 1.0 mmol) in dry THF (5 mL) was added dropwise by syringe into the reaction mixture. The reaction mixture was allowed to stir for additional 3 h at room temperature. After completion of the reaction (monitored by TLC), the solvent was removed under reduced pressure and the crude product was dissolved in ethyl acetate (50 mL) washed with brine (20 mL×2), and finally dried over anhydrous Na$_2$SO$_4$. Filtration followed by removal of the solvent under reduced pressure provided a gummy colorless residue, which was purified by column chromatography over silica gel using dichloromethane:methanol (98:2) as eluent to afford (S)-6-(4-benzoyl-benzoylamino)-2-carbazol-9-yl-hexanoic acid methyl ester 6 (0.290 g, 56%) as a white solid.

1.3.2 Method B

PCl$_5$ was added to a stirred solution of 4-benzoyl benzoic acid (0.226 g, 1.0 mmol) in 10 mL of CHCl$_3$ (0.218 g, 1.05 g mmol) at 0° C. The reaction mixture was stirred at room temperature for 45 min. After complete conversion of starting acid the solvent was removed under reduced pressure to afford white solid (acid chloride) which was used directly for next step of amidation reaction without further purification.

The acid chloride in CHCl$_3$ (5 mL) was added dropwise to a well-stirred solution of amine, (S)-methyl 6-amino-2-carbazol-9-yl-hexanoate 4 (0.318 g, 1.03 mmol) in dry chloroform (10 mL) and dry Et$_3$N (0.40 mL, 2.88 mmol) under nitrogen atmosphere at 0° C. The reaction mixture was stirred for 1 h at room temperature until the amine was consumed. Evaporation of the volatiles under reduced pressure gave a residue, which was purified by flash column chromatography over silica gel (230-400 mesh) using dichloromethane: methanol (98:2) as eluent to obtain (S)-6-(4-benzoyl-benzoylamino)-2-carbazol-9-yl-hexanoic acid methyl ester (6) (0.340 g, 66% from two step) as a white solid. White solid, mp: 65° C.; FT-IR (KBr, cm$^{-1}$): 3284 ($v_{N-H}$), [3058, 2939, 2862] ($v_{C-H\ stretching}$), 1738 ($v_{C=O\ ester}$), 1656 ($v_{C=O}$), 1630 ($v_{C=O\ amide}$), [1547, 1486, 1452] ($v_{C=C}$), [1391, 1308] ($v_{C-H\ bending}$), [1277, 1237] ($v_{C-O}$), [1166, 1121] ($v_{C-N}$), 1026, 932, 869, 804, [753, 716, 662] ($v_{C=C-H}$); $^1$H NMR (DMSO-D$_6$, 300 MHz): δ 8.52 (t, 1H, J=4.5 Hz, NH), 8.19 (d, 2H, J=7.8 Hz, ArH), 7.87 (d, 2H, J=8.1 Hz, ArH), 7.80-7.72 (m, 5H, ArH), 7.65-7.55 (m, 4H, ArH), 7.45 (t, 2H, J=7.2 Hz, ArH), 7.24 (t, 2H, J=7.2 Hz, ArH), 5.81 (t, 1H, J=6.6 Hz), 3.65 (s, 3H), 3.16 (q, 2H, J=14.4, 5.7 Hz), 2.40 (q, 2H, J=14.4, 6.6 Hz), 1.57-1.27 (m, 3H), 0.95-0.91 (m, 1H); $^{13}$C NMR (DMSO-D$_6$, 75 MHz): δ 196.90, 172.38, 166.82, 141.15, 140.41, 139.48, 138.19, 134.48, 131.15, 130.86, 130.15, 128.71, 127.31, 123.95, 121.78, 120.65, 111.25, 57.34, 53.83, 40.18, 30.24, 29.90, 24.33; MS (DCI+iBu): m/z 519.224 (7.25%, [MH]$^+$), 391.275 (33.37%), 279.147 (51.07%), 167.039 (50.58%, [carbazole]$^+$), 149.033 (100%); High resolution MS (DCI+iBu) m/z calcd for C$_{33}$H$_{31}$N$_2$O$_4$ [MH]$^+$ 519.2284. Found 519.2240, mDa −4.4.

1.4 Synthesis of (S)-6-(4-benzoyl-benzoylamino)-2-carbazol-9-yl-hexanoic acid (7)

Methanolic KOH (0.050 g, 0.88 mmol) was added to a stirred solution of 6-(4-benzoyl-benzoylamino)-2-carbazol-9-yl-hexanoic acid methyl ester 6 (0.230 g, 0.44 mmol) in a mixture (1:2) of toluene (2 mL) and methanol (4 mL). The resulting reaction mixture was refluxed for 3 h. Subsequently, it was neutralized to pH 3-4 with dil. HCl and extracted with EtOAc (20 mL×2). The combined organic extract was washed with water (15 mL×2) and dried over anhydrous Na$_2$SO$_4$. Removal of solvent under reduced pressure provided 6-(4-benzoyl-benzoylamino)-2-carbazol-9-yl-hexanoic acid 7 (0.210 g, 98%) as a white solid.

White solid, mp: 97-98° C., FT-IR (KBr, cm$^{-1}$): 3387 ($v_{N-H}$, $v_{O-H}$), [3056, 2933, 2864] ($v_{C-H\ stretching}$), 1724 ($v_{C=O\ acid}$), 1649 ($v_{C=O\ amide}$), [1544, 1487, 1450] ($v_{C=C}$), 1319 ($v_{C-H\ bending}$), [1278, 1229] ($v_{C-O}$), [1165] ($v_{C-N}$), 1017, 931, [755, 714, 654] ($v_{C=C-H}$); $^1$H NMR (DMSO-D$_6$, 300 MHz): δ 8.53 (t, 1H, NH), 8.19 (d, 2H, J=7.5 Hz, ArH), 7.87 (d, 2H, J=8.4 Hz, ArH), 7.80-7.73 (m, 5H, ArH), 7.61 (q, 4H, J=14.7, 7.8 Hz, ArH), 7.44 (t, 2H, J=7.5 Hz, ArH), 7.23 (t, 2H, J=7.2 Hz, ArH), 5.66 (t, 1H, J=7.2 Hz), 3.16 (m, 2H), 2.37 (m, 2H), 1.36-0.93 (m, 4H); $^{13}$C NMR (DMSO-D$_6$, 75 MHz): δ 196.43, 173.82, 167.48, 140.27, 137.74, 137.29, 133.29, 130.43, 130.34, 128.79, 127.17, 126.24, 123.65, 120.75, 119.94, 109.90, 56.79, 39.79, 29.04, 28.85, 23.49; MS (TOF ES$^-$): m/z 503 (68.01%, [M-H]$^-$), 324 (100%); MS (DCI+CH4): m/z 505.208 (12.90%, [MH]$^+$), 460 (100%, [M-H$_2$CO$_2$]$^+$), 227.068 (93.70%), 209 (40.24%), 180.077 (93.75%), 167 (53.79); HR-MS (DCI+CH4) m/z calcd for C$_{32}$H$_{29}$N$_2$O$_4$ [MH]$^+$505.2127. Found 505.2078, mDa −4.9.

Example 2

Synthesis of (S)-6-(4-azido-benzoylamino)-2-carbazol-9-yl-hexanoic acid (14)

The total multi-step synthesis of photoreactive carbazole (Cbz) based oxidizable monomer (S)-6-(4-azido-benzoylamino)-2-carbazol-9-yl-hexanoic acid 14 is depicted in Scheme 2.

2.1 Synthesis of 4-(benzyloxycarbonylamino)benzoic acid (10)

Aqueous NaOH (2N, 1.93 g, 48.3 mmol) was added to a solution of 4-aminobenzoic acid (3.0 g, 21.90 mmol) in H$_2$O at 0° C. A clear solution appeared within 5 min. Then, benzyl carbonochloridate (4.45 g, 26.28 mmol) was added dropwise to the mixture and it was heated to room temperature and stirred for 2 h. The reaction mixture was diluted with water and separated with ether. The aqueous layer was cooled to 0° C. temperature and acidified with 6M HCl. The solid was collected by filtration, washed with water and dried. The crude solid was recrystallized from ethyl acetate-hexane to furnish 4-(benzyloxycarbonylamino)benzoic acid 10 (5.0 g, 84%) as a white solid.

White solid, mp: >235° C.; $^1$H NMR (DMSO-D6, 300 MHz): δ 12.65 (bs, 1H, COOH), 10.19 (s, 1H, NH), 7.91 (d, 2H, J=8.7 Hz, ArH), 7.62 (d, 2H, J=8.7 Hz, ArH), 7.49-7.33 (m, 5H, ArH), 5.21 (s, 2H); 13C NMR (DMSO-D6, 75 MHz): δ 167.95, 154.17, 144.28, 137.31, 131.45, 129.44, 129.18, 129.11, 125.39, 118.31, 67.03.

2.2 Synthesis of (S)-6-(4-benzyloxycarbonylamino-benzoylamino)-2-carbazol-9-yl-hexanoic acid methyl ester (11)

Oxalyl chloride (1.0 mL) was added to a stirred solution of 4-benzyloxy-carbonylamino-benzoic acid 10 (0.271 g, 1.0 mmol) in dry dichloromethane (5 mL) under nitrogen atmosphere at 0° C. The reaction mixture was stirred for 30 min at 0° C., and then for additional 3 h at room temperature until the formation of a clear solution. The solvent was removed under reduced pressure to leave a white solid (Acid Chloride) which was dissolved in chloroform (5 mL). Then, the acid chloride solution was added drop-wise to a well-stirred solution of amine, (S)-methyl 6-amino-2-carbazol-9-yl-hexanoate 4 (0.310 g, 1.0 mmol) in dry chloroform (10 mL) and dry Et$_3$N (0.6 mL) at 0° C. under nitrogen atmosphere. The reaction mixture was stirred overnight at room temperature, poured into water (20 mL), and extracted with chloroform (30 mL×2). The combined organic extracts were washed with water and brine (10 mL×2) and dried over anhydrous Na$_2$SO$_4$. After removal of solvent, the residue was purified by column chromatography (silica gel 230-400 mesh) using dichloromethane:methanol (98:2) as eluent to afford (S) 6-(4-benzyloxycarbonylamino-benzoylamino)-2-carbazol-9-yl-hexanoic acid methyl ester 11 (0.400 g, 71% two steps) as a white solid.

White solid, mp: 87-88° C., FT-IR (KBr, cm$^{-1}$): 3340 ($v_{n-H}$), [3050, 2944, 2862] ($v_{C-H\ stretching}$), 1735 ($v_{C=O\ ester}$), 1639 ($v_{C=O\ amide}$), [1602, 1527, 1450] ($v_{C=C}$), 1316 ($v_{C-H\ bending}$), 1223 ($v_{C-O}$), 1124 ($v_{C-N}$), 1055, 852, 754 ($v_{C=C-H}$); $^1$H NMR (DMSO-D$_6$, 300 MHz): δ 10.64 (s, 1H, —NHCOOCH$_2$Ph), 8.20 (d, 2H, J=7.8 Hz, ArH), 8.19 (bs, 1H, NH), 7.69 (d, 2H, J=8.7 Hz, ArH), 7.55 (d, 2H, J=8.7 Hz, ArH), 7.58-7.36 (m, 9H, ArH), 7.25 (t, 2H, J=7.2 Hz, ArH), 5.79 (t, 1H, J=6.9 Hz), 5.21 (s, 2H), 3.65 (s, 3H), 3.09 (q, 2H, J=12.6, 6.6 Hz), 2.39 (q, 2H, J=15.3, 6.3 Hz), 1.55-0.85 (m, 4H); $^{13}$C NMR (DMSO-D$_6$, 75 MHz): δ 172.38, 167.04, 154.73, 143.01, 141.18, 137.92, 129.95, 129.64, 129.45, 127.31, 123.94, 121.79, 120.65, 118.64, 111.25, 67.43, 57.34, 53.82, 40.16, 30.24, 30.07, 24.35; MS (TOF ES+): m/z 564 (78.38%, [MH]$^+$).

2.3 Synthesis of (S)-6-(4-amino-benzoylamino)-2-carbazol-9-yl-hexanoic acid methyl ester (12)

10% Pd/C (0.035 g) was added in one portion to a stirred solution of (S)-6-(4-benzyloxycarbonylamino-benzoylamino)-2-carbazol-9-yl-hexanoic acid methyl ester 11 (0.350 g, 0.62 mmol) in a 1:1 mixture of THF (5 mL) and isopropanol (5 mL) and nitrogen atmosphere. The reaction mixture was subsequently stirred under hydrogen atmosphere for 4 h at room temperature. The reaction mixture was passed through a celite pad, and the filtrate was concentrated in under reduced pressure to give (S) 6-(4-amino-benzoylamino)-2-carbazol-9-yl-hexanoic acid methyl ester (12) (0.260 g, 98%) as a white solid.

White solid, mp: 90-91° C., FT-IR (KBr, cm$^{-1}$): 3348 ($\nu_{O-H}$), 3227 ($\nu_{N-H}$), [3052, 2940, 2862] ($\nu_{C-H\ stretching}$), 1737 ($\nu_{C=O\ ester}$) 1613 ($\nu_{C=O\ amide}$), [1545, 1500, 1449] ($\nu_{C=C}$), 1288 ($\nu_{C-O}$), 1126 ($\nu_{C-N}$), 1019, 845, [756, 663, 608] ($\nu_{C=C-H}$); $^1$H NMR (DMSO-D$_6$, 300 MHz): δ 8.21 (d, 2H, J=7.5 Hz, ArH), 7.87 (t, 1H, J=5.1 Hz, NH), 7.59-7.44 (m, 6H, ArH), 7.26 (t, 2H, J=7.8 Hz, ArH), 6.55 (d, 2H, J=8.4 Hz, ArH), 5.8 (t, 1H, J=7.8 Hz), 5.63 (bs, 2H, NH$_2$), 3.66 (s, 3H), 3.08-2.99 (m, 2H), 2.41-2.36 (m, 2H), 1.50-1.41 (m, 2H), 1.32-1.21 (m, 1H), 0.91-0.87 (m, 1H); $^{13}$C NMR (DMSO-D$_6$, 75 MHz): δ 172.12, 167.31, 152.53, 140.91, 129.76, 127.05, 123.67, 122.68, 121.53, 120.39, 113.72, 109.90, 57.09, 53.56, 39.76, 29.99 (2C), 24.10; MS (TOF ES+): m/z 430 (100%, [MH]$^+$).

2.4 Synthesis of (S)-6-(4-azido-benzoylamino)-2-carbazol-9-yl-hexanoic acid methyl ester (13)

(S)-6-(4-Amino-benzoylamino)-2-carbazol-9-yl-hexanoic acid methyl ester 12 (0.220 g, 0.513 mmol) was dissolved in 5% HCl (9.0 mL) and acetone (9.0 mL) at 0° C. in the dark. NaNO$_2$ (0.039 g, 0.564 mmol) in 2.0 mL H$_2$O was added to the reaction mixture, causing a color change to pale yellow. After 30 min of stirring, NaN$_3$ (0.333 g, 5.13 mmol) in 5.0 mL H$_2$O was added to the reaction mixture at 0° C. causing an immediate color change from yellow to colorless. The reaction mixture was further stirred for additional 15 min, poured into water (10 mL), and extracted with ethyl acetate (30 mL×2). The combined organic extract was washed with water (10 mL×2) and brine (10 mL×2), dried over anhydrous Na$_2$SO$_4$ and evaporated under reduced pressure. The crude residue was purified by flash column chromatography on silica gel (230-400 mesh), eluting with hexane:acetone (90:10 to 80:20) to furnish a yellow solid (S) 6-(4-azido-benzoylamino)-2-carbazol-9-yl-hexanoic acid methyl ester 13 (0.200 g, 86%).

Light yellow solid, mp: 65-67° C., FT-IR (KBr, cm$^{-1}$): 3333 ($\nu_{N-H}$), [3057, 2950, 2863] (($\nu_{C-H\ stretching}$), 2123 ((N$_3$), 1740 ($\nu_{C=O\ ester}$), 1641 ($\nu_{C=O\ amide}$), [1602, 1543, 1499, 1454] (($\nu_{C=C}$), 1284 ($\nu_{C-O}$), 1123 ($\nu_{C-N}$), 1024, 849, [752, 725] ($\nu_{C=C-H}$); $^1$H NMR (CDCl$_3$, 300 MHz): δ 8.04 (d, 2H, J=7.5 Hz, ArH), 7.48 (d, 2H, J=8.7 Hz, ArH), 7.41-7.32 (m, 4H, ArH), 7.22-7.17 (m, 2H, ArH), 6.95 (d, 2H, J=8.7 Hz, ArH), 5.74 (bs, 1H, NH), 5.21 (q, 1H, J=12.0, 6.3, Hz), 3.61 (s, 3H), 3.26-3.19 (m, 2H), 2.46-2.34 (m, 2H), 1.55-0.95 (m, 4H); $^{13}$C NMR (CDCl$_3$, 75 MHz): δ 171.70, 167.22, 143.78, 140.57, 131.62, 129.29, 126.60, 123.97, 121.11, 120.26, 119.52, 110.06, 57.31, 53.28, 40.02, 29.68, 29.48, 23.94; MS (TOF ES+): m/z 456 (100%, MH$^+$).

2.5 Synthesis of (S)-6-(4-azido-benzoylamino)-2-carbazol-9-yl-hexanoic acid (14)

Methanolic KOH (0.075 g, 1.32 mmol) was added to a stirred solution of (S)-6-(4-azido-benzoylamino)-2-carbazol-9-yl-hexanoic acid methyl ester 13 (0.200 g, 0.44 mmol) in a mixture (2:1) of methanol (6 mL) and toluene (3 mL) at room temperature. The reaction mixture was refluxed at 60° C. for 3.5 h. After cooling to 0° C., 1M HCl solution was added drop-wise for the acidification up to pH=3-4 and extracted with EtOAc (30 mL×2). The combined organic extract was washed with water (20 mL×2) and dried over anhydrous Na$_2$SO$_4$. Removal of solvent under reduced pressure provided (S)-6-(4-azido-benzoylamino)-2-carbazol-9-yl-hexanoic acid 14 (0.170 g, 88%) as a yellow solid.

Yellow solid, mp: 98-100° C., FT-IR (KBr, cm$^{-1}$): 3384 ($\nu_{O-H}$, $\nu_{N-H}$), [3058, 2936, 2864] ($\nu_{C-H\ stretching}$), 2123 (N$_3$), 1722 ($\nu_{C=O\ acid}$), 1640 ($\nu_{C=O\ amide}$), [1603, 1546, 1500, 1453] ($\nu_{C-C}$), 1382 ($\nu_{C-H\ bending}$), 1284 ($\nu_{C-O}$), [1158, 1125] ($\nu_{C-N}$), 1027, 847, [752, 724] ($\nu_{C=C-H}$); $^1$H NMR (CDCl$_3$, 300 MHz): δ 8.04 (d, 2H, J=7.5 Hz, ArH), 7.39-7.17 (m, 8H, ArH), 6.86 (d, 2H, J=7.2 Hz, ArH), 5.98 (bs, 1H, NH), 5.23 (t, 1H, J=7.5 Hz), 3.21-3.08 (m, 2H), 2.40-2.31 (m, 2H), 1.43-0.96 (m, 4H); $^{13}$C NMR (CDCl$_3$, 75 MHz): δ 173.77, 167.62, 143.74, 140.34, 130.70, 129.04, 126.29, 123.70, 120.80, 119.97, 119.27, 110.03, 56.92, 39.82, 29.13, 28.94, 23.56; MS (TOF ES+): m/z 464 (44.31%, [M+Na]$^+$), 442 (100%, [MH]$^+$), 414 (59.17%, [M-N$_2$]$^+$); HR-MS (DCl+CH4) m/z calcd for C$_{25}$H$_{24}$N$_5$O$_3$ [MH]$^+$ 442.1879. Found 442.1891, mDa 1.2.

Example 3

Synthesis of (S)-4-(2-(4-azidobenzoyloxy)ethoxy)-2-(9H-carbazol-9-yl)-4-oxobutanoic acid (20)

The total multi-step synthesis of photoreactive carbazole (Cbz) based oxidizable monomer (S)-4-(2-(4-azidobenzoyloxy)ethoxy)-2-(9H-carbazol-9-yl)-4-oxobutanoic acid 20 is depicted in Scheme 3.

3.1 Synthesis of (S)-2-carbazoyl-9-yl-succinic acid 1-benzyl ester (16)

To a vigorously stirred solution of H-Asp-OBzl 15 (5.0 g, 22.40 mmol) in glacial acetic acid (80 mL) and 1,4-dioxane (45 ml) was added concentrated HCl (2.5 mL, 12N) and the resulting mixture was heated to ~75° C. At this temperature, DMTHF (8.90 g, 8.70 mL, 67.2 mmol) was added dropwise to the reaction mixture. After complete addition of DMTHF, the reaction mixture was refluxed at 110° C. for 2 h followed by 4-5 h of stirring at room temperature. The volatiles were removed under reduced pressure to furnish a dark brawn oily residue which was dissolved in CH$_2$Cl$_2$ (100 mL) and washed with brine (50 mL×2) and water (50 mL×2). The organic layers were dried over anhydrous Na$_2$SO$_4$, filtrated and concentrated under reduced pressure to afford crude dark residue which was purified by flash chromatography on a silica gel column using hexane:ethyl acetate (7:3) as eluent to furnish (S)-2-carbazoyl-9-yl-succinic acid 1-benzyl ester 16 (2.50 g, 30%) as pale yellow solid.

Pale yellow solid, mp: 105° C., FT-IR (KBr, cm$^{-1}$): 3316 ($\nu_{O-H}$), [3038, 2933] ($\nu_{C-H\ stretching}$), 1727 ($\nu_{C=O\ ester}$), 1714 ($\nu_{C=O\ acid}$), [1598, 1485, 1454] ($\nu_{C=C}$), [1290, 1218 ($\nu_{C-H\ bending}$), [1176, 1159] ($\nu_{C-O}$), [750, 723] ($\nu_{C=C-H}$); $^1$H NMR (CDCl$_3$, 300 MHz): δ 10.07 (bs, 1H, —COOH), 8.05 (d, 2H, J=7.8 Hz, ArH), 7.36-7.30 (m, 4H ArH), 7.22-7.11 (m, 5H, ArH), 7.23 (d, 2H, J=8.1 Hz, ArH), 5.85 (t, 1H, J=6.6 Hz), 5.08 (s, 2H), 3.70 (q, 1H, J=17.1, 7.5 Hz), 2.97 (q, 1H, J=17.4, 6.3 Hz); $^{13}$C NMR (CDCl$_3$, 75 MHz): δ 176.60, 169.86, 139.90, 135.05, 128.69, 128.57, 128.29, 126.36, 123.89, 120.76, 120.22, 109.49, 68.05, 53.34, 34.98; MS (DCI+i-Bu): m/z 373 (18.5%, [M]$^+$), 280 (26.1%, [M-PhCH$_2$H]$^+$), 238 (33.5%, [M-PhCH$_2$OCO]$^+$), 167.064 (100%, [carbazol]$^+$); HR-MS (DCI+i-Bu) m/z calcd for C$_{23}$H$_{19}$NO$_4$ [MH]$^+$ 373.1314. Found 373.1285.

3.2 Synthesis of (S)-1-benzyl 4-(2-hydroxyethyl) 2-(9H-carbazol-9-yl)succinate (17)

To a solution of 16 (0.373 g, 1.0 mmol) in $CH_2Cl_2$ (10 mL) were added N,N'-dicyclohexylcarbodiimide (DCC) (0.227 g, 1.10 mmol) and catalytic amount of 4-dimethylaminopyridine (DMAP) (0.018 g, 0.15 mmol) under nitrogen atmosphere. The reaction mixture was cooled to 0° C. and ethylene glycol (0.250 g, 4.0 mmol) in $CH_2Cl_2$ (2 mL) was added dropwise. The new reaction mixture was allowed to warm up to room temperature and stirred for 30 min. DCU was removed from the reaction mixture by filtration, and the filtrate was washed with water (20 mL×2), brine (20 mL×2), dried over anhydrous $Na_2SO_4$, filtrated and concentrated under reduced pressure to afford crude dark residue which was purified by flash chromatography on a silica gel column using EtOAc:hexane (1:4 to 2:3) as eluent to afford (S)-1-benzyl 4-(2-hydroxyethyl) 2-(9H-carbazol-9-yl)succinate 17 (0.250 g, 60%) as a yellow gummy liquid.

Yellow gummy liquid, FT-IR (Neat, $cm^{-1}$): 3413 ($v_{O-H,\ alcohol}$), [3058, 2939] ($v_{C-H\ stretching}$), 1735 ($v_{C=O\ ester}$), [1596, 1486, 1451, 1386] ($v_{C=C}$), 1336 ($v_{C-H\ bending}$), 1276, 1223 ($v_{C-O}$), 1166, 1074, 1021, 752 ($v_{C=C-H}$); $^1H$ NMR ($CDCl_3$, 300 MHz): δ 8.08 (d, 2H, J=7.8 Hz, ArH), 7.39-7.34 (m, 4H, ArH), 7.27-7.13 (m, 5H, ArH), 6.97 (m, 2H, J=8.1 Hz, ArH), 5.93 (t, 1H, J=7.2 Hz), 5.10 (s, 2H), 4.19-4.03 (m, 2H), 3.69-3.63 (m, 3H), 3.09 (q, 1H, J=16.5, 7.2 Hz); $^{13}C$ NMR ($CDCl_3$, 75 MHz): δ 170.94, 170.07, 139.90, 135.07, 128.73, 128.63, 128.37, 126.38, 120.79, 120.25, 109.57, 68.09, 67.02, 61.16, 53.76, 35.21; MS (TOF ES+): m/z 418 (100%, [MH]$^+$), 400 (35.79%, [MH-$H_2O$]$^+$), 356 (37.18%, [MH-HOCH$_2$CH$_2$OH]$^+$).

3.3 Synthesis of (S)-1-benzyl 4-(2-(4-(benzyloxycarbonylamino)benzoyloxy)ethyl) 2-(9H-carbazol-9-yl)succinate (18)

(S)-1-benzyl 4-(2-hydroxyethyl) 2-(9H-carbazol-9-yl)succinate 17 (0.500 g, 1.20 mmol) was added to a solution of 4-(benzyloxycarbonylamino)benzoic acid 10 (0.389 g, 1.44 mmol), EDCHCl (0.304 g, 1.58 mmol) and DMAP (0.043 g, 0.35 mmol) in $CH_2Cl_2$ (10 mL). After the reaction mixture was refluxed for 24 h, the solution was extracted with $CH_2Cl_2$ (100 mL) and water (100 mL). The organic layer was washed with brine (100 mL), dried over anhydrous $Na_2SO_4$ and concentrated under reduced pressure. The residue was purified by flash chromatography on a silica gel column using $CH_3OH$:$CH_2Cl_2$ (1:99) to afford (S)-1-benzyl 4-(2-(4-(benzyloxycarbonylamino)benzoyloxy)ethyl) 2-(9H-carbazol-9-yl)succinate 18 (0.480 g, 60%) as a white solid.

White solid, mp: 58° C., FT-IR (Neat, $cm^{-1}$): 3346 ($v_{N-H}$), 2927 ($v_{C-H\ stretching}$), 1732 ($v_{C=O\ ester}$), [1600, 1532, 1450, 1413] ($v_{C=C}$), 1321 ($v_{C-H\ bending}$), 1274, 1216 ($v_{C-O}$), 1168, 1109, 1050, 759 ($v_{C=C-H}$); $^1H$ NMR ($CDCl_3$, 300 MHz): δ 8.04 (d, 2H, J=7.5 Hz, ArH), 7.89 (d, 2H, J=8.7 Hz, ArH), 7.42-7.35 (m, 11H, ArH), 7.22-7.11 (m, 5H, ArH), 6.94 (d, 3H, J=8.1 Hz, ArH & NH), 5.93 (t, 1H, J=6.9 Hz), 5.20 (bs, 2H, —CH$_2$Ph), 5.06 (q, 2H, J=17.4, 12.6 Hz, —CH$_2$Ph), 4.35-4.25 (m, 4H, —OCH$_2$CH$_2$O—), 3.68 (q, 1H, J=16.8, 7.2 Hz), 3.07 (q, 1H, J=16.8, 7.2 Hz); $^{13}C$ NMR ($CDCl_3$, 75 MHz): δ 170.62, 169.89, 166.06, 153.13, 142.63, 139.95, 136.01, 135.12, 131.41, 129.02, 128.88, 128.74, 128.69, 128.56, 128.29, 126.33, 124.66, 123.85, 120.74, 120.17, 117.88, 109.57, 67.97, 67.70, 63.24, 62.56, 53.59, 35.19; MS (TOF ES+): m/z 671 [MH]$^+$.

3.4 Synthesis of (S)-4-(2-(4-aminobenzoyloxy)ethoxy)-2-(9H-carbazol-9-yl)-4-oxobutanoic acid (19)

10% Palladium on charcoal (0.040 g) was added in one portion to a stirred solution of 18 (0.360 g, 0.57 mmol) in a 1:1 mixture of isopropanol (4 mL) and THF (4 mL) under nitrogen atmosphere. The suspension was then stirred under hydrogen atmosphere for 6 h. The solution was filtered through celite and concentrated under reduced pressure. The residue was purified by flash silica gel column chromatography $CH_3OH$:$CH_2Cl_2$ (5:95) to afford to obtain (S)-4-(2-(4-aminobenzoyloxy)ethoxy)-2-(9H-carbazol-9-yl)-4-oxobutanoic acid 19 (0.230 g, 96%) as a white solid.

White solid, mp: 100° C., FT-IR (KBr, $cm^{-1}$): 3469 ($v_{O-H,\ acid}$), 3380 ($v_{N-H,\ amine}$), [3056, 2953, 2929 2857] ($v_{C-H\ stretching}$), 1726 ($v_{C=O\ ester}$), 1701 ($v_{C=O\ acid}$), [1607, 1519, 1488, 1450] ($v_{C=C}$), 1380 ($v_{C-H\ bending}$), 1277 ($v_{C-O}$), 1169 ($v_{C-N}$), 1117, 1056, 756 ($v_{C=C-H}$); $^1H$ NMR ($CDCl_3$, 300 MHz): δ 8.06 (d, 2H, J=7.5 Hz, ArH), 7.78 (d, 2H, J=8.4 Hz, ArH), 7.40 (m, 4H, ArH), 7.26 (m, 4H, ArH), 6.56 (d, 1H, J=8.7 Hz), 6.48 (d, 1H, J=8.1 Hz), 5.97-5.91 (m, 1H), 4.41-4.37 (m, 4H, —OCH$_2$CH$_2$—), 3.70-3.62 (m, 1H), 3.04-2.98 (m, 1H)); $^{13}C$ NMR ($CDCl_3$, 75 MHz): δ 170.98, 166.87, 151.32, 143.52, 139.95, 128.76, 126.22, 123.69, 120.63, 119.97, 114.18, 109.71, 63.34, 62.37, 53.57, 35.13; MS (TOF ES+): m/z 485 (2.02%, [M+K]$^+$), 469 (6.11%, [M+Na]$^+$), 447 (95.10%, [MH]$^+$), 120 (100%, [$H_2C_6H_4CO$]$^+$).

3.5 Synthesis of (S)-4-(2-(4-azidobenzoyloxy)ethoxy)-2-(9H-carbazol-9-yl)-4-oxobutanoic acid (20)

To a stiffed solution of 19 (0.115 g, 0.260 mmol) in acetone (6 mL) was added 5% HCl (6 mL) at 0° C. and the solution was stiffing for 5 min NaNO$_2$ (0.020 g, 0.28 mmol) in 1 mL water was added dropwise to the above solution causing an immediate color change from colorless to orange. After 20 min of stirring at 0° C., NaN$_3$ (0.034 g, 0.52 mmol) in 1 mL water was added dropwise to the reaction mixture causing an immediate color changed from orange to colorless to pale yellow. The reaction mixture was stiffed for additional 20 min and extracted with ethyl acetate (50 mL), washed with water (20 mL) and brine (20 mL). The final organic layer was dried over anhydrous $Na_2SO_4$, filtrated and concentrated under reduced pressure to obtain (S)-4-(2-(4-azidobenzoyloxy)ethoxy)-2-(9H-carbazol-9-yl)-4-oxobutanoic acid 20 (0.117 g, 96%) as an off white solid.

Off white solid, mp: 55° C., FT-IR (KBr, $cm^{-1}$): 3450 ($v_{O-H,\ acid}$), [3057, 2929, 2860] ($v_{C-H\ stretching}$), 2122 (—N$_3$), 1724 (br, $v_{C=O\ ester,\ acid}$), [1600, 1493, 1452, 1382] ($v_{C=C}$), 1277 ($v_{C-O}$), 1169 ($v_{C-N}$), 1122, 754 ($v_{C=C-H}$); $^1H$ NMR ($CDCl_3$, 300 MHz): δ 8.03 (d, 2H, J=7.8 Hz, ArH), 7.86 (d, 2H, J=8.7 Hz, ArH), 7.43-7.38 (m, 4H, ArH), 7.26-7.21 (m, 2H, ArH), 6.96 (d, 2H, J=8.7 Hz, ArH), 5.94 (t, 1H, J=6.9 Hz), 4.39-4.24 (m, 4H, —OCH$_2$CH$_2$—), 3.62 (q, 1H, J=17.1, 7.2 Hz), 3.07 (q, 1H, J=16.8, 6.9 Hz); $^{13}C$ NMR ($CDCl_3$, 75 MHz): δ 173.96, 170.51, 165.84, 145.32, 139.80, 131.81, 126.43, 126.30, 123.88, 120.87, 120.37, 119.16, 109.47, 63.21, 62.79, 53.08, 34.90; MS (DCI+CH4): m/z 472.134 (24.13%, [M]$^+$), 428.138 (29.52%, [M-CO$_2$]$^+$), 402 (20.35%), 220.074 (38.14%), 193.092 (59.98%), 169.087 (81.16%), 139.040 (100%), 120.011 (97.73%); High resolution MS (DCI+CH4) m/z calcd for $C_{25}H_{20}N_4O_6$ [M]$^+$ 472.1383. Found 472.1345, mDa −3.8.

Example 4

Synthesis of (S)-5-(2-(4-azidobenzoyloxy)ethoxy)-2-(9H-carbazol-9-yl)-5-oxopentanoic acid (26)

The total multi-step synthesis of photoreactive carbazole (Cbz) based oxidizable monomer (S)-5-(2-(4-azidobenzoyloxy)ethoxy)-2-(9H-carbazol-9-yl)-5-oxopentanoic acid 26 is depicted in Scheme 4.

4.1 Synthesis of (S)-5-(benzyloxy)-4-(9H-carbazol-9-yl)-5-oxopentanoic acid (22)

To a vigorously stirred solution of H-Glu-OBzl (21) (2.5 g, 10.50 mmol) in glacial acetic acid (40 mL) and 1,4-dioxane (25 ml) was added conc. HCl (1.5 mL, 12N) and the resultant mixture was heated to ~75° C. At this temperature, DMTHF (5.00 g, 5.00 mL, 38.60 mmol) was added dropwise to the reaction mixture. After complete addition of DMTHF, the reaction mixture was refluxed at 110° C. for 2 h followed by 4-5 h of stirring at room temperature. The volatiles were removed under reduced pressure to furnish a dark brown oily residue, which was dissolved in $CH_2Cl_2$ (100 mL) and washed with brine (50 mL×2) and water (50 mL×2). The organic layers were dried over anhydrous $Na_2SO_4$, filtered and concentrated under reduced pressure to afford crude dark residue which was purified by flash chromatography on a silica gel column using hexane/ethyl acetate (20-40:80-60) as eluent to furnish (S)-5-(benzyloxy)-4-(9H-carbazol-9-yl)-5-oxopentanoic acid 22 (1.50 g, 38%) as a pale yellow solid.

Pale yellow solid, mp: 100° C.; FT-IR (KBr, cm$^{-1}$): 3319 ($v_{O-H}$), [3061, 2931] ($v_{C-H\ stretching}$), 1734 ($v_{C=O\ ester}$), 1647 ($v_{C=O\ acid}$), [1597, 1535, 1483, 1453] ($v_{C=C}$), 1329 ($v_{C-H\ bending}$), 1237 ($v_{C-O}$), 1159 ($v_{C-N}$), [7501, 724] ($v_{C=C-H}$); $^1$H NMR (CDCl$_3$, 300 MHz): δ 10.89 (bs, 1H, —COOH), 8.28 (d, 2H, J=7.8 Hz, ArH), 7.62-7.31 (m, 9H ArH), 7.24-7.16 (m, 2H, ArH), 5.67 (dd, 1H, J=9.6, 6.0 Hz), 5.27 (s, 2H), 3.02-2.79 (m, 2H), 2.42-2.24 (m, 2H); $^{13}$C NMR (CDCl$_3$, 75 MHz): δ 178.8, 170.1, 139.9, 135.0, 128.4, 128.2, 128.1, 126.0, 123.5, 120.5, 119.8, 109.4, 67.3, 55.6, 29.7, 24.5; MS (DCI+CH4): m/z 387 (58.3%, [M]$^+$), 252 (100%, [M-PhCH$_2$OCO]$^+$), 206 (36.0%), 91 (26.7%, [PhCH$_2$]$^+$), 85 (6.2%, [M-carbazol]$^+$); HR-MS (DCI+CH4): m/z calcd for C$_{24}$H$_{21}$Na$_4$ [M]$^+$387.1471. Found 387.1440.

4.2 Synthesis of (S)-1-benzyl 5-(2-hydroxyethyl) 2-(9H-carbazol-9-yl)pentanedioate (23)

To a solution of 22 (1.2 g, 3.10 mmol) in $CH_2Cl_2$ (20 mL) were added DCC (0.703 g, 3.40 mmol) and catalytic amount of DMAP (0.057 g, 0.46 mmol) under nitrogen atmosphere. The reaction mixture was cooled to 0° C. and ethylene glycol (0.770 g, 0.680 mL, 12.4 mmol) in $CH_2Cl_2$ (5 mL) was added dropwise. The reaction mixture was allowed to warm up to room temperature and stirred for 12 h. The solid DCU was removed by filtration and the filtrate was evaporated under reduced pressure. The crude residue obtained was dissolved in $CH_2Cl_2$ (100 mL), washed with water (40 mL×2), brine (40 mL×2), dried over $Na_2SO_4$, filtrated and then concentrated to get a yellow residue. A flash chromatography using CH$_3$OH:CH$_2$Cl$_2$ (1:99) as eluent afforded (S)-1-benzyl 5-(2-hydroxyethyl) 2-(9H-carbazol-9-yl)pentanedioate 23 (0.950 g, 71%) as a yellow gummy liquid.

Yellow gummy liquid, FT-IR (Neat, cm$^{-1}$): 3408, 3331 ($v_{O-H,\ alcohol}$), [3056, 2935, 2859]($v_{C-H\ stretching}$), 1734 ($v_{C-O\ ester}$), [1599, 1488, 1451, 1385] ($v_{C=C}$), 1335 ($v_{C-H\ bending}$), 1200 ($v_{C-O}$), 1166, 1078, 1029, 750 ($v_{C=C-H}$); $^1$H NMR (CDCl$_3$, 300 MHz): δ 8.07 (d, 2H, J=7.8 Hz, ArH), 7.39-7.15 (m, 9H, ArH), 7.01 (d, 2H, J=7.5 Hz, ArH), 5.52 (q, 1H, J=10.2, 6.0 Hz), 5.10 (s, 2H, —OCH$_2$Ph), 3.99 (t, 2H, J=4.5 Hz, OCH$_2$CH$_2$O—), 3.57 (t, 2H, J=4.5 Hz, OCH$_2$CH$_2$O—), 2.75-2.65 (m, 2H, —OCOCH$_2$—), 2.23-2.13 (m, 1H, —CNCHH—), 2.08-1.96 (m, 1H, —CNCHH—); $^{13}$C NMR (CDCl$_3$, 75 MHz): δ 173.12, 170.40, 140.17, 135.32, 128.69, 128.53, 128.36, 126.21, 123.69, 120.72, 119.99, 109.70, 67.59, 66.40, 61.06, 55.74, 29.91, 24.82; MS (TOF ES+): m/z 454 (1.66%, [M+Na]$^+$), 432 (48.15%, [MH]$^+$), 414 (12.56%, [M-OH]$^+$), 370 (26.35%, [M-OCH$_2$CH$_2$OH]$^+$), 225 (100%).

4.3 Synthesis of (S)-1-benzyl 5-(2-(4-(benzyloxycarbonylamino)benzoyloxy)ethyl) 2-(9H-carbazol-9-yl)pentanedioate (24)

To a solution of 4-(benzoyloxycarbonylamino)benzoic acid 10 (0.650 g, 2.40 mmol), EDC HCl (0.510 g, 2.65 mmol) and DMAP (0.044 g, 0.36 mmol) in CH$_2$Cl$_2$ (20 mL) was added (S)-1-benzyl 5-(2-hydroxyethyl) 2-(9H-carbazol-9-yl)pentanedioate 23 (0.800 g, 1.85 mmol). After the reaction mixture was refluxed for 6 h, the solution was extracted with CH$_2$Cl$_2$ (100 mL) and water (100 mL). The organic layer was washed with brine (100 mL), dried over anhydrous Na$_2$SO$_4$ and concentrated under reduced pressure. The residue was purified by flash silica gel column chromatography using CH$_3$OH:CH$_2$Cl$_2$ (1:99) as eluent to afford (S)-1-benzyl 5-(2-(4-(benzyloxycarbonylamino)benzoyloxy)-ethyl) 2-(9H-carbazol-9-yl)pentanedioate 24 (0.80 g, 63%) as a white solid.

White solid, mp: 45° C., FT-IR (Neat, cm$^{-1}$): 3332 ($v_{N-H}$), 3054, 2953 ($v_{C-H\ stretching}$), 1733 ($v_{C=O\ ester}$), [1601, 1531, 1452, 1410] ($v_{C=C}$), 1378, 1321 ($v_{C-H\ bending}$), 1275, 1214 ($v_{C-O}$), 1171, 1109, 1050, 851, 751 ($v_{C=C-H}$), 693; $^1$H NMR (CDCl$_3$, 300 MHz): δ 8.07 (d, 2H, J=7.8 Hz, ArH), 7.89 (d, 2H, J=8.7 Hz, ArH), 7.41-7.17 (m, 16H), 7.01 (dd, 3H, J=7.5, 1.5 Hz, ArH), 6.94 (bs, 1H, NH), 5.54 (q, 1H, J=10.2, 6.0 Hz), 5.20 (s, 2H, —NHCOOCH$_2$Ph), 5.10 (s, 2H, —COOCH$_2$Ph), 4.36-4.30 (m, 2H, OCH$_2$CH$_2$O—), 4.26-4.22 (m, 2H, OCH$_2$CH$_2$O—), 2.75-2.66 (m, 2H, OCOCH$_2$—), 2.28-2.19 (m, 1H, —CCHH—), 2.14-2.05 (m, 1H, —CCHH—); $^{13}$C NMR (CDCl$_3$, 75 MHz): δ 172.79, 170.41, 166.09, 153.13, 142.64, 140.22, 136.01, 135.39, 131.37, 129.01, 128.87, 128.73, 128.53, 128.36, 126.23, 124.66, 123.75, 120.73, 119.99, 117.87, 109.70, 67.68, 67.60, 62.72, 62.67, 55.80, 29.98, 24.93; MS (TOF ES+): m/z 685 (68.1%, [MH]$^+$), 219 (100%).

4.4 Synthesis of (S)-5-(2-(4-aminobenzoyloxy)ethoxy)-2-(9H-carbazol-9-yl)-5-oxopentanoic acid (25)

10% Palladium on charcoal (0.140 g) was added in one portion to a stirred solution of 24 (0.70 g, 1.02 mmol) in 1:1 mixture of isopropanol (10 mL) and THF (10 mL) under nitrogen atmosphere. The suspension was then stirred under hydrogen atmosphere at room temperature for 4 h. The solution was filtered through celite and concentrated under reduced pressure to obtain (S)-5-(2-(4-aminobenzoyloxy)ethoxy)-2-(9H-carbazol-9-yl)-5-oxopentanoic acid 25 (0.45 g, 96%) as a white solid.

White solid, mp: 65° C., FT-IR (KBr, cm$^{-1}$): 3471 ($v_{O-H,\ acid}$) 3377 ($v_{N-H}$), 3224, [3054, 2950] ($v_{C-H\ stretching}$), 1727 (bs, $v_{C=O\ ester,\ acid}$), [1607, 1450] ($v_{C=C}$), 1378 ($v_{C-H\ bending}$), 1277 ($v_{C-O}$), 1167, 1117, 846, 755 ($v_{C=C-H}$); $^1$H NMR (CDCl$_3$, 300 MHz): δ 8.03 (d, 2H, J=7.5 Hz, ArH), 7.73 (d, 2H, J=8.4 Hz, ArH), 7.35-7.17 (m, 6H, ArH), 6.53 (d, 2H, J=8.4 Hz, ArH), 5.43 (bs, 3H, $NH_2$ & CH), 4.32-4.16 (m, 4H, —$OCH_2CH_2$—), 2.69-2.59 (m, 2H), 2.16-2.02 (m, 2H); $^{13}C$ NMR ($CDCl_3$, 75 MHz): δ 174.04, 172.85, 166.74, 150.70, 140.06, 132.00, 126.27, 123.67, 120.75, 120.04, 114.57, 109.69, 62.85, 62.29, 55.43, 30.09, 24.77; MS (TOF ES+): m/z 461 (100%, $[MH]^+$), 324 (54.05%, $[M-O_2CC_6H_4NH_2]^+$).

4.5 Synthesis of (S)-5-(2-(4-azidobenzoyloxy)ethoxy)-2-(9H-carbazol-9-yl)-5-oxopentanoic acid (26)

To a stirred solution of 25 (0.38 g, 0.83 mmol) in acetone (8 mL) was added 5% HCl (8 mL) at 0° C. and the solution was stiffed for 5 min $NaNO_2$ (0.70 g, 1.0 mmol) in 1 mL water was added dropwise to the above solution causing an immediate color change from colorless to orange. After 20 min of stiffing at 0° C., $NaN_3$ (0.107 g, 1.65 mmol) in 1 mL water was added dropwise to the reaction mixture causing an immediate color changed from orange to colorless to pale yellow. The reaction mixture was stiffed for additional 30 min and extracted with ethyl acetate (100 mL), washed with water (30 mL) and brine (30 mL). The final organic layer was dried over anhydrous $Na_2SO_4$, filtrated and concentrated under reduced pressure to obtain (S)-5-(2-(4-azidobenzoyloxy)ethoxy)-2-(9H-carbazol-9-yl)-5-oxopentanoic acid 26 (0.34 g, 85%) as an off white gummy solid.

Off white solid, mp: 70° C., FT-IR (Neat, $cm^{-1}$): 3415 ($v_{O-H, acid}$), [3057, 2953 ($v_{C-H\ stretching}$), 2123 (—$N_3$), 1723 ($v_{C=O\ ester,\ acid}$), [1602, 1493, 1452, 1412, 1380] ($v_{C=C}$), 1278 ($v_{C-O}$), 1170, 1105, 851, 756 ($v_{C=C-H}$); $^1H$ NMR ($CDCl_3$, 300 MHz): δ 8.01 (d, 2H, J=7.2 Hz, ArH), 7.89 (d, 2H, J=8.4 Hz, ArH), 7.27-7.25 (m, 2H, ArH), 7.16 (t, 4H, J=7.2 Hz, ArH), 6.97 (d, 2H, J=8.4 Hz, ArH), 5.23-5.21 (m, 1H), 4.27-4.15 (m, 4H, —$OCH_2CH_2$—), 2.47-2.44 (m, 2H), 2.01-1.88 (m, 2H); $^{13}C$ NMR ($CDCl_3$, 75 MHz): δ 175.13, 172.88, 165.83, 145.30, 140.02, 131.81, 126.38, 126.13, 123.58, 120.67, 119.91, 119.15, 109.75, 62.85, 62.60, 55.77, 30.09, 24.71; HR-MS (DCl+CH4): m/z 486.158 $[M]^+$ calcd for $C_{26}H_{22}N_4O_6$ 486.1539. found 486.1584, mDa 4.5.

Example 5

Figure 1B:
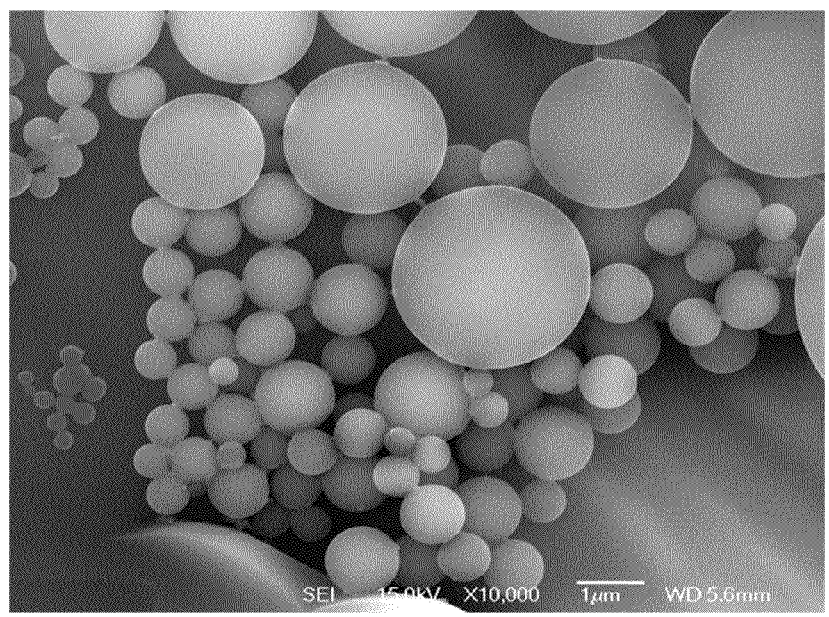
Figure 1C:
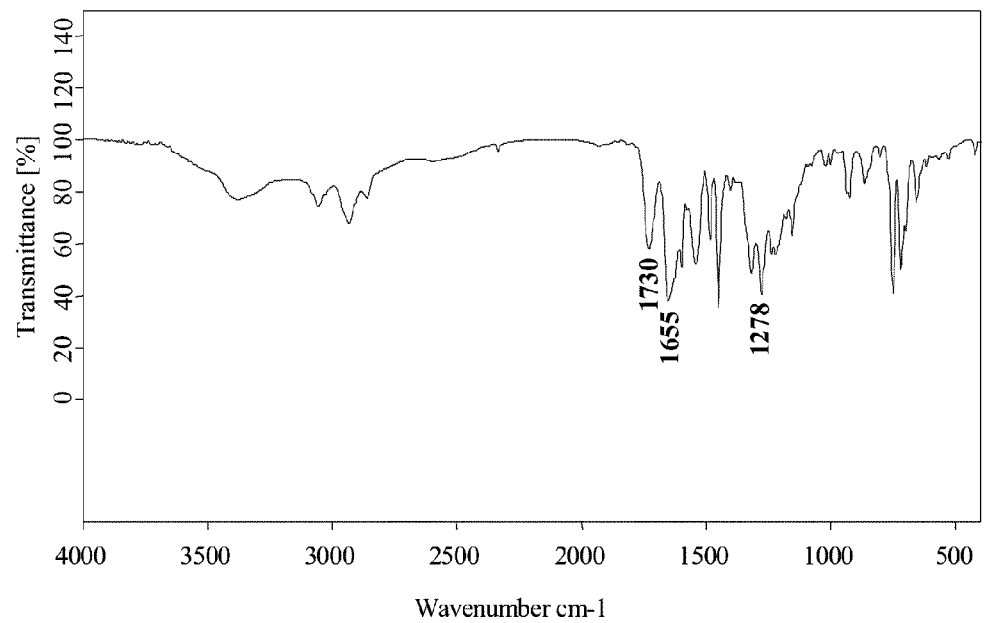
Figure 1D:
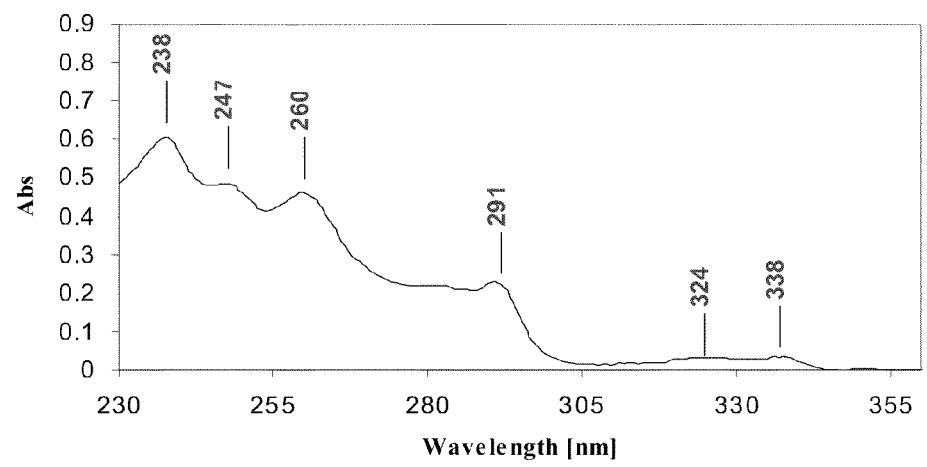
Figure 2A:
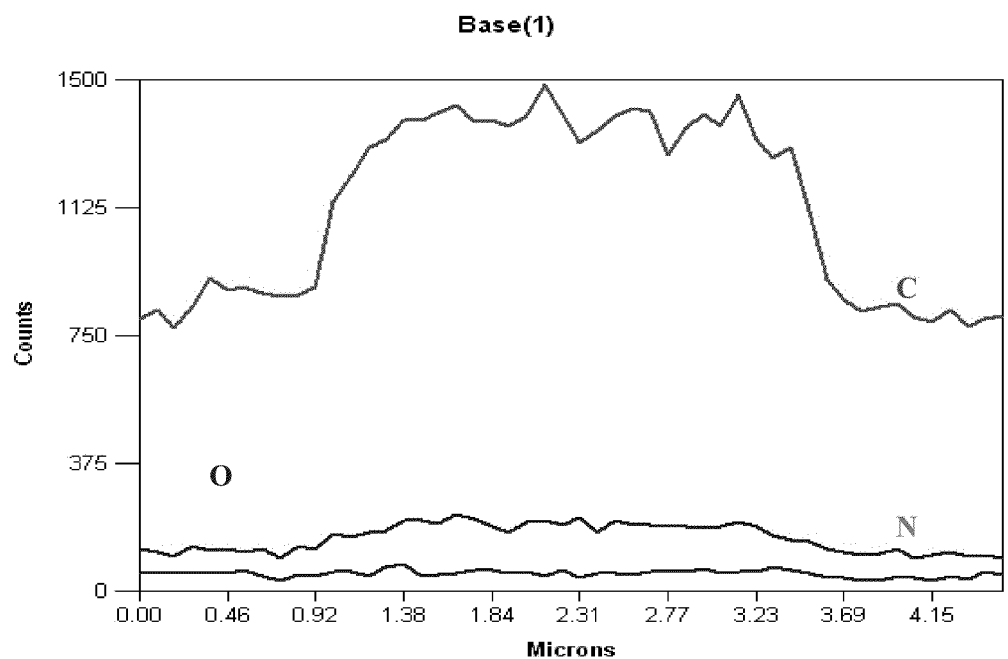
FIGS. 2A-2B show a compositional EDS linescan analysis of the polycarbazole-based benzophenone-containing polymeric particles of Compound 7.
Figure 2B:
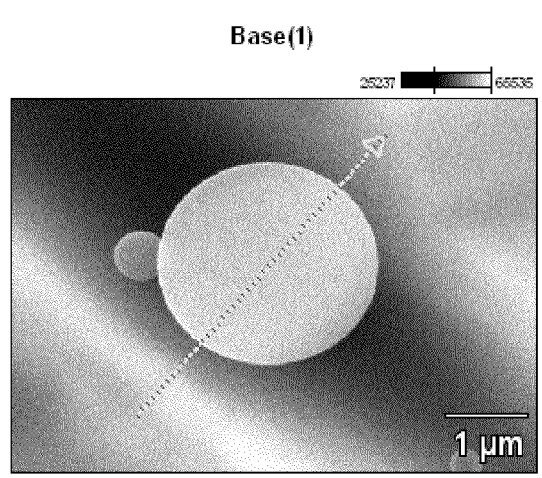

Characterization of Polycarbazole-Based Benzophenone-Containing (poly((S)-6-(4-benzoyl-benzoylamino)-2-carbazol-9-yl-hexanoic acid (7)) Particles SEM and HR-SEM analyses proved the formation of spherical particles (FIGS. 1A-1B). FT-IR and UV-Vis. spectra showed typical transmission/absorbance spectra for polycarbazoles and benzophenone systems in the IR and UV-Vis regions respectively (FIGS. 1C-1D). Linescan analysis confirmed the composition of the observed particles to be based on C, O and N elements (FIGS. 2A-2B).

Example 6

Figure 3:
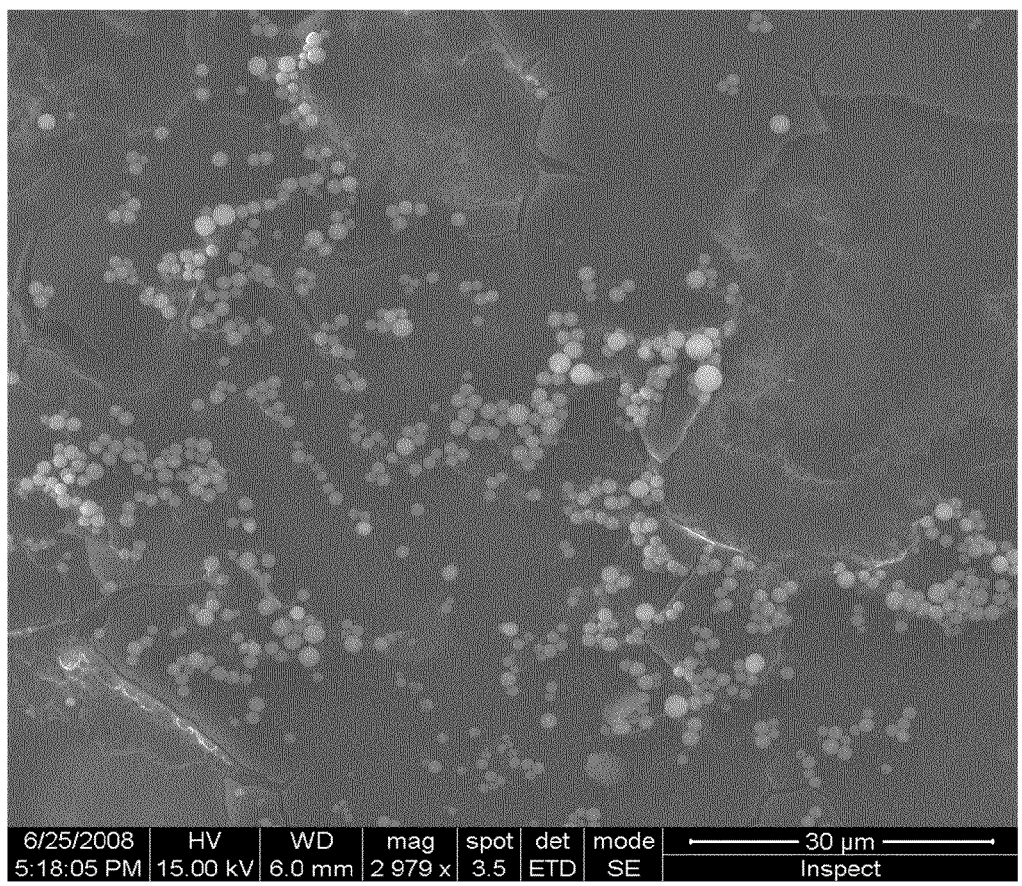
FIG. 3 shows an ESEM image of polycarbazole-based benzophenone-containing particles of Compound 7 onto 2 μm parylene film after UV irradiation.
Figure 4A:
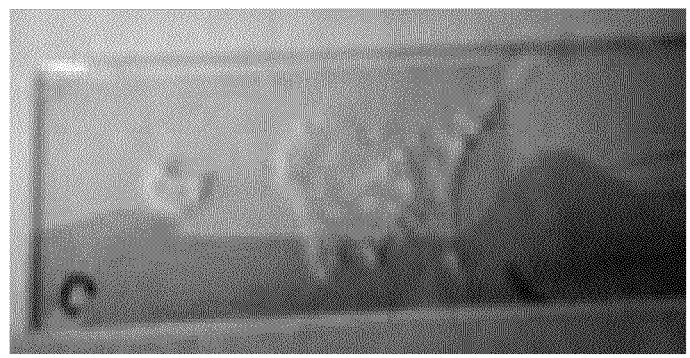
FIG. 4A-4B show photographs of polycarbazole-based benzophenone-containing particles of Compound 7 onto 2 μm parylene film, before (FIG. 4A) and after UV-irradiation (FIG. 4B).
Figure 4B:
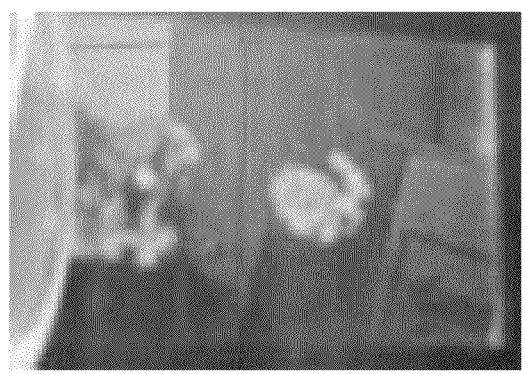

Characterization of 2 μm thick parylene film functionalized by polycarbazoles-Based benzophenone containing (poly((S)-6-(4-Benzoyl-benzoylamino)-2-carbazol-9-yl-hexanoic acid (7))) particles Functionalized films were characterized by XPS, SEM, and ESEM, as well as by visual changes due to film color modifications (digital photographies). ESEM pictures showed the presence of spherical particles on the top-side of the UV-exposed parylene film (FIG. 3). In addition, XPS analysis detected the presence of the N element on the surface of the functionalized film. These combined analyses provided first evidence for the covalent attachment of photoreactive particles onto the parylene film. The additional fact according to which the corresponding particles changed their color from white (deposition step) to yellow (at irradiation completion) after irradiation, confirmed the occurrence of the expected photochemical reaction (FIGS. 4A-4B).

Example 7

Synthesis of 4-azido-N-(3-(triethoxysilyl)propyl)benzamide 27 (PATES)

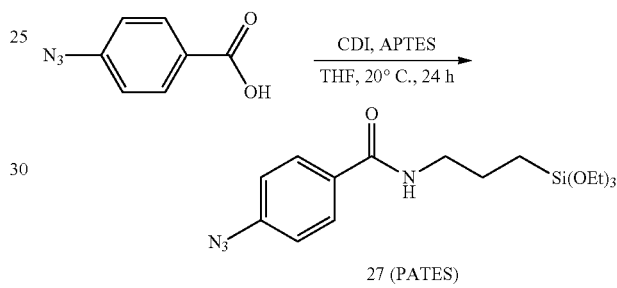

27 (PATES)

The 4-azidobenzoic acid (1.3 g, 8.0 mmol) and 1,1'-imidazole (CDI) (1.29 g, 8.0 mmol) were dissolved in a THF (35 mL) under nitrogen. After stiffing at RT for 2 h 3-aminopropyltriethocarbonyldixysilane (APTES) (1.86 mL, 8.0 mmol) was added to the reaction. Reaction was stirred at the RT overnight. At reaction completion (TLC checking), the medium was concentrated in vacuum affording a yellowish crude solid that was purified by flash chromatography on silica gel (eluent: acetone/n-hexane: 85/15) to give 27 (2.35 g, 6.41 mmol) in 80% yield.

Yellow oil, TLC, $R_f$=0.24 (eluent: acetone/n-hexane: 85/15); $v_{max}$ (KBr easy diff)/$cm^{-1}$ 3322 (NH), 2973 and 2885 (CH stretching), 2927 ($CH_2$ stretching), 2124 (azide), 1639 (C=O amide), 1549 and 1287 (C=C), 1287 (C-0), 1445 and 765 ($CH_2$ bending), 1390 (Si—$OCH_2CH_3$), 1100 (Si—O), 956 (C—O); $δ_H$ $^1H$ NMR (300 MHz; DMSO-$d_6$) 8.48 (1H, br t, NH), 7.91 (2H, d, J=8.7 Hz, Ar—H), 7.17 (2H, d, J=8.7 Hz, Ar—H), 3.74 (6H, q, J=6.9 Hz, O—$CH_2$—$CH_3$), 3.27-3.21 (2H, m, NH—$CH_2$—$CH_2$), 1.64-$\overline{1.54}$ (2H, m, $CH_2$—$CH_2$—$CH_2$), 1.13 $\overline{(9H}$, t, J=6.9 Hz, O—$CH_2$—$CH_3$), 0.61-$\overline{0.56}$ (2H, m, $CH_2$—Si); $δ_C$ $^{13}C$ NMR (75 MHz, $\overline{[D6]}$DMSO, TMS) 165.1 $\overline{(C)}$, 142.0 (C), 131.3 (C), 129.0 (CH), 118.7 (CH), 57.7 ($CH_2$), 42.0 ($CH_2$), 22.7 ($CH_2$), 18.1 ($CH_3$), 7.4 ($CH_2$); UV/Vis $λ_{max}$ (EtOH)/nm (270); HRMS (DCI+CH4) m/z calcd for $C_{16}H_{26}N_4O_4Si$ $(MH)^+$366.4875 found 366.1723.

Example 8

Synthesis of 4-azido-2,3,5,6-tetrafluoro-N-(3-(triethoxysilyl)propyl)-benzamide 28 (PFPATES)

8.1 Synthesis of 4-azido-2,3,5,6-tetrafluorobenzoyl chloride

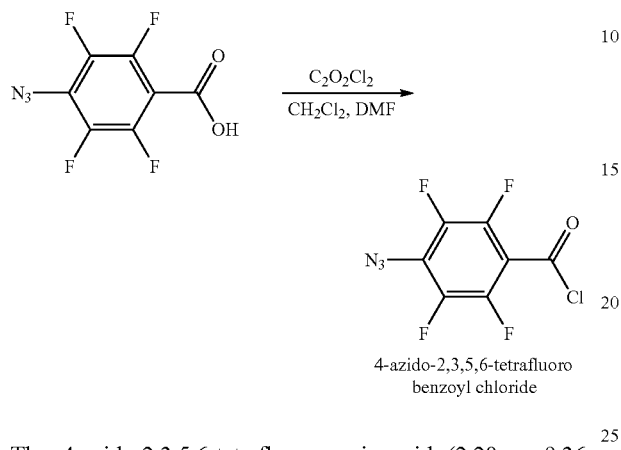

4-azido-2,3,5,6-tetrafluoro benzoyl chloride

The 4-azido-2,3,5,6-tetrafluoroenzoic acid (2.20 g, 9.36 mmol) was dissolved in dry $CH_2Cl_2$ (10 mL). In order to dissolve 4-azido-2,3,5,6-tetrafluoroenzoic acid completely dry DMF (0.3 mL) was added to a reaction mixture. Then oxalyl chloride (3.6 mL, 42.12 mmol) was added and reaction was stirred at RT for 2 h during this time gas evolution was observed. After reaction completion, the solvents were evaporated to give 4-azido-2,3,5,6-tetrafluorobenzoyl chloride as yellow oil that was directly used in the next step without further purification.

8.2 Synthesis of 4-azido-2,3,5,6-tetrafluoro-N-(3-(triethoxysilyl)propyl)-benzamide 28 (PFPATES)

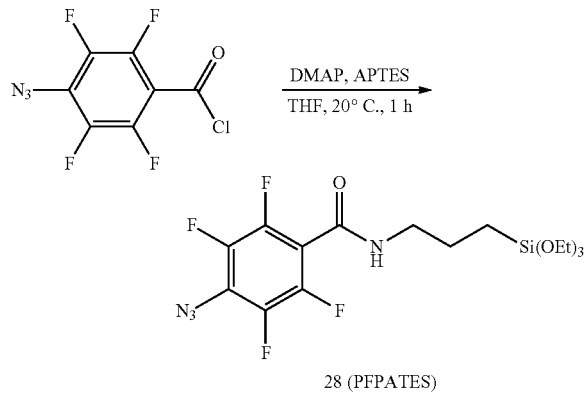

28 (PFPATES)

The 4-azido-2,3,5,6-tetrafluorobenzoyl chloride (2.37 g, 9.36 mmol) was dissolved in dry THF (15 mL) in two neck bottom flask equipped with drying tube. The 4-dimethylaminopyridine (DMAP) (2.44 g, 20 mmol) and APTES (4.42 g, 20 mmol) were dissolved in dry THF (20 mL) and were added to the reaction mixture. The reaction mixture was stirred at RT for 1 h. The reaction mixture was concentrated in vacuum affording a yellowish crude solid that was purified by flash chromatography on silica gel (eluent: ether/n-hexane: 60/40) to give 28 (1.18 g, 2.7 mmol) in 29% yield.

Yellow oil, TLC, Rf=0.37 (eluent: ether/n-hexane: 60/40); $v_{max}$ (KBr easy diff)/cm$^{-1}$ 3280 (NH), 3080 and 2884 (CH stretching), 2930 ($CH_2$ stretching), 2133 (azide), 1650 (C=O amide), 1392 (Si—$OCH_2CH_3$), 1100 (Si—O), 958 (C-0), 777 ($CH_2$ bending); ($\delta_H$ $^1$H NMR (300 MHz, $CDCl_3$) 6.42 (1H, br t, NH), 3.81 (6H, q, J=6.9 Hz, O—$CH_2$—$CH_3$), 3.51-3.44 (2H, m, NH—$CH_2$—$CH_2$), 1.81-1.71 (2H, m, $CH_2$—$CH_2$—$CH_2$), 1.21 (9H, t, J=6.9 Hz, O—$CH_2$—$CH_3$), 0.73-0.66 (2H, m, $CH_2$—Si); $\delta_C$ $^{13}$C NMR (75 MHz; $CDCl_3$) 157.4 (C), 145.7 (C), 142.1 (C), 138.7 (C), 112.1 (C), 58.5 (CH2), 42.4 (CH2), 22.5 (CH2), 18.2 (CH3), 7.6 (CH2); $\delta_F$ $^{19}$F NMR (188 MHz; $CDCl_3$) 141.3-141.5 (m, 2F), 150.9-151.1 (m, 2F); UV/Vis $\lambda_{max}$ (EtOH)/nm (260); HRMS (DCI+$CH_4$) m/z calcd for $C_{16}H_{22}F_4N_4O_4Si$ (MH-EtOH)$^+$ 393.3810 found 393.1006.

Example 9

Synthesis of 4-benzoyl-N-(3-(triethoxysilyl)propyl)benzamide 29 (BphTES)

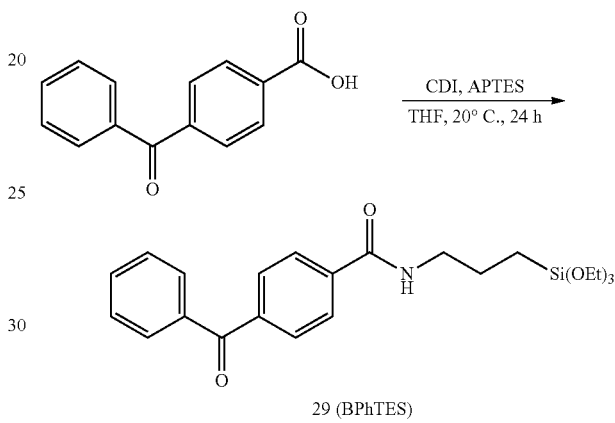

29 (BPhTES)

4-benzoylbenzoic acid (2.26 g, 10.0 mmol) and CDI (1.62 g, 10.0 mmol) were dissolved in a dry THF (40 mL) in two neck bottom flask equipped with drying tube. After stirring at RT for 2 h APTES (2.32 mL, 10.0 mmol) was added to reaction. Reaction was stirred at the same temperature during 24 h. At reaction completion (TLC checking), the medium was concentrated in vacuum affording a yellowish crude solid that was purified by flash chromatography on silica gel (eluent: acetone/n-hexane: 85/15) to give 29 (2.54 g, 5.91 mmol) in 59% yield.

White solid, TLC, Rf=0.68 (eluent: acetone/n-hexane: 85/15); m.p. 90-91° C.; $v_{max}$ (KBr easy diff)/cm$^{-1}$ 3326 (NH), 2975 and 2885 (CH stretching), 2928 ($CH_2$ stretching), 1663 (C=O ketone), 1631 (C=O amide), 1553 (C=C), 1445 and 790 ($CH_2$ bending), 1390 (Si—$OCH_2CH_3$), 1300 (C—H bending), 1278 and 1108 (C-O), 1167 (C—N), 1080 (Si—O) cm$^{-1}$; $\delta_H$ $^1$H NMR (300 MHz, [$D_6$] DMSO, TMS) 8.68 (1H, br t, NH), 8.02-7.98 (2H, m, Ar—H), 7.78-7.68 (5H, m, Ar—H), 7.61-7.56 (2H, m, Ar—H), 3.77 (6H, q, J=9.6 Hz, O—$CH_2$—$CH_3$), 3.35-3.25 (2H, m, NH—$CH_2$—$CH_2$), 1.67-1.57 (2H, m, $CH_2$—$CH_2$—$CH_2$), 1.15 (9H, t, J=9.6 Hz, O—$CH_2$—$CH_3$), 0.65-0.59 (2H, m, $CH_2$—Si); $\delta_C$ $^{13}$C NMR (75 MHz, [$D_6$] DMSO, TMS) 195.4 (C), 165.3 (C), 139.0 (C), 138.0 (C), 136.7 (C), 133.0 (CH), 129.7 (CH), 129.5 (CH), 128.7 (CH), 127.3 (CH), 57.7 ($CH_2$), 42.1 ($CH_2$), 22.7 ($CH_2$), 18.2 ($CH_3$), 7.5 ($CH_2$); UV/Vis $\lambda_{max}$ (EtOH)/nm (260); HRMS (DCI+$CH_4$) m/z calcd for $C_{23}H_{31}NO_5Si$ (MH)$^+$ 429.5814 found 430.248.

Example 10

Synthesis of Photoreactive Hybrid Silica NPs

The photoreactive organosilanes PA-based triethoxysilane (PATES) 27, PFPA-based triethoxysilane (PFPATES) 28, and BPh-based triethoxysilane (BPhTES) 29 (H. Li and G. McGall, *Frontiers in Biochip Technology*, Springer, 2006) were synthesized from the corresponding photoreactive carboxylic acid derivatives by their reaction with 3-aminopropyltriethoxysilane (APTES) to form amide bond.

Hybrid photoreactive $SiO_2$ NPs bearing photoreactive groups were prepared by a one-pot hydrolytic co-condensation of photoreactive organosilanes 27-29 (10% molar) and tetraethyl orthosilicate (TEOS) using the well-known Stöber sol-gel method to produce $SiO_2$@PA, $SiO_2$@PFPA, and $SiO_2$@BPh NPs respectively (Scheme 5). The bare $SiO_2$ NPs were prepared by the same procedure using TEOS without addition of any photoreactive organosilane.

Example 11

Characterization of Hybrid Photoreactive $SiO_2$ NPs

Figure 5A:
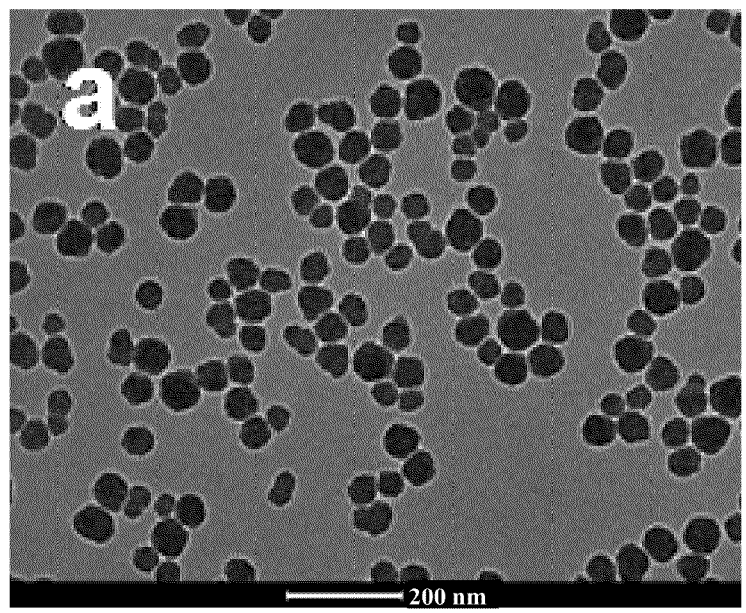
FIGS. 5A-5C show TEM images of $SiO_2$@PA (FIG. 5A), $SiO_2$@PFPA (FIG. 5B), and $SiO_2$@BPh (FIG. 5C) (all scale bars are 200 nm)
Figure 5B:
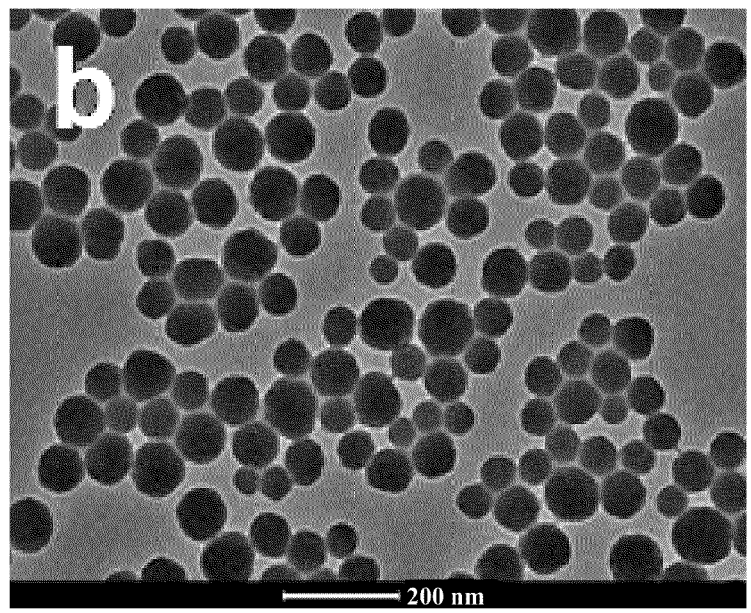
Figure 5C:
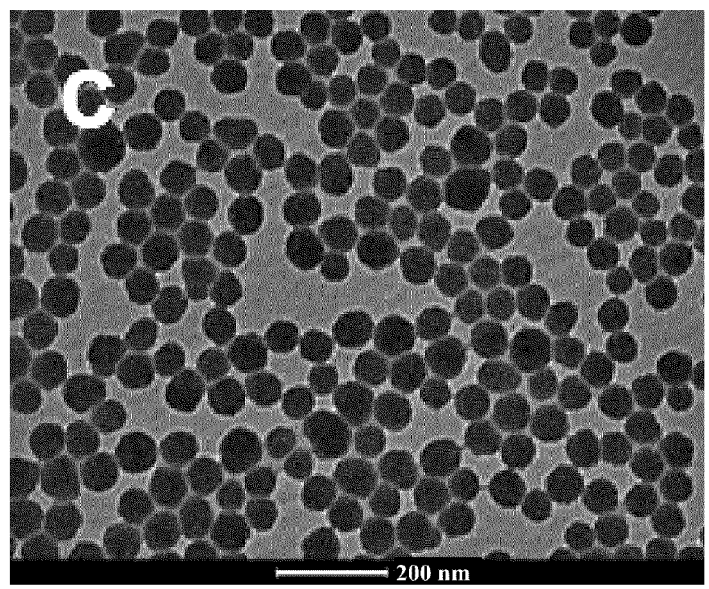
Figure 5D:
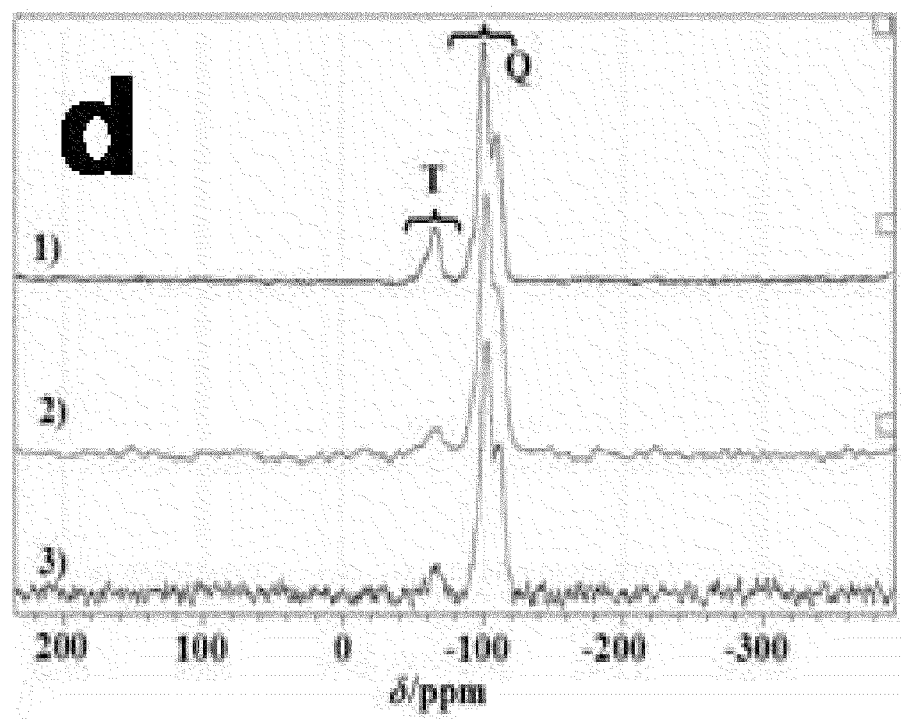
FIG. 5D shows $^{29}Si$ CP/MAS NMR spectra of the 1) $SiO_2$@PA, 2) $SiO_2$@BPh, and 3) $SiO_2$@PFPA nanoparticles.

The size and morphology of the three types of hybrid photoreactive $SiO_2$ NPs as well as of bare $SiO_2$ NPs were determined using transmission electron microscopy (TEM) and dynamic light scattering (DLS) measurements. TEM images indicated that all three types of hybrid photoreactive $SiO_2$ NPs have a spherical morphology (FIGS. 5A-5C) with an average size of 52.1±9.0, 80.8±14.6, and 63.9±6.1 nm (Table 4, average measurement of 100 NPs from TEM images using Image J software) for $SiO_2$@PA, $SiO_2$@PFPA, and $SiO_2$@BPh NPs, respectively.

TABLE 4

Characterization of photoreactive and bare silica nanoparticles

| Sample | TGA (%)[a] | DLS (nm)[b,c] | ζ-pot. (mV)[c,d] | Size (nm)[e] |
|---|---|---|---|---|
| $SiO_2$ | 12.96 | 149.0 | −48.7 | 141.4 ± 10.6 |
| $SiO_2$@PA | 21.39 | 107.3 | −41.2 | 52.1 ± 9.0 |
| $SiO_2$@PFPA | 20.09 | 129.6 | −36.5 | 80.8 ± 14.6 |
| $SiO_2$@BPh | 19.21 | 102.8 | −40.8 | 63.9 ± 6.1 |

[a]Weight loss,
[b]Average size,
[c]EtOH dispersion,
[d]ζ-potential,
[e]average size measurement of 100 NPs from TEM images using Image J software.

In contrast, bare $SiO_2$ NPs possess a larger average size of 141.4±10.6 nm. This phenomenon originates from co-condensation process itself. In other words, during the hydrolysis of any photoreactive organosilane, the lack of propagating alkoxy groups hinders the particle growth, which leads to a decrease in sizes (Lee et al., *Small*, 2008, 4, 143-152).

The colloidal stability of ethanolic dispersions of hybrid photoreactive $SiO_2$ NPs was examined by DLS and ζ-potentials measurements (Table 4). Since DLS provides information concerning the hydrodynamic radius of the particle, the average sizes of all NPs measured by DLS are larger than the average sizes determined by TEM. $SiO_2$@PA, $SiO_2$@PFPA, $SiO_2$@BPh NPs, and bare $SiO_2$ NPs have ζ-potentials values of −41.2, −36.5, −40.8, and −48.7 mV respectively, this indicates that all these NPs form stable dispersions.

Figure 6A:
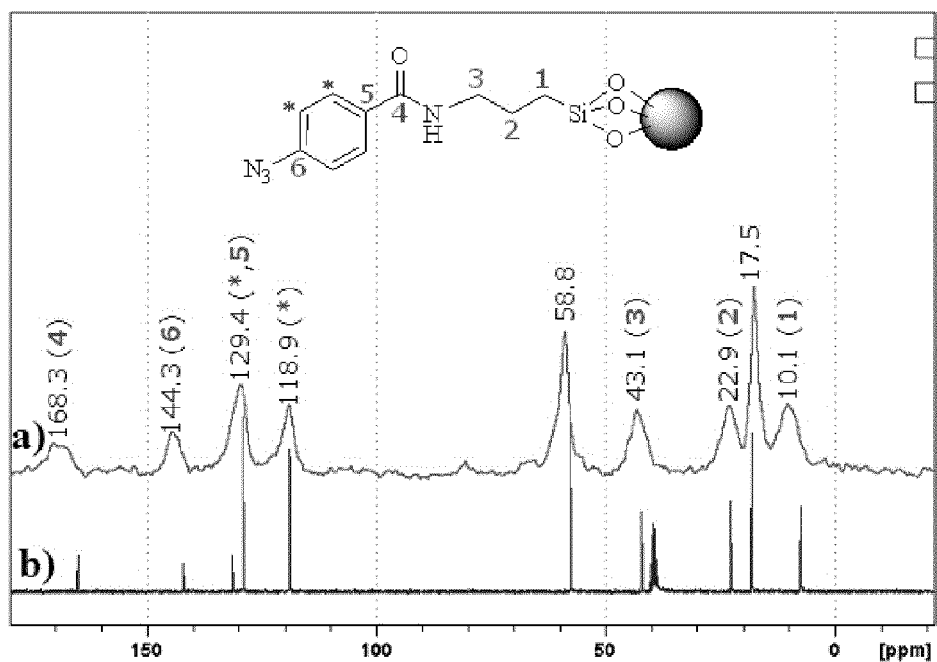
FIGS. 6A-6C show $^{13}C$ CP/MAS NMR (a) and $^{13}C$ NMR spectra (b) of $SiO_2$@PA, $SiO_2$@PFPA, and $SiO_2$@BPh nanoparticles and of PATES, PFPATES, and BPhTES, respectively.
Figure 6B:
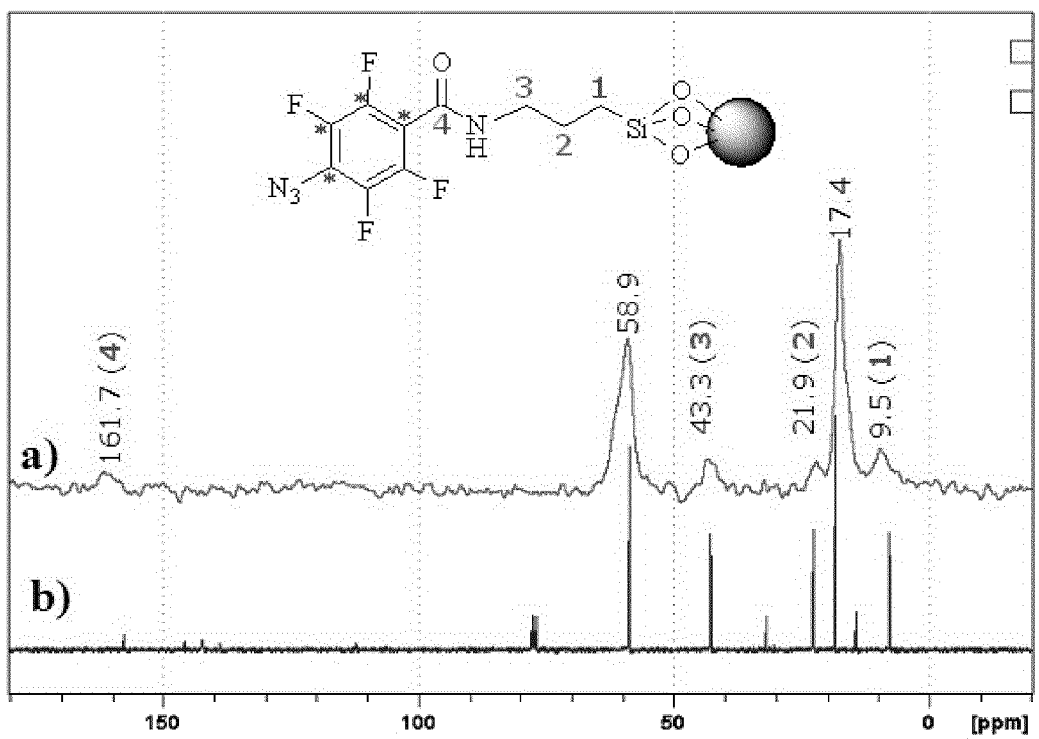
Figure 6C:
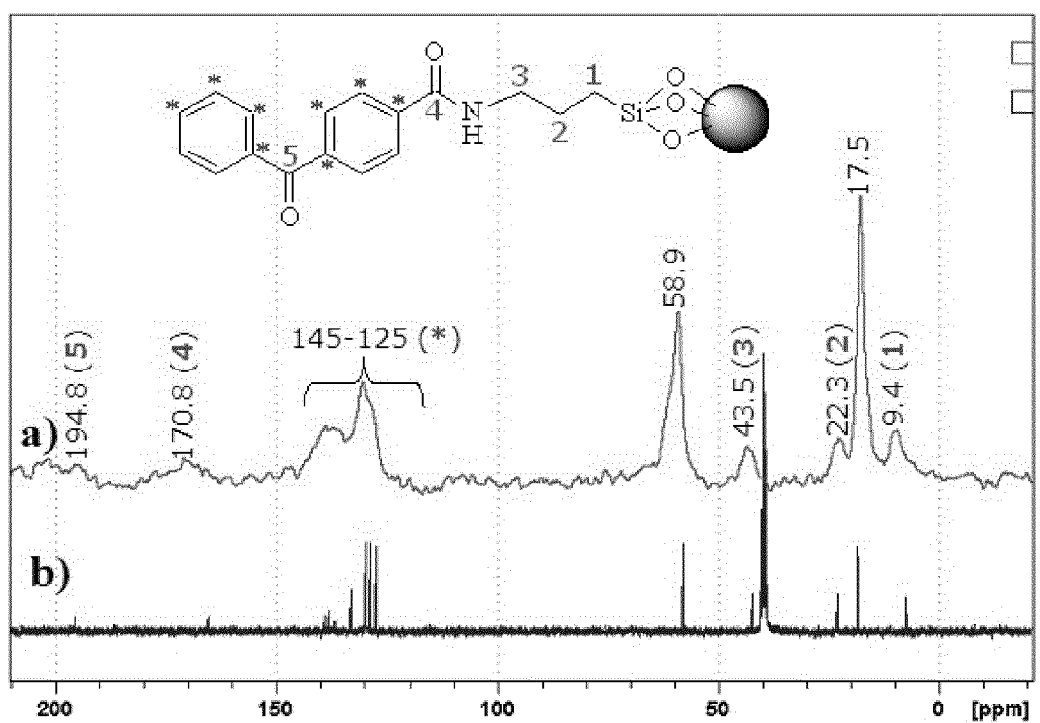
Figure 7A:
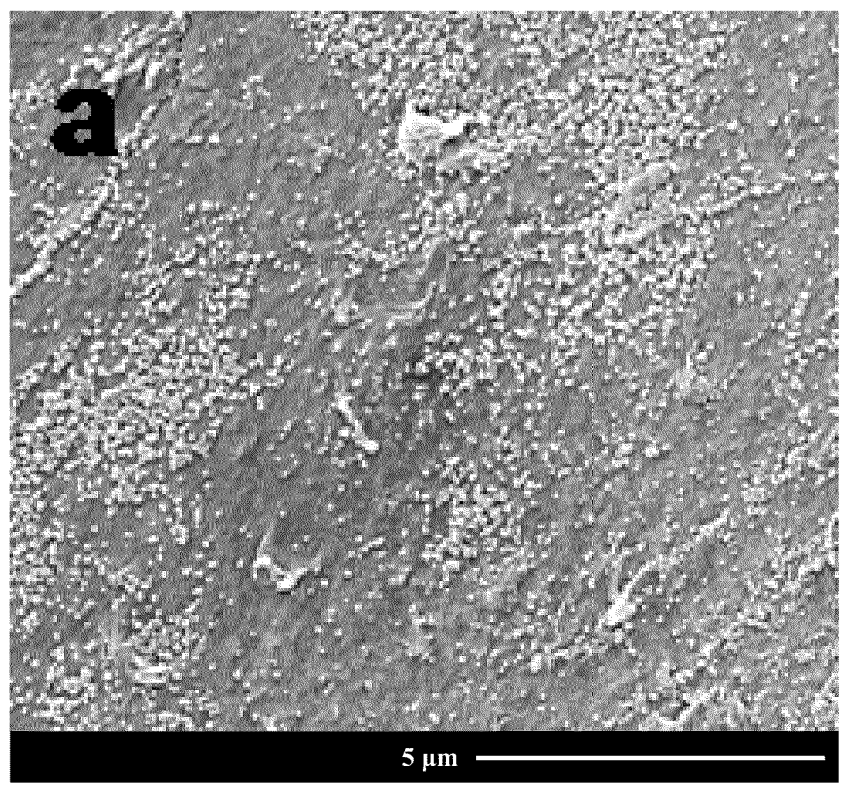
FIGS. 7A-7D show SEM images of parylene C after UV-mediated reaction with $SiO_2$@PA (FIG. 7A), $SiO_2$@PFPA (FIG. 7B), $SiO_2$@BPh (FIG. 7C), or $SiO_2$ (FIG. 7D) particulate systems (all scale bars are 5 μm).
Figure 7B:
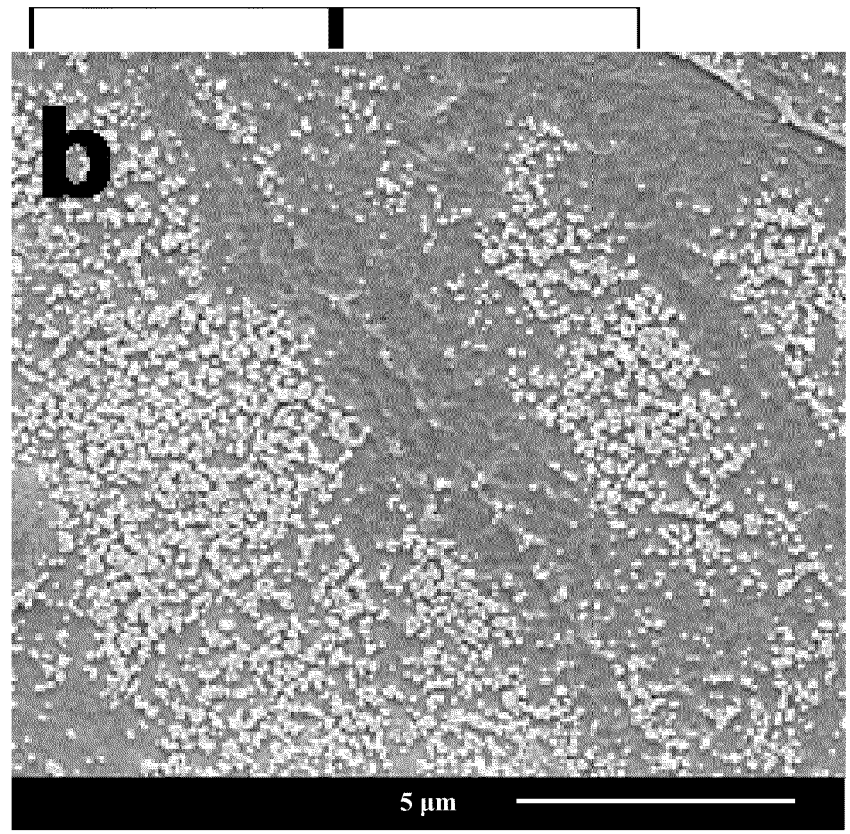
Figure 7C:
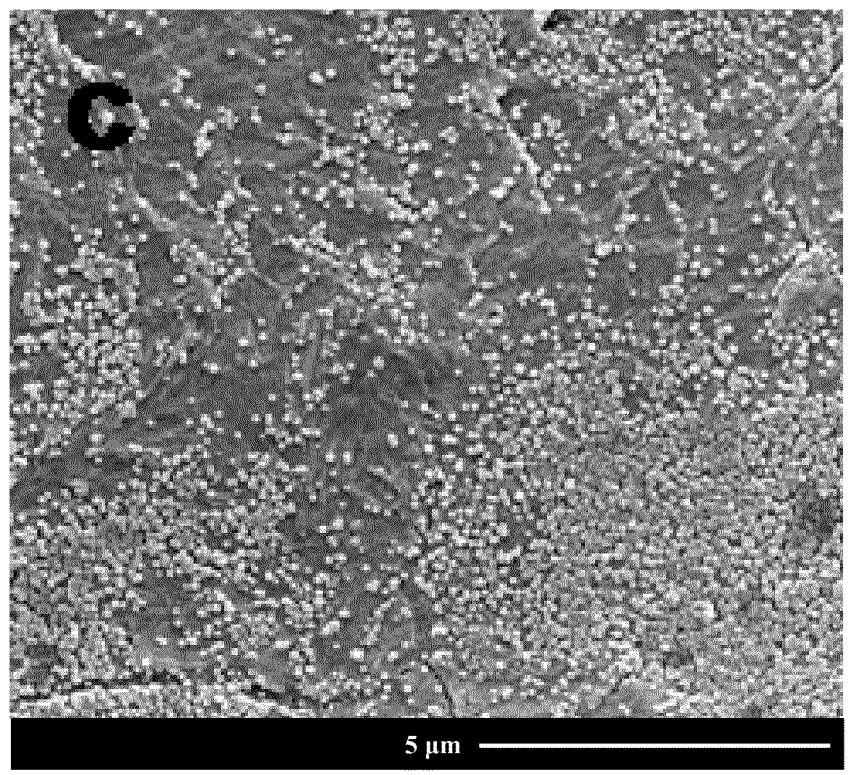
Figure 7D:
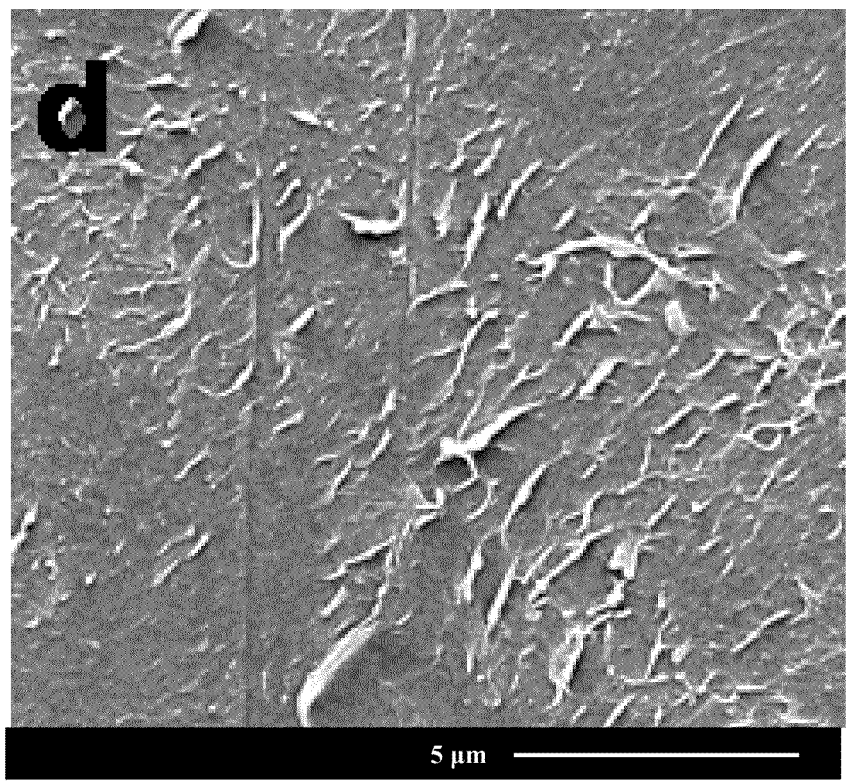
Figure 8A:
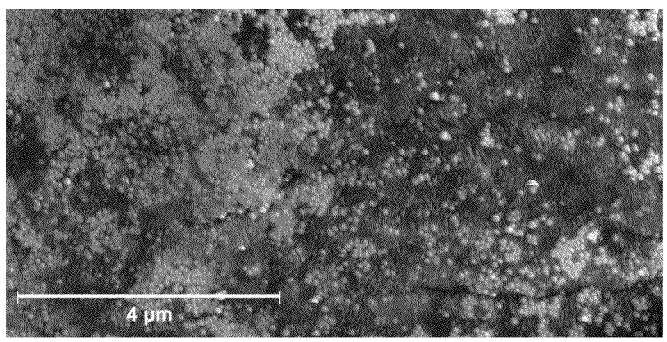
FIGS. 8A-8D show AFM images of parylene C after UV-mediated reaction using $SiO_2$@PA (FIG. 8A), $SiO_2$@PFPA (FIG. 8B), $SiO_2$@BPh (FIG. 8C), or $SiO_2$ (FIG. 8D) particulate systems (all scale bars are 4 μm).
Figure 8B:
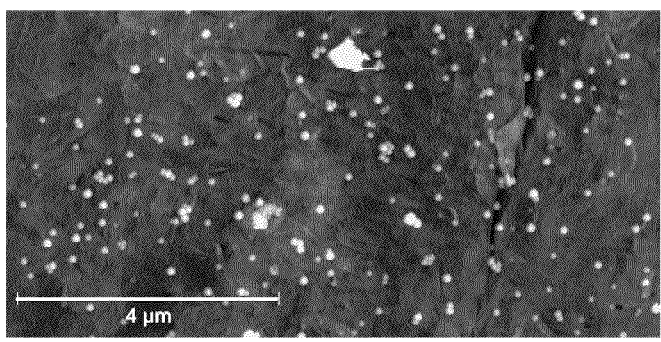
Figure 8C:
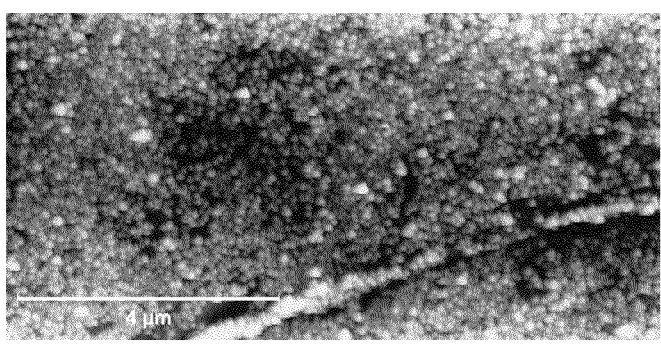
Figure 8D:
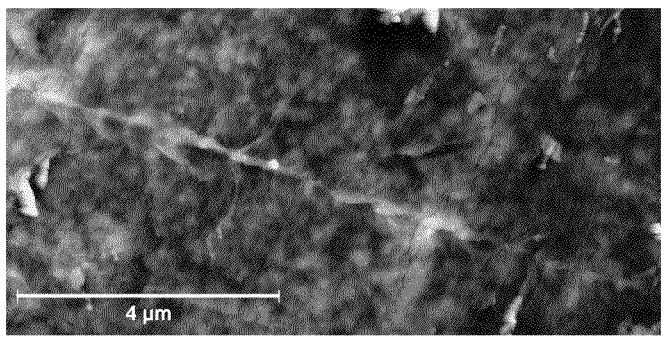

The incorporation of photoreactive organosilanes 27-29 was studied using solid state $^{29}Si$ and $^{13}C$ cross polarization-magic angle spinning (CP/MAS) NMR (FIG. 5D and FIGS. 6A-6C, respectively). The $^{29}Si$ NMR profiles extended in two regions −80 to −120 ppm and −50 to −80 ppm, corresponding to siloxane groups units $Q^x$ ($Q^x$, $Si(OSi)_x(OH)_{4-x}$) and silicon groups $T^x$ ($T^x$, $\overline{C}$ $\overline{Si}(OSi)_x(OH)_{3-x}$), respectively. The signals centered at −68 ppm (denoted T) are representative for T units confirming the presence of photoreactive groups on the $SiO_2$ surface. The signals at −80 to −120 ppm region are assigned as Q signals, which originate from $SiO_2$ matrix. FIG. 6A demonstrates a good correlation between the $^{13}C$ CP/MAS NMR spectrum of $SiO_2$@PA NPs (a) and the $^{13}C$ NMR (75 MHz; [D$_6$]DMSO) spectrum of 27 (PATES) (b). It can be clearly seen that all peaks denoted as 1-6 appear in both spectra. The two peaks appearing at 17.5 and 58.8 ppm are ascribed to ethoxy groups of 27. In the spectrum of $SiO_2$@PA NPs they appear due to unhydrolized ethoxy groups in hybrid $SiO_2$ matrix. The $SiO_2$@PFPA and $SiO_2$@BPh NPs were also examined by $^{13}C$ CP/MAS NMR technique and showed similar characterizations, FIGS. 6B-6C, respectively.

The thermogravimetric analysis (TGA) (25-800° C. temperature profile, heating rate of 10° C./min, air) confirms the successful incorporation of photoreactive silanes 27-29 into hybrid $SiO_2$ matrix. All hybrid photoreactive $SiO_2$ NPs had higher weight losses than the bare $SiO_2$ NPs as it can be seen from Table 4. The weight loss of bare $SiO_2$ NPs originates from unhydrolized alkoxy groups, water and ethanol molecules trapped in silica matrix. Moreover, all ethanolic dispersions of $SiO_2$@PA, $SiO_2$@PFPA, and $SiO_2$@BPh NPs have a strong UV absorbance at 270, 260, and 260 nm, respectively, which originated from the incorporated photoreactive groups. Finally, the presence of the azide group in $SiO_2$@PA and $SiO_2$@PFPA NPs was detected by FTIR at 2100 $cm^{-1}$.

Next, parylene C (PC) films were modified with $SiO_2$@PA, $SiO_2$@PFPA, and $SiO_2$@BPh NPs using UV irradiation to produce PC—$SiO_2$@PA, PC—$SiO_2$@PFPA, and PC—$SiO_2$@BPh respectively (Scheme 6). In order to prove that the attachment of the hybrid photoreactive $SiO_2$ NPs on to PC films arose from the photochemical reaction a control experiment for PC modification using bare $SiO_2$ NPs was performed to yield PC—$SiO_2$.

Figure 9:
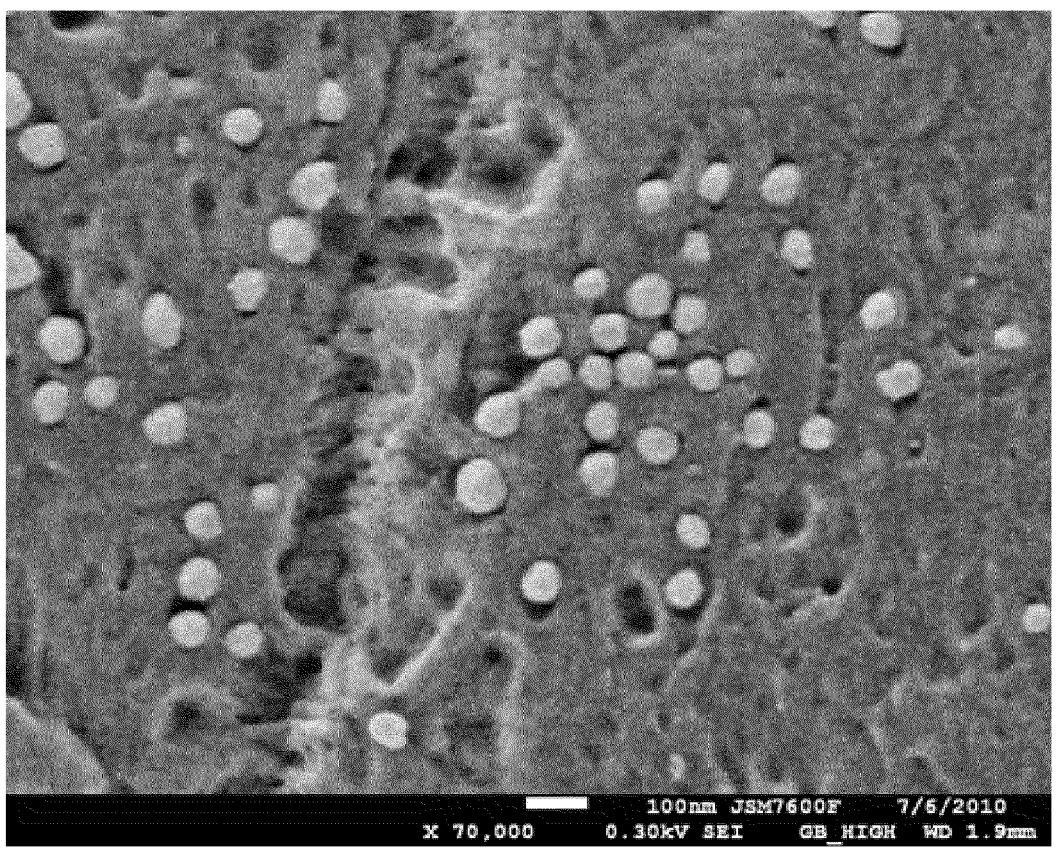
FIG. 9 shows an FE-SEM image of a PC—$SiO_2$@PFPA modified film (the analysis was performed without gold conducting coating).
Figure 10A:
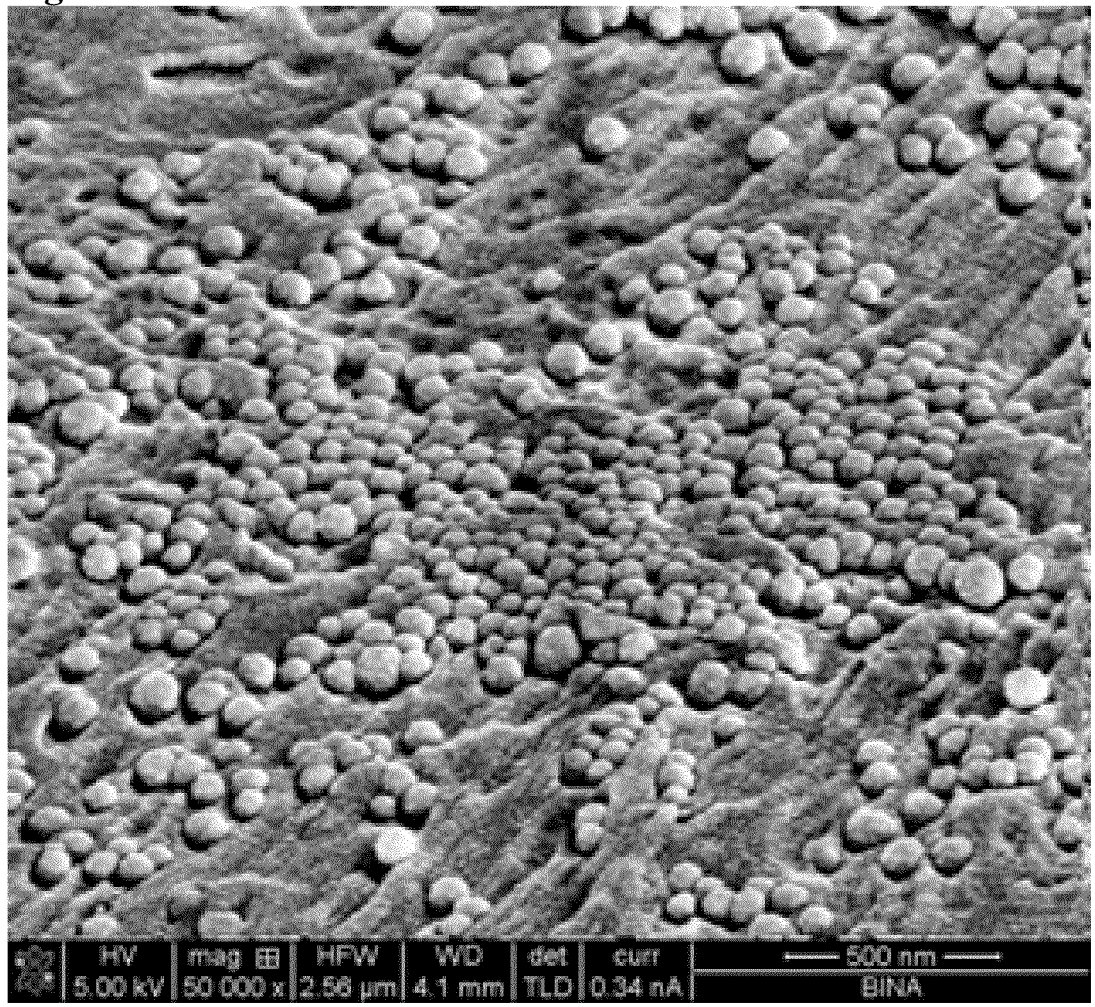
FIGS. 10A-10C show SEM tilt images of parylene C films functionalized with $SiO_2$@PFPA (FIG. 10A), $SiO_2$@PA (FIG. 10B), or $SiO_2$@BPh (FIG. 10C) nanoparticles.
Figure 10B:
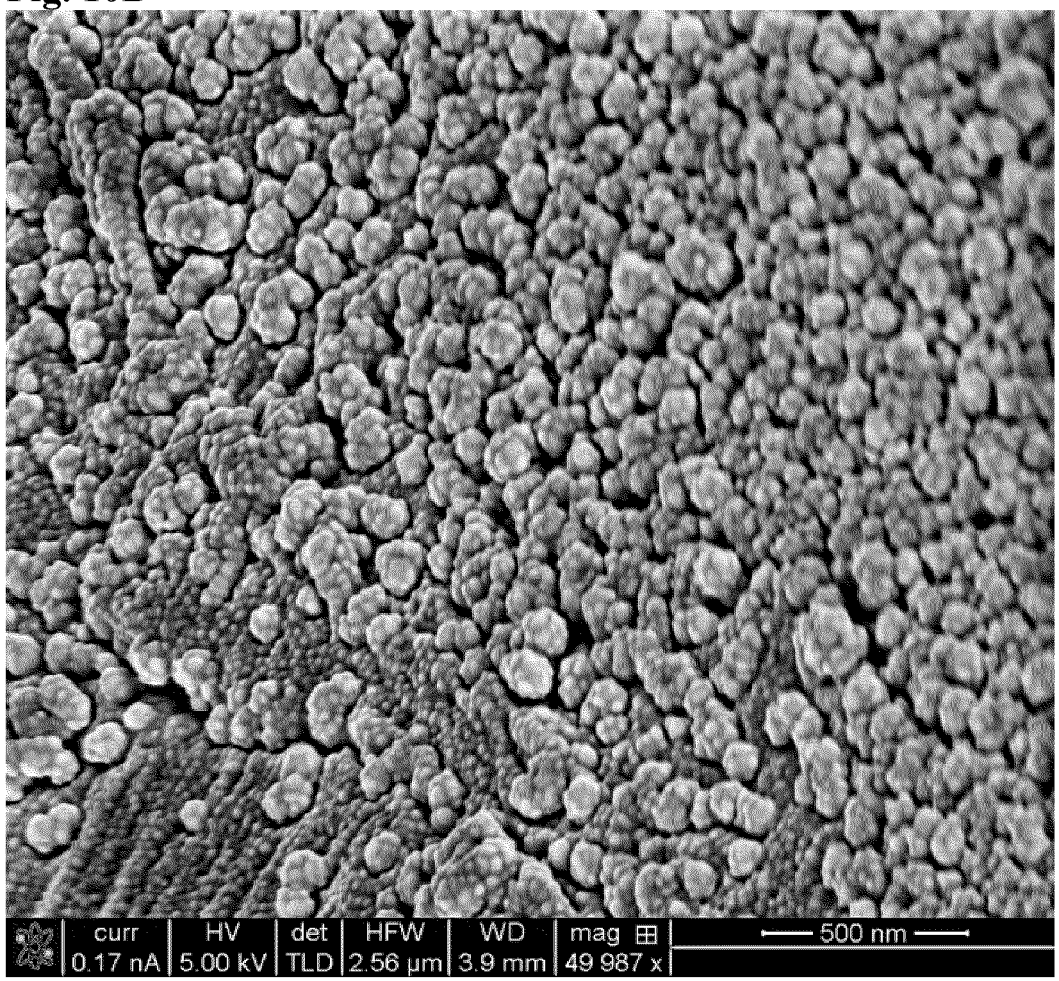
Figure 10C:
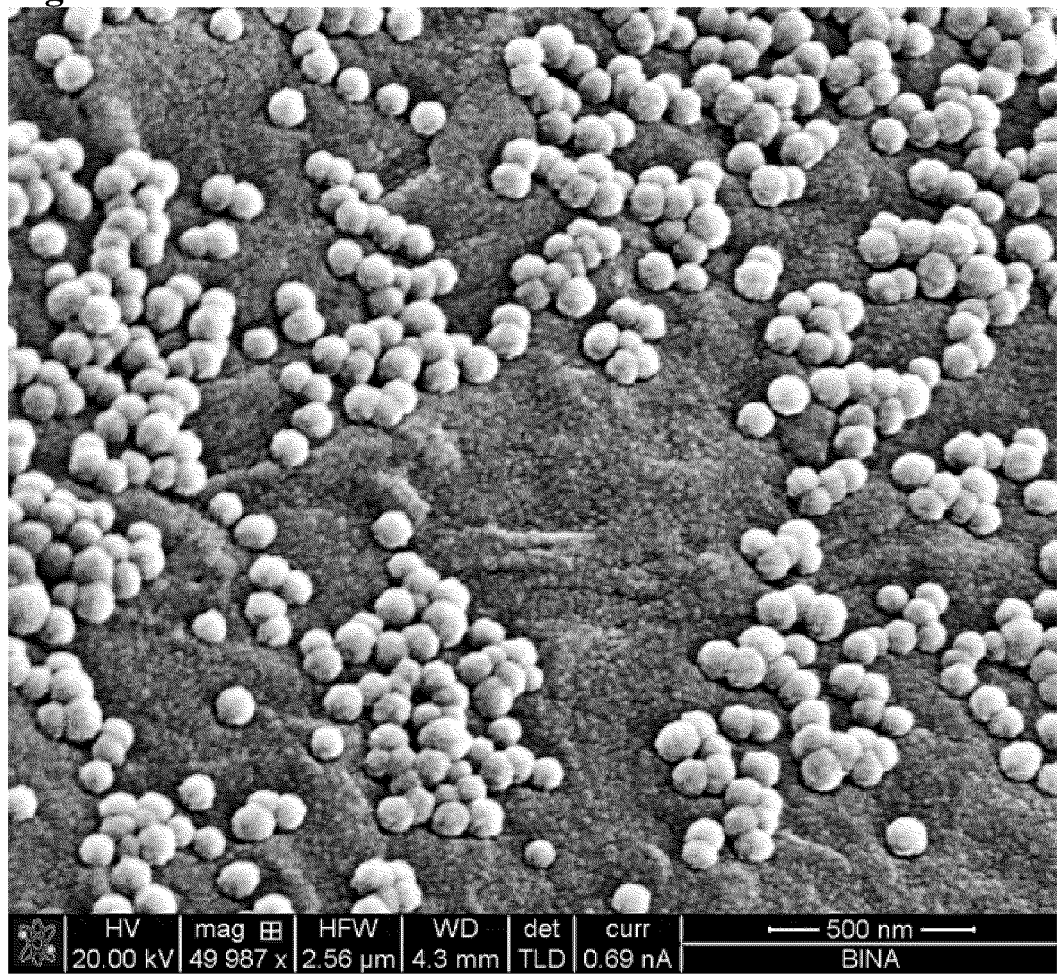
Figure 11A:
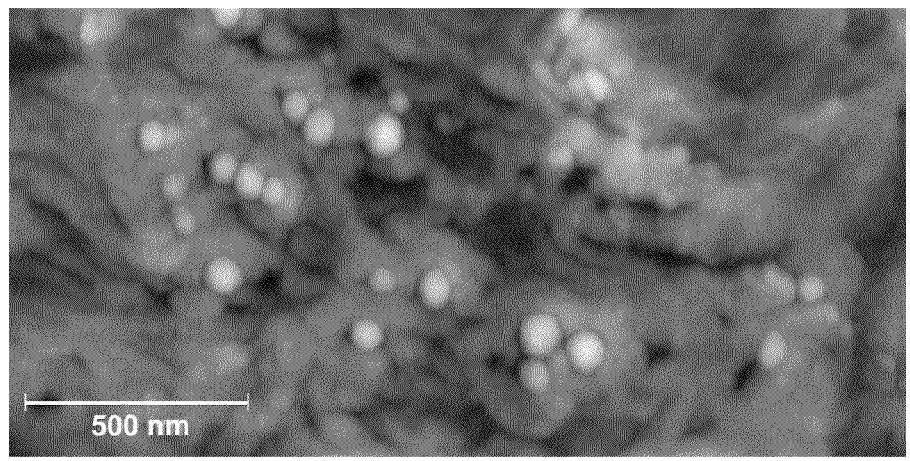
FIGS. 11A-11C show AFM images of functionalized parylene C (PC) films.
Figure 11B:
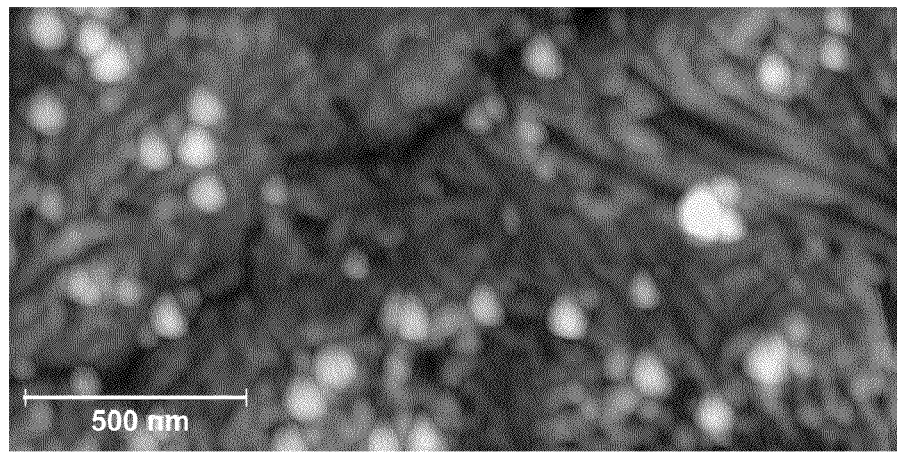
Figure 11C:
Figure 12A:
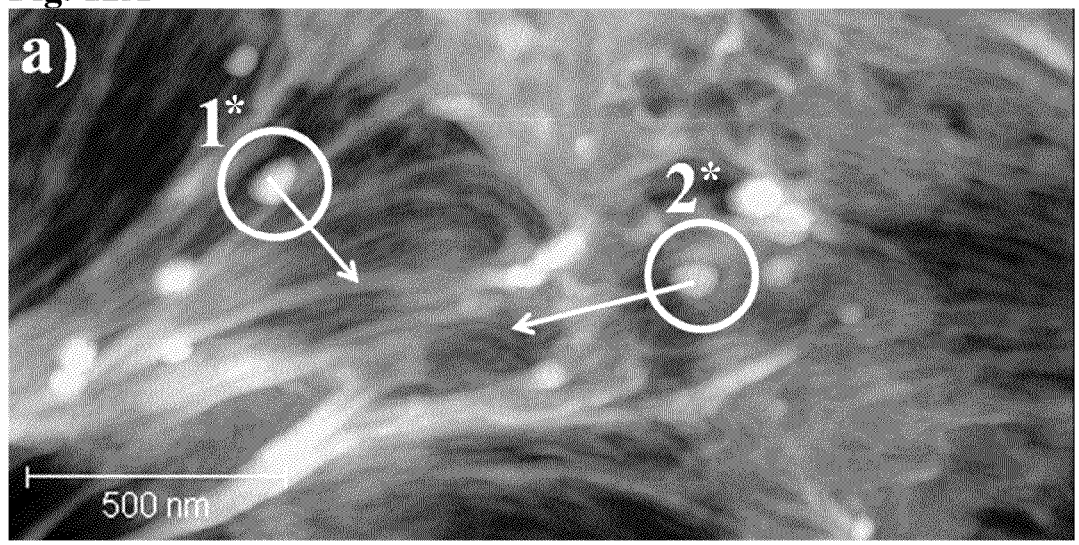
FIGS. 12A-12B show AFM images of a PC—SiO$_2$@PA film before (FIG. 12A) and after (FIG. 12B) nanoparticle manipulations. Particle 1* was moved with a vertical tip depth of Z=−40 nm and particle 2* with Z=−30 nm while both particles did not moved disclosing tip-caused scratches in both cases.
Figure 12B:
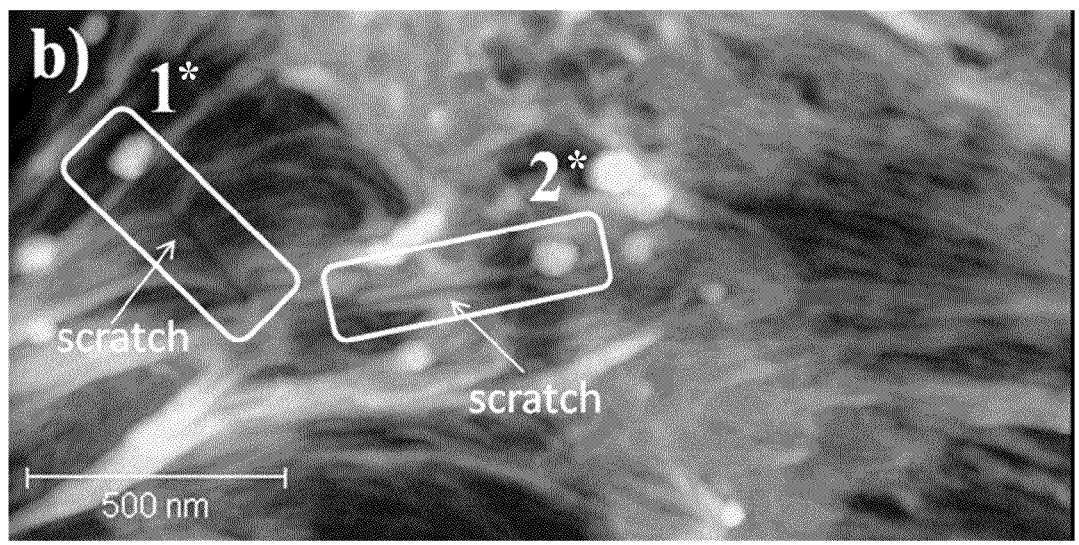
Figure 13A:
FIGS. 13A-13B show AFM image of PC—SiO$_2$@PFPA film before (FIG. 13A) and b after (FIG. 13B) nanoparticle manipulations. Particle 1* was moved with a vertical tip depth of Z=−20 nm and Z=−30, particle 2* with Z=−30 nm and particle 3* with Z=−40 nm; all three particles did not moved and a tip scratch can be seen for 3* and a hole in the place where the tip stopped for 2*.
Figure 13B:
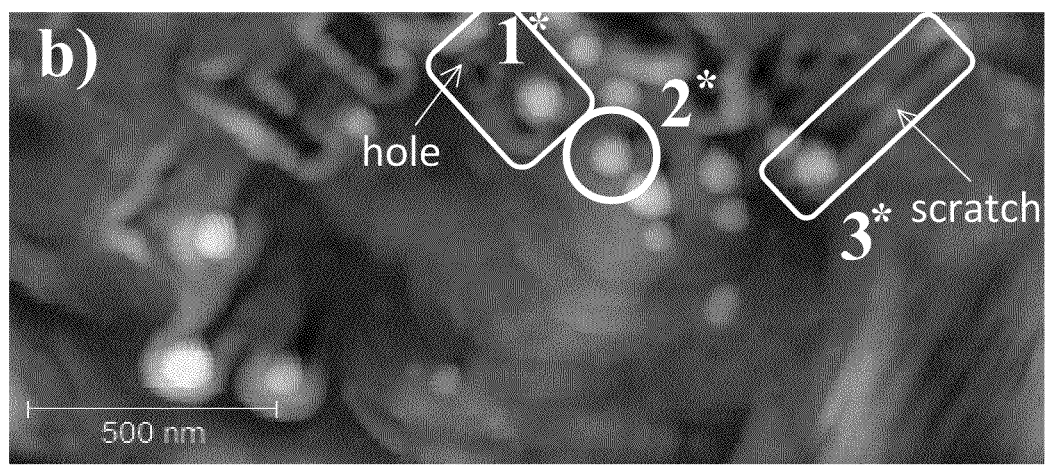
Figure 14A:
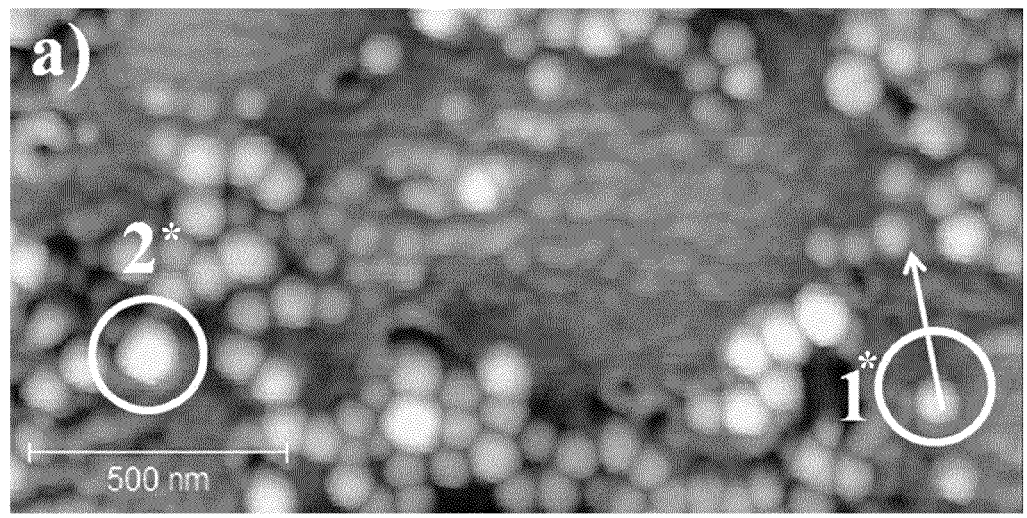
FIGS. 14A-14B show AFM images of a PC—SiO$_2$@BPh film before (FIG. 14A) and after (FIG. 14B) nanoparticle manipulations. Particle 1* was moved with vertical tip depths of Z=−30 and −40 nm and particle 2* with Z=−40 nm, Z=−50 nm and Z=−60 nm; both particles did not moved and a tip-caused scratch can be seen for 1*.
Figure 14B:
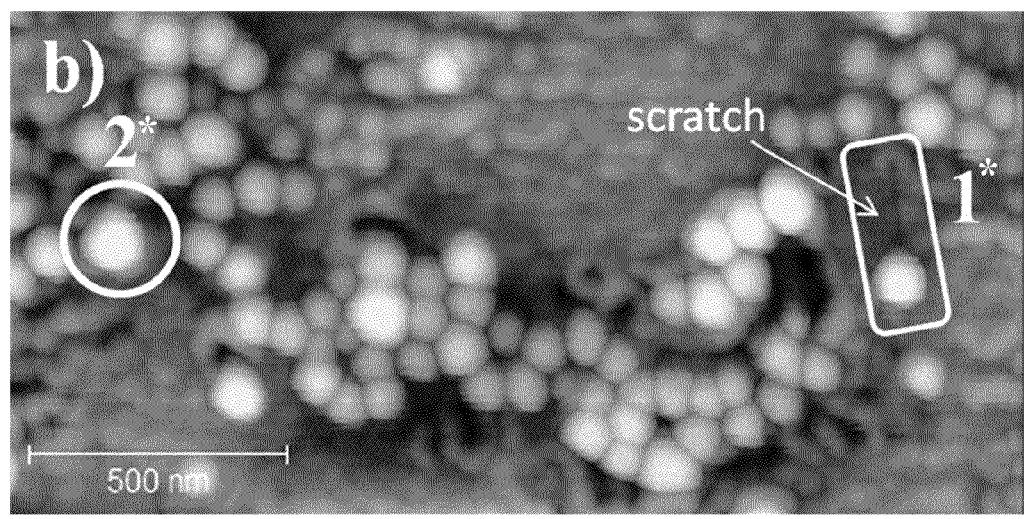

The topography of the $SiO_2$ functionalized parylene films was investigated using scanning electron microscope (SEM) and atomic force microscopy (AFM). It can be clearly seen from SEM (FIGS. 7A-7D) and AFM (FIGS. 8A-8D) images that there is a homogenous coverage of the parylene film by $SiO_2$ NPs for all three types of photoreactive NPs, while no particles were detected in the case of the bare $SiO_2$ NPs. Moreover, field emission scanning electron microscope (FE-SEM) and AFM images demonstrate partial penetration of NPs into the film for $SiO_2$@PA NPs (FIG. 9 and FIG. 11B, respectively). Similar behavior was discovered for $SiO_2$@PFPA and $SiO_2$@BPh NPs (FIGS. 10A, 10C, 11A and 11C).

In order to demonstrate the covalent attachment of the hybrid photoreactive $SiO_2$ NPs into PC films, NP manipulation by mechanical pushing using AFM was performed (Hansen et al., *Nanotechnology*, 1998, 9, 337-342). When the irradiation was performed for 4 h, particles could not be moved and a scratch was formed on the surface of the parylene film in the place where the AFM tip moved during the mechanical manipulation (FIGS. 12A-12B, 13A-13B, and 14A-14B). Scratch formation is evidence of the physical contact between the tip and the surface of the film indicating that there was a physical contact between the tip and the bottom part of the particle. In contrast, when the irradiation was performed for 2 h in the case $SiO_2$@PFPA NPs, some of the particles could be moved. It is important to mention that the highest concentration of particles was observed in the case of $SiO_2$@BPh NPs. These observations can be explained by the different possible mechanisms of the photochemical reactions. In the case of UV-irradiated $SiO_2$@PA and $SiO_2$@PFPA NPs, singlet and triplet nitrene species are formed. These reactive species can react with C—H bonds of the ethyl linker between the rings in the PC backbone through both abstraction (triplet) and insertion (singlet) reactions (Scheme 7a). Abstraction reactions lead to the sole formation of radicals on the parylene backbone that can lead to chain reactions (cross linkage and bond cleavage). In contrast, insertion reactions are termination steps. When SiO$_2$@BPh NPs are used, biradicaloid triplet excited species are formed upon UV irradiation. These triplet species also react in hydrogen abstraction reactions to form a ketyl radical and a radical from parylene (Scheme 7b). Such radicals on the parylene backbone enable the partial penetration of photoreactive SiO$_2$ NPs into the film via cross linkage and bond cleavage. Finally and after the particle penetration, bonds can be formed between the radicals on the parylene film and those on the NP photoreactive groups through termination reactions (Scheme 7c). The competition between the triplet and singlet states of the nitrene species explains its lower reactivity comparing to benzophenone, since the sole triplet state can lead to the partial penetration of the particles into the PC film. The lowest reactivity of the SiO$_2$@PFPA NPs can be attributed both to the inductive effect of the fluorine groups and to the bigger size of this particles compared to the other two types.

Finally, in order to fully characterize the chemical and physical nature of the SiO$_2$ functionalized films, the following analyses were performed: elemental composition of the surface of the functionalized films was determined using X-ray photoelectron spectroscopy (XPS) analysis (Table 5). For the three types of PC—SiO$_2$@photoreactive group films increase in the atomic concentration of the Si and O elements was detected while the PC—SiO$_2$ had quite similar composition to that of neat PC film. The small amount of Si, detected in the case of PC—SiO$_2$, is detected as siloxane bond and originates from silicon grease that was found many times in neat parylene films. This contamination was introduced to the films during the CVD process. In addition, the detection of fluorine in the case of PC—SiO$_2$@PFPA demonstrates successful incorporation of SiO$_2$@PFPA into PC films.

TABLE 5

| | | | | | | |
|---|---|---|---|---|---|---|
| | XPS and contact angle results | | | | | |
| | Atomic concentration % | | | | | Contact |
| Sample | C | Cl | Si | O | F | angle |
| PC | 85.84 | 13.57 | 0.08 | 0.58 | 0.00 | 82° |
| PC-SiO$_2$ | 83.73 | 10.46 | 1.08[a] | 4.73 | 0.00 | 74° |
| PC-SiO$_2$@PA | 75.40 | 10.74 | 4.23 | 9.63 | 0.00 | 38° |
| PC-SiO$_2$@PFPA | 76.26 | 10.71 | 3.42 | 9.00 | 0.62 | 40° |
| PC-SiO$_2$@BPh | 76.04 | 11.23 | 3.05 | 9.69 | 0.00 | 35° |

[a]siloxane bond

Contact angle measurements showed a drastic increase in the wetability of the PC films upon functionalization. The hydrophobic PC became hydrophilic after the incorporation of the hybrid photoreactive SiO$_2$ NPs while bare SiO$_2$ NPs caused only a slight decrease in θ confirming that no functionalization has occurred. This slight decrease in θ can be attributed to the partial oxidation of PC during the irradiation due to leftovers of oxygen as it was also detected by XPS (O 4.73%).

Figure 15:
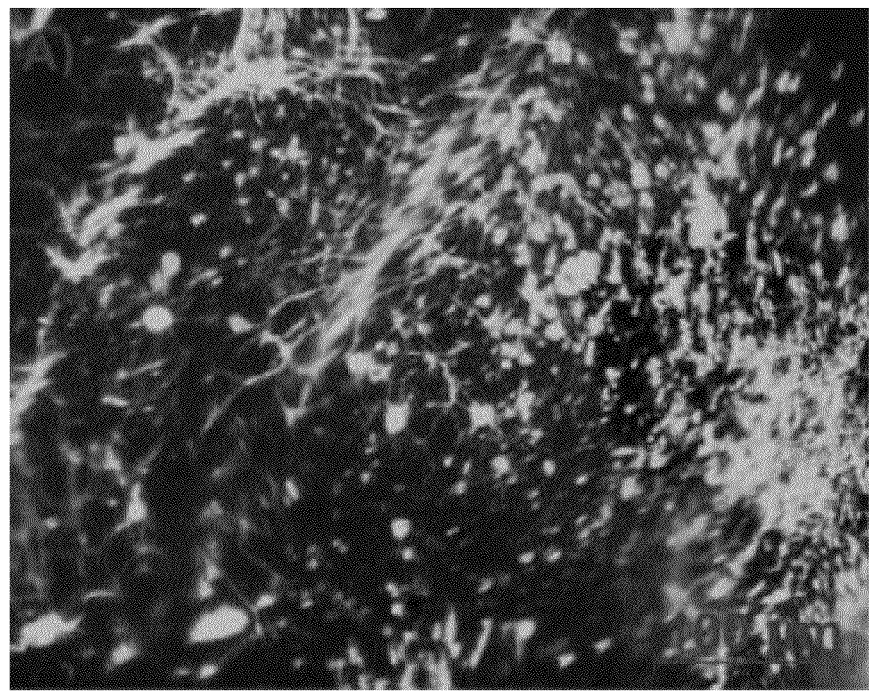
FIGS. 15A-15D show merged GFP and CFP filter fluorescence microscope images of PC—SiO$_2$@PA (FIG. 15A), PC—SiO$_2$@PFPA (FIG. 15B), PC—SiO$_2$@BPh (FIG. 15C), and PC—SiO$_2$ (FIG. 15D) films after APTES modification and incubation with fluorescent dansyl chloride.
Figure 15B:
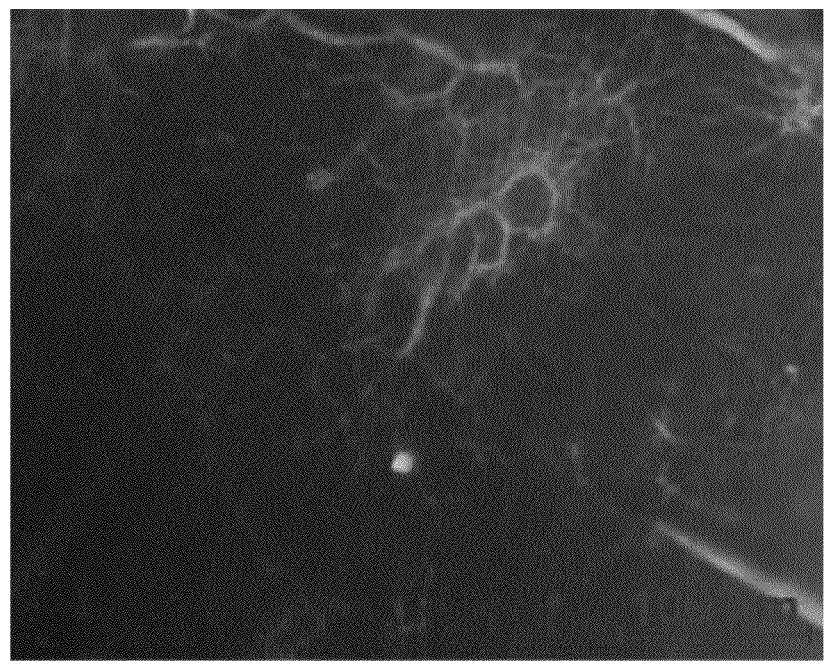
Figure 15C:
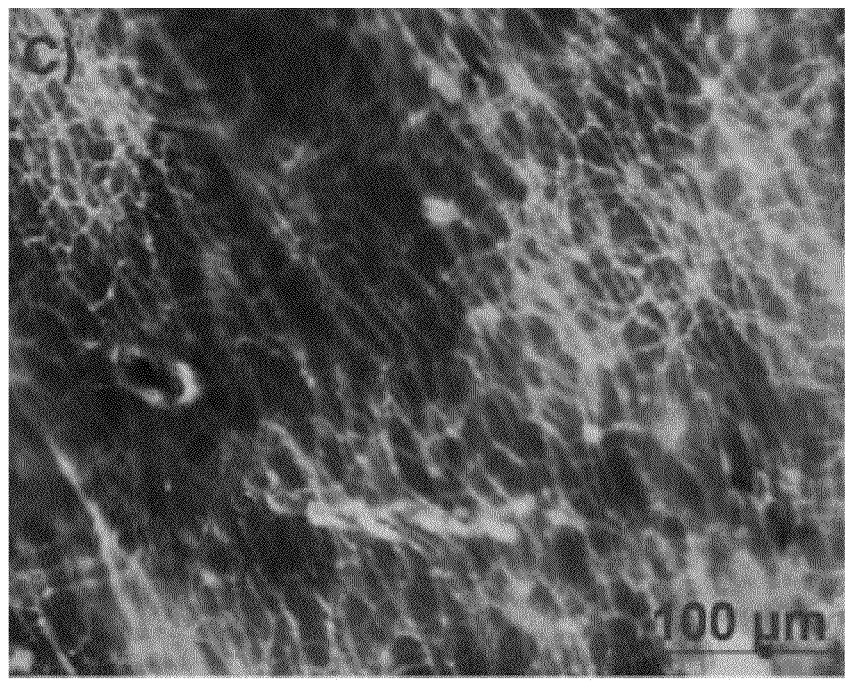
Figure 15D:
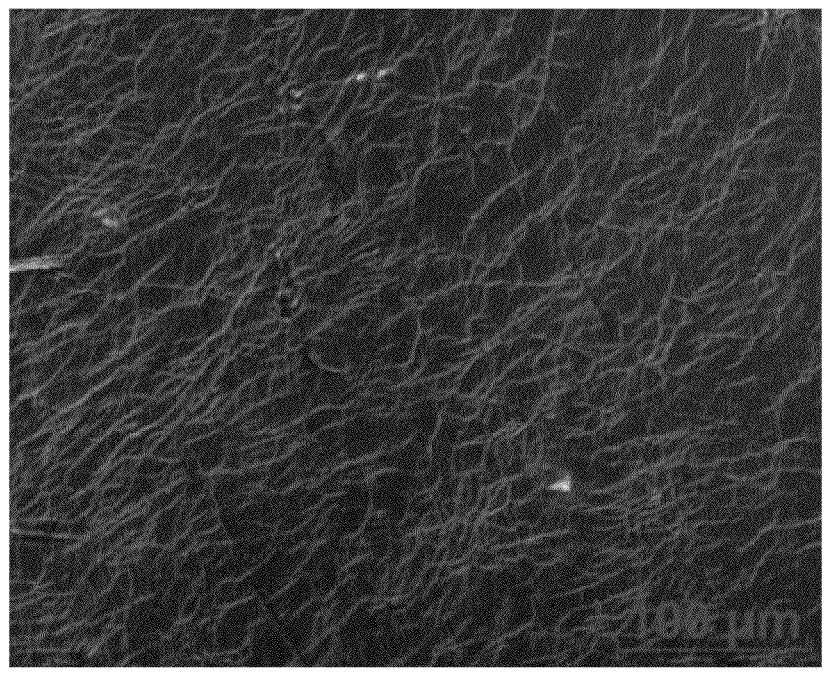

In order to demonstrate the potential of the silica functionalized PC films a second step functionalization was performed using silane-based chemistry. APTES was attached to peeled, self supported, PC films through formation of siloxane bonds. The primary amine introduced during this reaction was labeled with florescent dansyl chloride and detected with fluorescence microscope (FIG. 15A-15D). It was already found that SiO$_2$@PA and SiO$_2$@BPh NPs are more reactive than SiO$_2$@PFPA, thus they were much more incorporated into PC films. Consequently, higher amount of APTES was introduced to those films causing higher fluorescence intensity in comparison with PC—SiO$_2$@PFPA modified films (see FIGS. 15A and 15C in comparison with FIG. 15B). FIG. 15D shows fluorescence microscope image of PC—SiO$_2$, and as it can be seen no fluorescence is observed. This observation not only proves the selective reaction of APTES with SiO$_2$ NPs but also provides additional evidence to the fact that only photoreactive SiO$_2$ NPs had reacted with PC.

SCHEMES

Scheme 1: Synthesis of (S) 6-(4-Benzoyl-benzoylamino)-2-carbazol-9-yl-hexanoic acid (7)

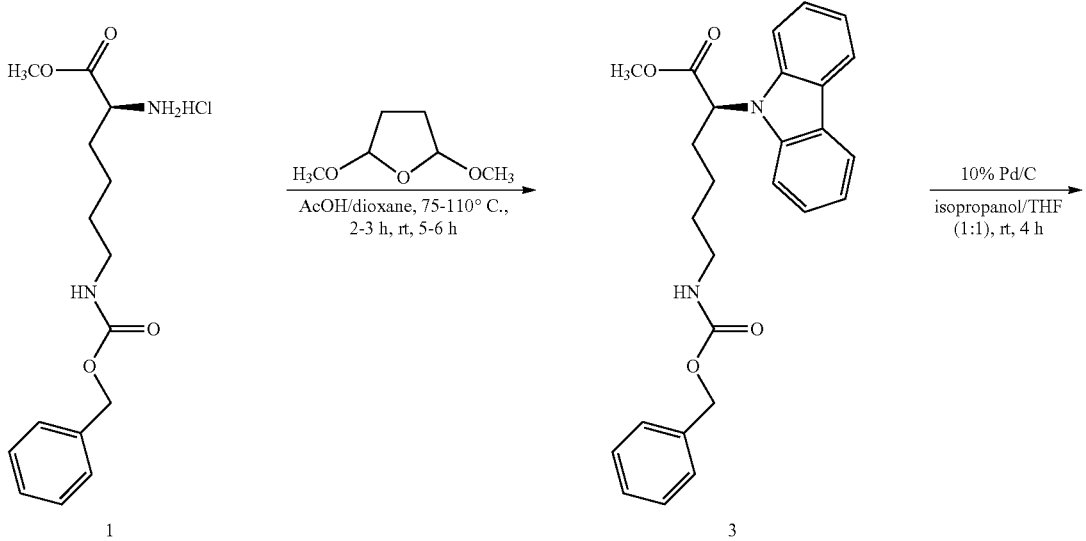

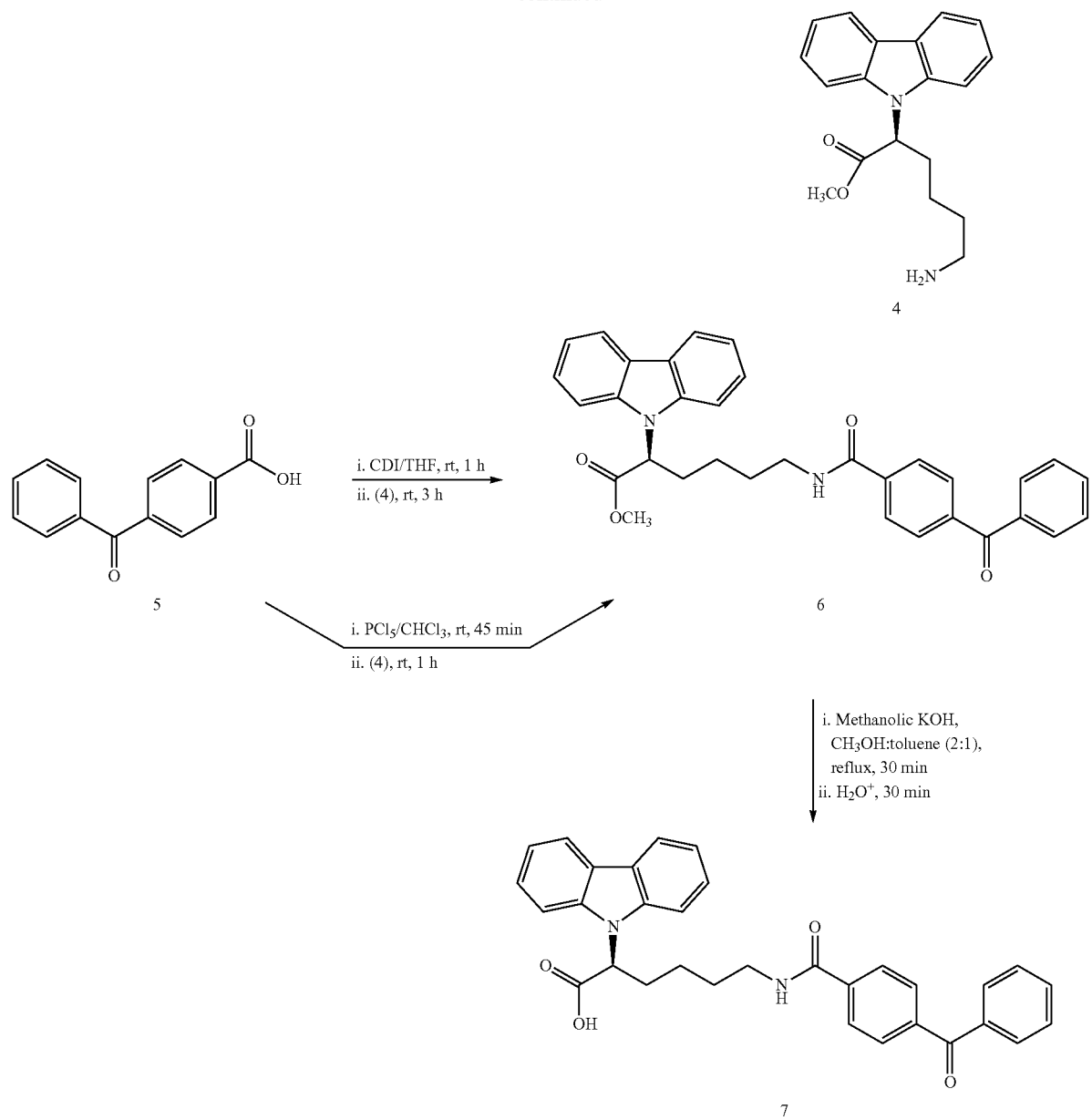
Scheme 2: Synthesis of (S)-6-(4-azido-benzoylamino)-2-carbazol-9-yl-hexanoic acid (14):
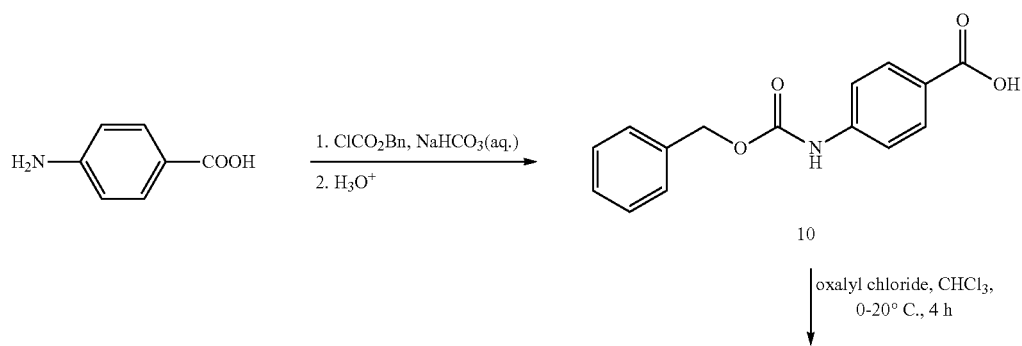

41
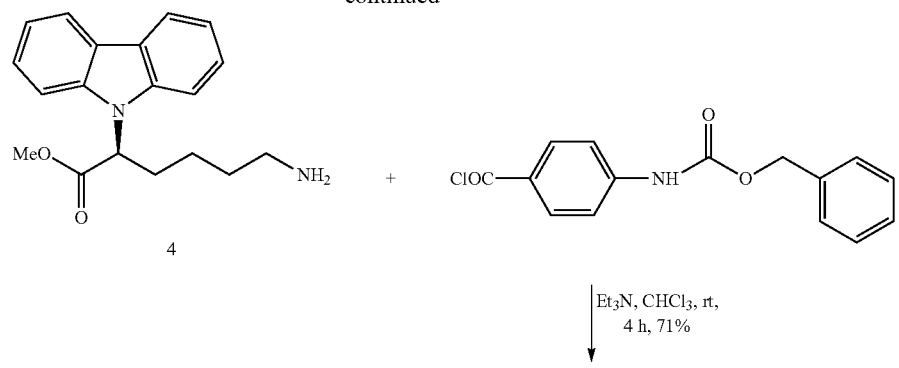
-continued
42
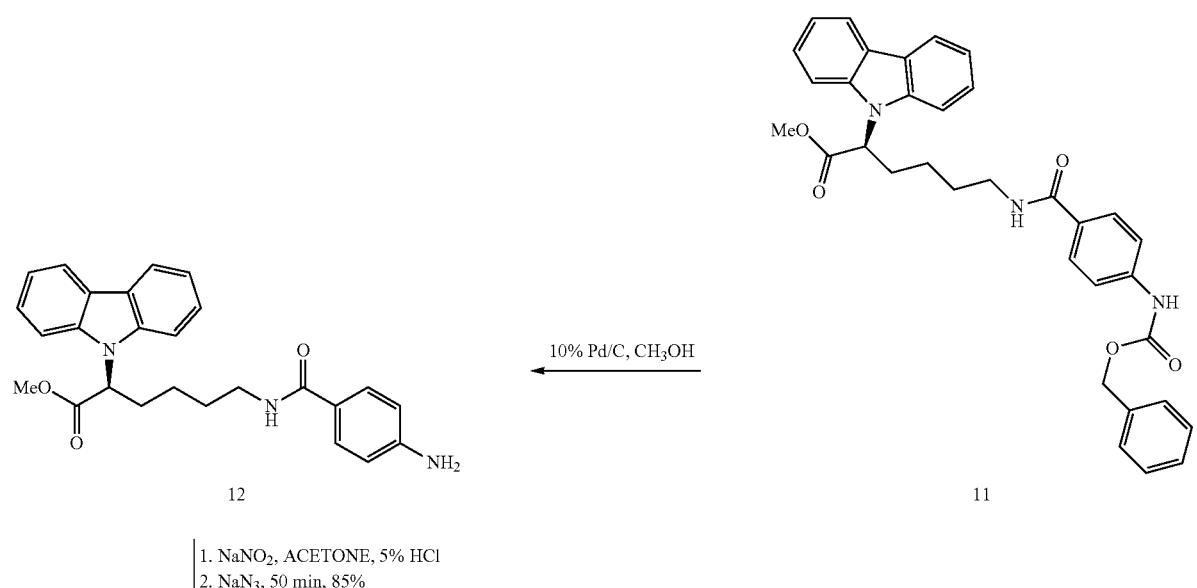
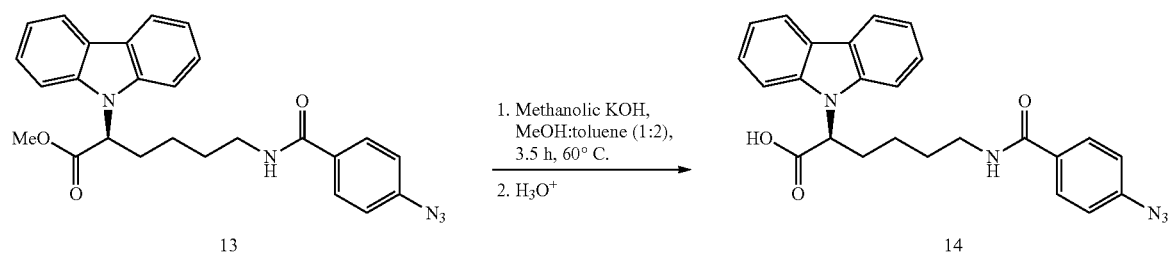

Scheme 3: Synthesis of (S)-4-(2-(4-azidobenzoyloxy)ethoxy)-2-(9h-carbazol-9-yl)-4-oxobutanoic acid (20)
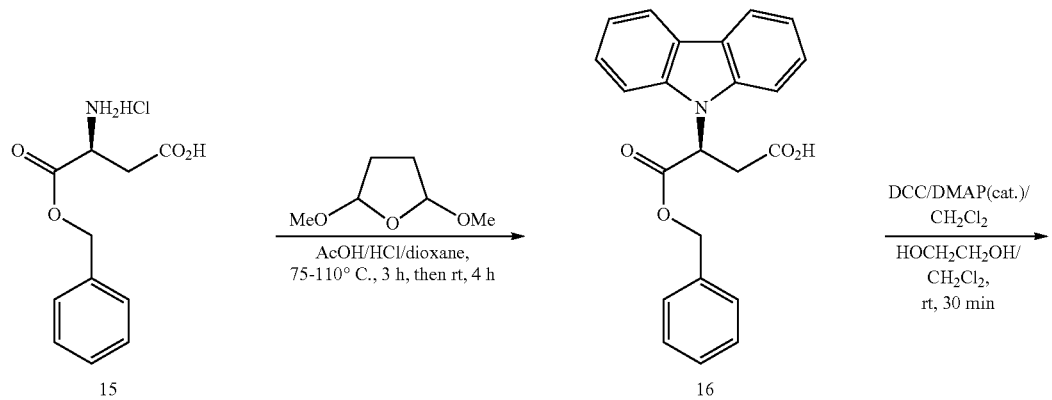
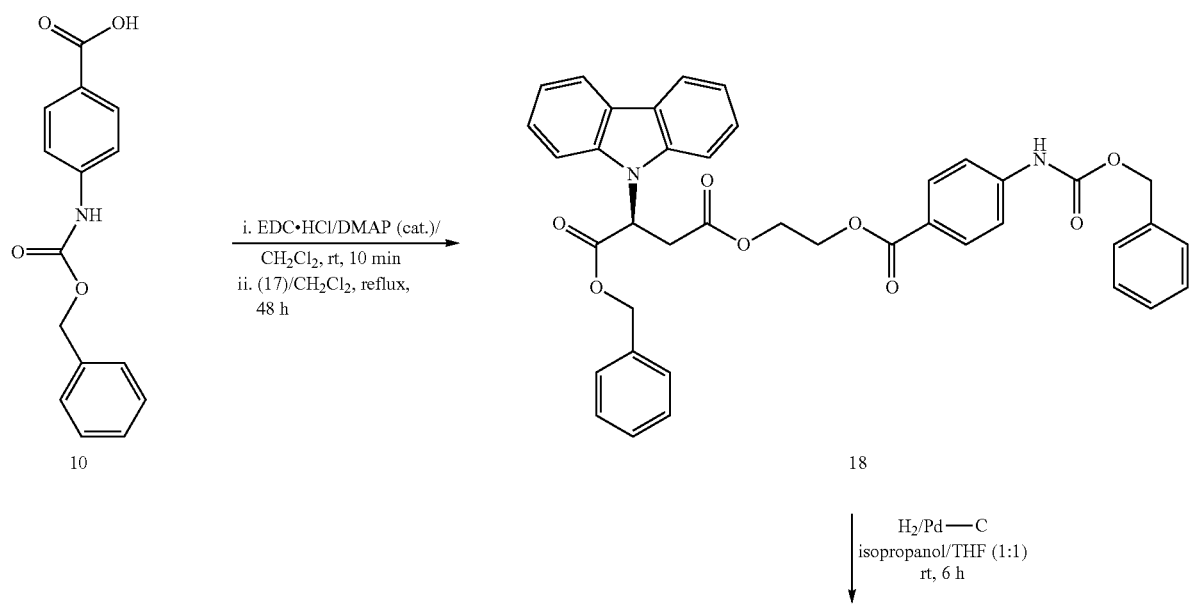

-continued
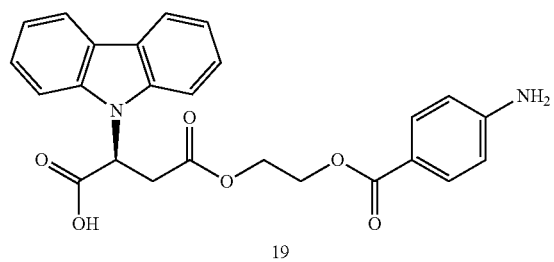
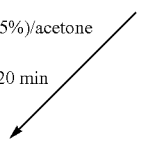
i. NaNO₂/HCl (5%)/acetone
   0° C., 20 min
ii. NaN₃, 0° C., 20 min
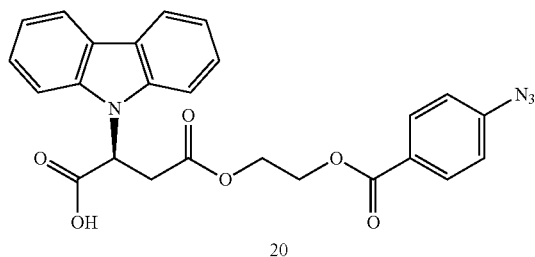
Scheme 4: Synthesis of (S)-5-(2-(4-azidobenzoyloxy)ethoxy)-2-(9H-carbazol-9-yl)-5-oxopentanoic acid (26)
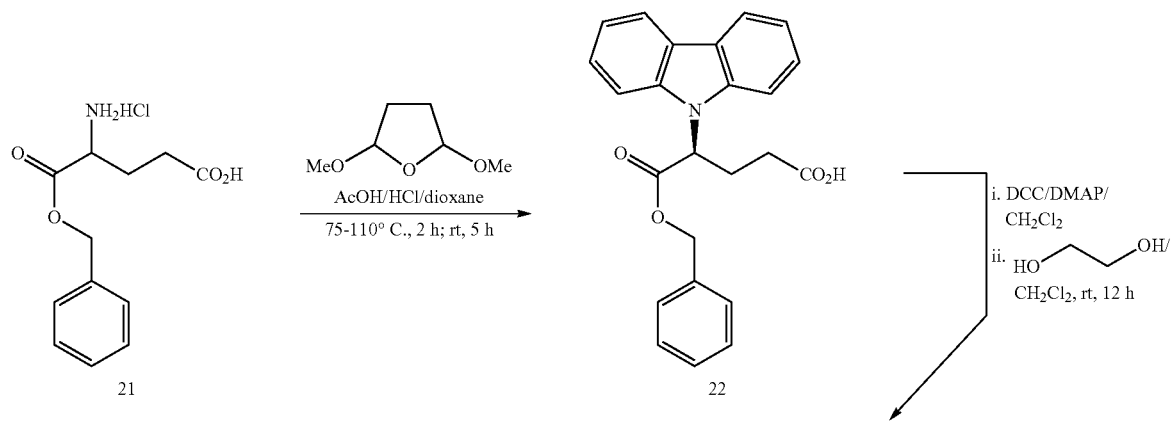

-continued
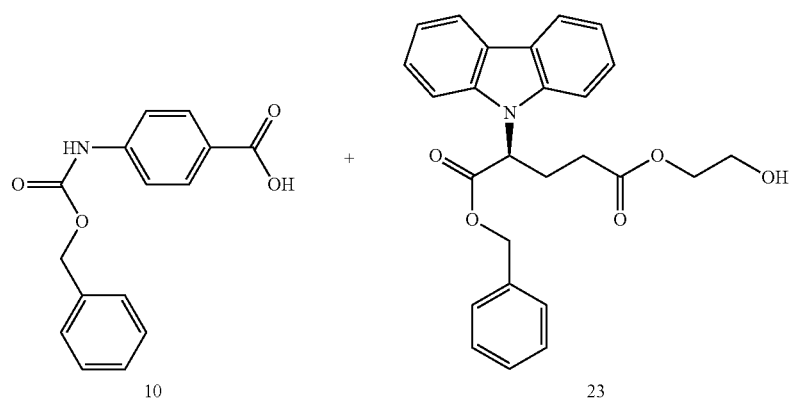
10 + 23
EDC·HCl/DMAP (cat.)/CH$_2$Cl$_2$,
rt, 20 min; reflux at 40° C., 6 h
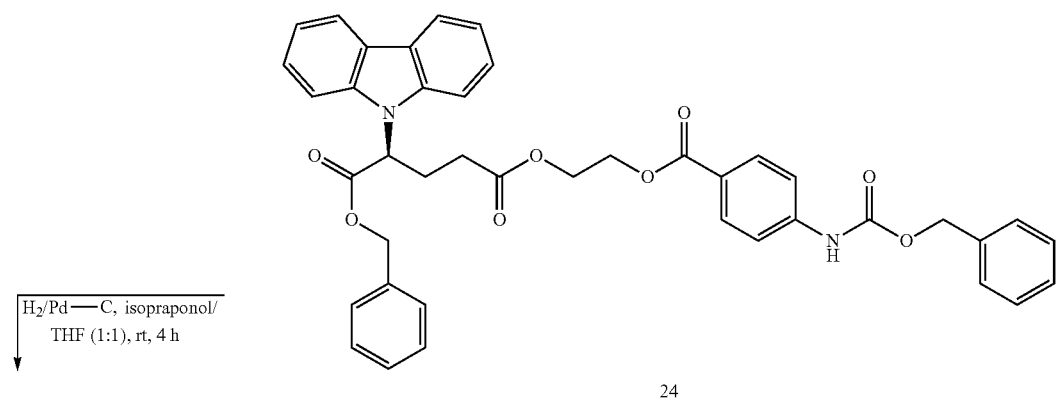
24
H$_2$/Pd—C, isoproponol/
THF (1:1), rt, 4 h
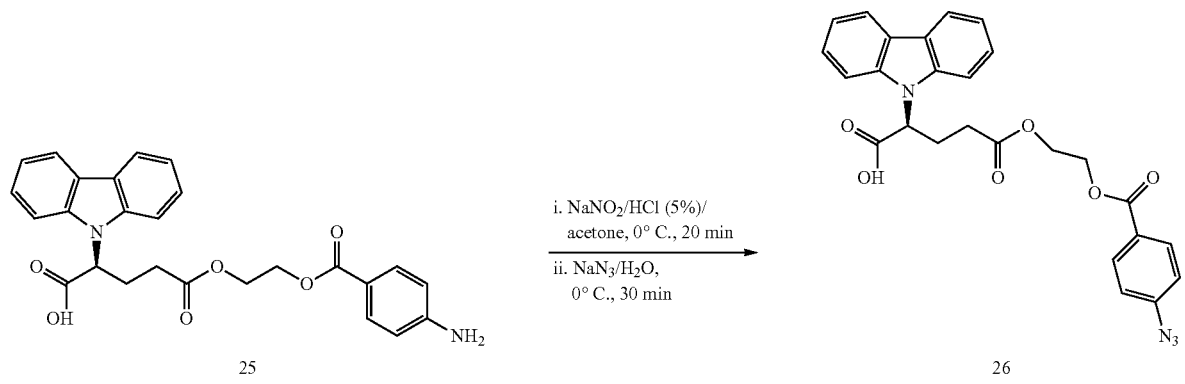 [SMILES: Nc1ccc(C(=O)OCCOC(=O)CC[C@@H](C(=O)O)n2c3ccccc3c3ccccc32)cc1 ; [N-]=[N+]=Nc1ccc(C(=O)OCCOC(=O)CC[C@@H](C(=O)O)n2c3ccccc3c3ccccc32)cc1]
25
i. NaNO$_2$/HCl (5%)/
acetone, 0° C., 20 min
ii. NaN$_3$/H$_2$O,
0° C., 30 min
26

Scheme 5: Sol-gel preparation of SiO$_2$@photoreactive NPs
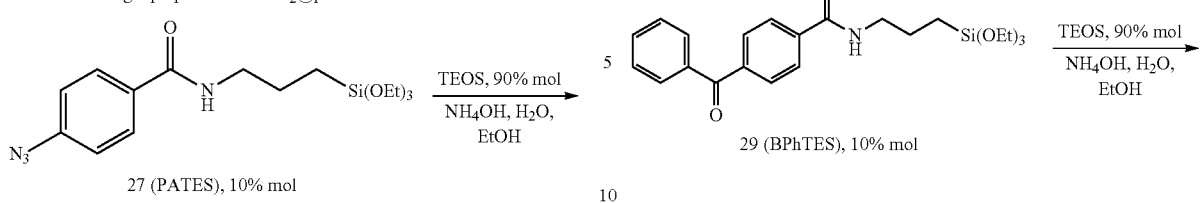
27 (PATES), 10% mol
29 (BPhTES), 10% mol
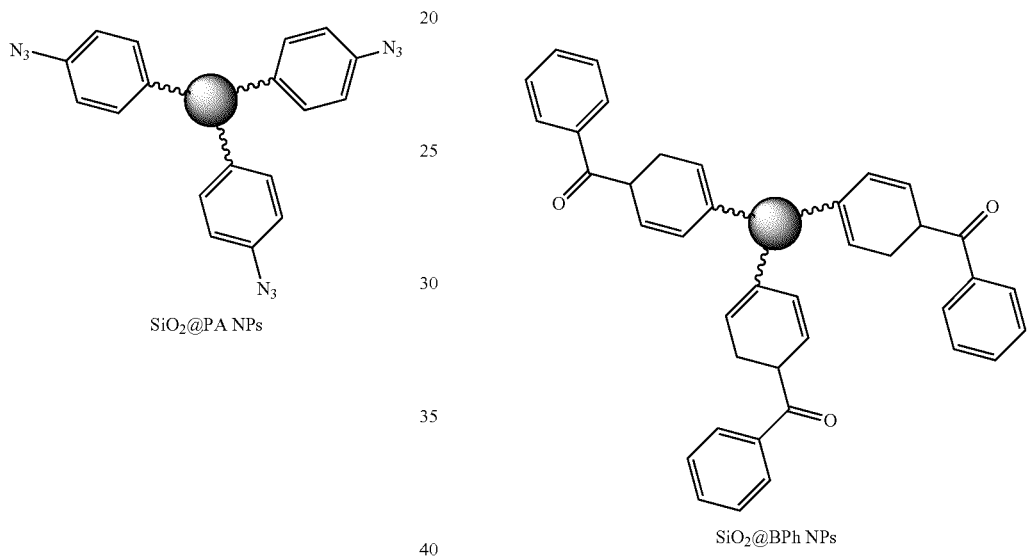
SiO$_2$@PA NPs
SiO$_2$@BPh NPs
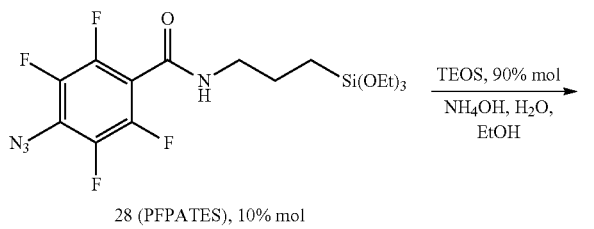
28 (PFPATES), 10% mol
SiO$_2$@PFPA NPs
Scheme 6: Schematic representation of the covalent modification of parylene C films using SiO$_2$@PA NPs
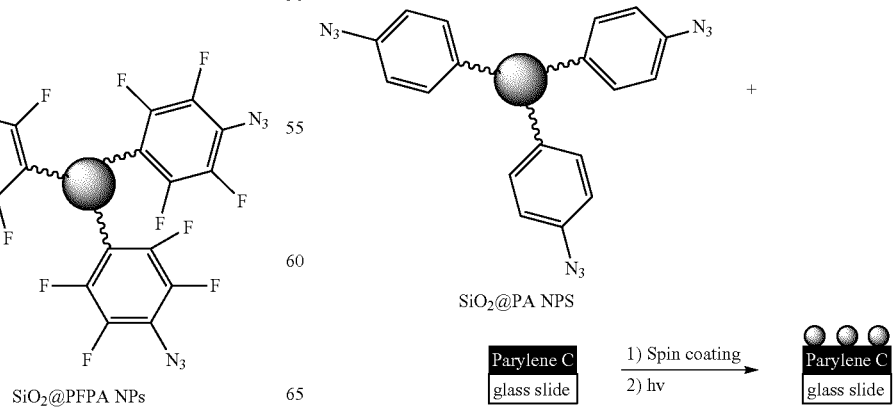
SiO$_2$@PA NPS Scheme 7: Proposed mechanisms for the photochemical reaction of SiO$_2$@photoreactive group NPs with PC
a)
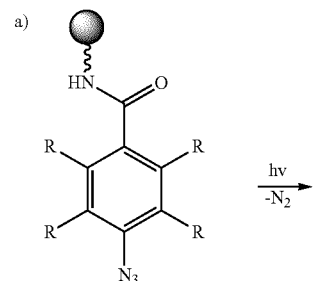
R = H  SiO$_2$@PA
R = F  SiO$_2$@PFPA
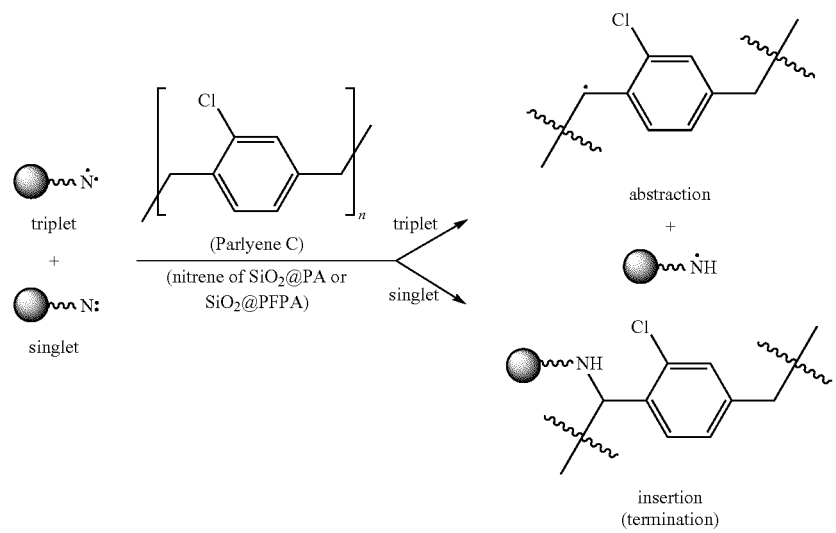
b)
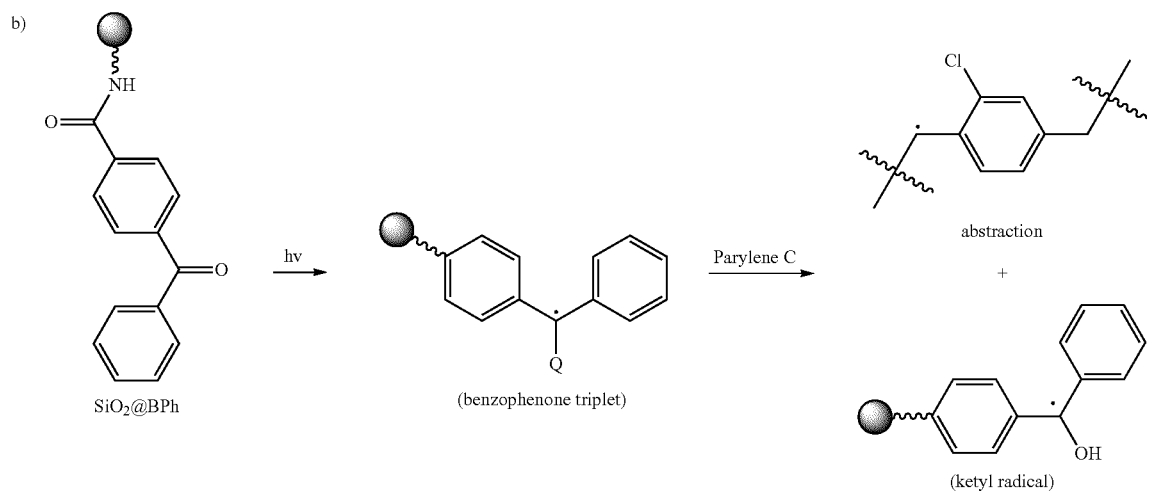
c)
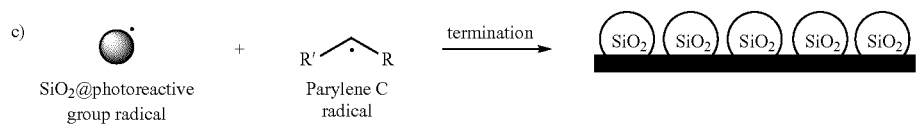

REFERENCES

Applerot, G.; Abu-Mukh, R.; Irzh, A.; Charmet, J.; Keppner, H.; Laux, E.; Guibert, G.; Gedanken, A. *ACS Appl. Mater. Interfaces*, 2010, 2, 1052-1059

Bartlett, M. A.; Yan, M. *Advanced Materials and Processes*, 2001, 13, 1449-1451

Bera, M.; Rivaton, A.; Gandon, C.; Gardette, J. L. *Eur. Polym. J.*, 2000, 36, 1765-1777

Braeuchle, C. D. M. Burland, G. C. Bjorklund, *J. Phys. Chem.*, 1981, 85, 123-127

Chen, H.-Y.; Elkasabi, Y.; Lahann, J. *J. Am. Chem. Soc.* 2006, 128, 374-380

Gann, J. P.; Yan, M. *Langmuir*, 2008, 24, 5319-5323

Garcia, N.; Benito, E.; Guzman, J.; Tiemblo, P. *J. Amer. Chem. Soc.*, 2007, 129, 5052-5060

Goda, T.; Konno, T.; Takai, M.; Ishihara, K. *Colloids and Surfaces, B: Biointerfaces*, 2007, 54, 67-73

Greiner, A.; Mang, S.; Schaefer, O.; Simon, P. *Acta Polym.*, 1997, 48, 1-15

Hansen, L. T.; Kuhle, A.; Sorensen, A. H.; Bohr, J.; Lindelof, P. E. *Nanotechnology*, 1998, 9, 337-342

Helmecke, O.; Hirsch, A.; Behrens, P.; Menzel, H. *Colloid and Polymer Science*, 2008, 286, 225-231

Herrera-Alonso, M.; McCarthy, T. J. *Langmuir*, 2004, 20, qzc569184-9189

Lahann, J.; Klee, D.; Hoecker, H. *Macromol. Rapid Commun.*, 1998, 19, 441-444

Lahann, J.; Choi, I. S.; Lee, J.; Jensen, K. F.; Langer, R. *Angew. Chem. Int. Ed.*, 2001, 40, 3166-3169

Lahann, J.; Langer, R. *Macromolecules*, 2002a, 35, 4380-4386

Lahann, J.; Balcells, M.; Rodon, T.; Lee, J.; Choi, I. S.; Jensen, K. F.; Langer, R. *Langmuir*, 2002b, 18, 3632-3638

Lahann, J.; Langer, R.; Jensen, K. F., *Reactive polymer coatings including poly[p-xylylene carboxylic acid pentafluorophenolester-co-p-xylylene] and use for microarrays*, 2003, 2002-US23259 2003010354

Lee, J.; Lee, Y.; Youn Jong, K.; Na Hyon, B.; Yu, T.; Kim, H.; Lee, S.-M.; Koo, Y.-M.; Kwak Ja, H.; Park Hyun, G.; Chang Ho, N.; Hwang, M.; Park, J.-G.; Kim, J.; Hyeon, T. *Small*, 2008, 4, 143-52

Li, H.; McGall, G. *Frontiers in Biochip Technology*; Springer, 2006

Liu, L.; Engelhard, M. H.; Yan, M. *J. Amer. Chem. Soc.*, 2006, 128, 14067-14072

Liu, L.; Yan, M. *Angewandte Chemie, International Edition* 2006, 45, 6207-6210

Lu, X., F. Sun, J. Wang, J. Zhong and Q. Dong, *Macromol. Rapid Commun.*, 2009, 30, 2116-2120

Mori, T.; Mizutani, T.; Ieda, M. *J. Phys. D: Appl. Phys.*, 1990, 23, 338-41

Patai, S. *The chemistry of the azido group*; Interscience Publishers: London, 1971

Peled, A., Kotlyar, V., Lellouche, J. P., *Journal of Materials Chemistry*, 2009, 19, 268-273

Philipse, A. P. and A. Vrij, *J. Colloid Interface Sci.*, 1989, 128, 121-136.

Prucker, O.; Naumann, C. A.; Ruehe, J.; Knoll, W.; Frank, C. W. *J. Amer. Chem. Soc*, 1999, 121, 8766-8770

Pruden, K. G.; Sinclair, K.; Beaudoin, S. *Journal of Polymer Science, Part A: Polymer Chemistry*, 2003, 41, 1486-1496

Radhakrishnan, B., A. N. Constable and W. J. Brittain, *Macromol. Rapid Commun.*, 2008, 29, 1828-1833.

Reiser, A.; Leyshon, L. J. *J. Amer. Chem. Soc.*, 1971, 93, 4051-2

Rohr, T.; Ogletree, D. F.; Svec, F.; Frechet, J. M. J. *Adv. Funct. Mater.*, 2003, 13, 264-270

Samuel, J. D. J. S.; Ruehe, J. *Langmuir*, 2004, 20, 10080-10085

Sindorf, D. W.; Maciel, G. E. *J. Amer. Chem. Soc*, 1981, 103, 4263-5

Stoeber, W.; Fink, A.; Bohn, E. *Journal of Colloid and Interface Science* 1968, 26, 62-9

Ten Eyck, G. A.; Pimanpang, S.; Juneja, J. S.; Bakhru, H.; Lu, T.-M.; Wang, G.-C. *Chem. Vap. Deposition*, 2007, 13, 307-311

Van Blaaderen, A. and A. Vrij, *J. Colloid Interface Sci.*, 1993, 156, 1-18.

Van Blaaderen. A. and A. Vrij, *Langmuir*, 1992, 8, 2921-2931.

Williams, S. K.; Babcock, D. E.; Chinn, J. A.; Clapper, D. L., *Implantable medical articles having pro-healing coatings*, 2008, 2007-US15469 2008008253

Yan, M.; Ren, J. *Chemistry of Materials*, 2004, 16, 1627-1632

Yan, M.; Ren, J. *Journal of Materials Chemistry*, 2005, 15, 523-527

The invention claimed is:

1. A surface-modified polymer film, wherein the polymer is parylene C, parylene N, parylene D, or parylene F, and the surface of said polymer film is modified by covalent binding of nano- or micro-particles comprising a photoreactive species.

2. The surface-modified polymer film according to claim 1, wherein the polymer is parylene C.

3. The surface-modified polymer film according to claim 2, wherein the surface of the parylene c film is modified by covalent binding of nano- or micro-particles of a hybrid organic-inorganic oxide network comprising a photoreactive species.

4. The surface-modified polymer film according to claim 3, wherein the hybrid photoreactive organic-inorganic oxide network is composed of molecules of the formula II:

$$Z-[O_3Si-(CH_2)_n-Y-B]_{n'} \quad\quad II$$

wherein:
Z is an inorganic oxide selected from the group consisting of $SiO_2$, $TiO_2$, $Al_2O_3$, $ZrO_2$, $SeO_2$, and $SeO_3$ and the group capable of reacting with a nucleophile is OH or OR, wherein R is alkyl or aryl;

B is a photoreactive moiety derived from an aryl azide, a diaryl ketone, or a fluorinated (aryl) aziridine;

Y is a divalent radical selected from the group consisting of —O—CO—, —CO—O—, —NH—CO—, and —CO—NH—;

n is 2 to 4 and n' is 1 to 3.

5. The surface-modified polymer film according to claim 1, wherein the surface of said polymer film is modified by covalent binding of nano- or micro-particles of a hybrid organic-inorganic oxide network comprising a photoreactive species and the inorganic oxide network is composed of $SiO_2$, $TiO_2$, $Al_2O_3$, $ZrO_2$, $SeO_2$, and $SeO_3$ molecules, the photoreactive moiety is derived from an aryl azide, a diaryl ketone, and a fluorinated (aryl) aziridine; and the inorganic oxide molecule is attached to the moiety of the photoreactive species by an aliphatic chain via a linker.

6. The surface-modified polymer film according to claim 5, wherein the hybrid organic-inorganic oxide network comprising a photoreactive species is composed of molecules of the formula II:

$$Z-[O_3Si-(CH_2)_n-Y-B]_{n'} \quad\quad II$$

wherein:
- Z is an inorganic oxide selected from the group consisting of $SiO_2$, $TiO_2$, $Al_2O_3$, $ZrO_2$, $SeO_2$, and $SeO_3$ and the group capable of reacting with a nucleophile is OH or OR, wherein R is alkyl or aryl;
- B is a photoreactive moiety derived from an aryl azide, a diaryl ketone, or a fluorinated (aryl) aziridine;
- Y is a divalent radical selected from the group consisting of —O—CO—, —CO—O—, —NH—CO—, and —CO—NH—;
- n is 2 to 4 and n' is 1 to 3.

7. The surface-modified polymer film according to claim 6, wherein the inorganic oxide is $SiO_2$, Y is —NH—CO—, B is a moiety derived from phenyl azide, tetrafluorophenyl azide or benzophenone; n is 3, and n' is 1.

8. The surface-modified polymer film according to claim 7, wherein the hybrid photoreactive organic-inorganic oxide of the formula II is selected from the group consisting of:

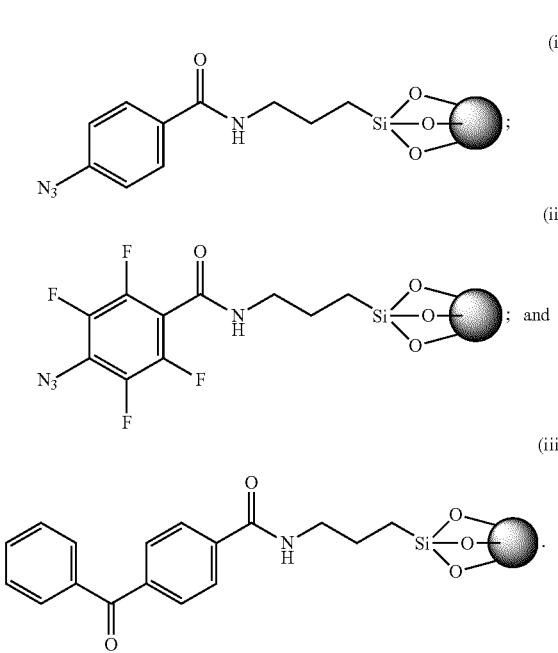

9. A hybrid organic-inorganic oxide network comprising a photoreactive species composed of molecules of the formula II:

$$Z—[O_3Si—(CH_2)_n—Y—B]_{n'} \qquad \text{II}$$

wherein:
- Z is an inorganic oxide selected from the group consisting of $SiO_2$, $TiO_2$, $Al_2O_3$, $ZrO_2$, $SeO_2$, and $SeO_3$;
- B is a photoreactive moiety derived from an aryl azide, a diaryl ketone, or a fluorinated (aryl) aziridine; and
- Y is a divalent radical selected from the group consisting of —O—CO—, —CO—O—, —NH—CO—, and —CO—NH—;
- n is 2 to 4 and n' is 1 to 3.

10. The hybrid photoreactive organic-inorganic oxide network according to claim 9, wherein the inorganic oxide is $SiO_2$, Y is —NH—CO—, B is a moiety derived from phenyl azide, tetrafluorophenyl azide or benzophenone; n is 3, and n' is 1.

11. The hybrid photoreactive organic-inorganic oxide network according to claim 10, wherein the hybrid photoreactive organic-inorganic oxide of the formula II is selected from the group consisting of:

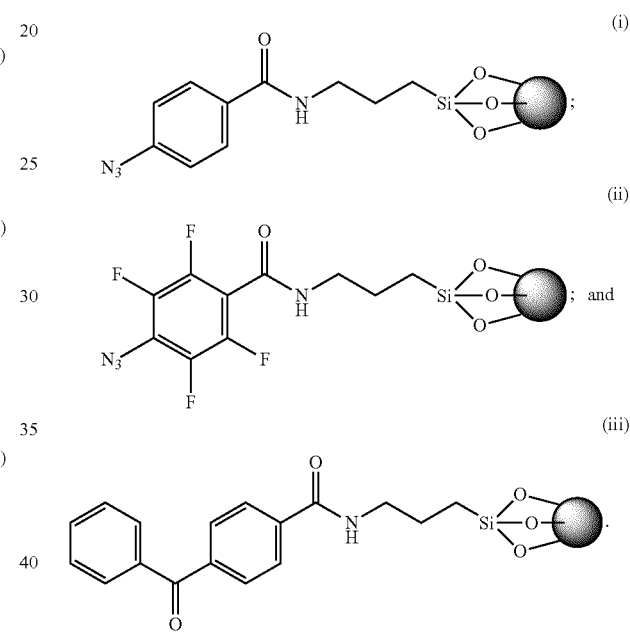

12. The hybrid photoreactive organic-inorganic oxide network according to claim 11, wherein one, two or more photoreactive moieties are attached to the inorganic oxide core.

* * * * *